(12) United States Patent
Liao et al.

(10) Patent No.: US 7,335,680 B2
(45) Date of Patent: Feb. 26, 2008

(54) PYRROLIDINE DERIVATIVES AS PROSTAGLANDIN MODULATORS

(75) Inventors: Yihua Liao, Westwood, MA (US); Zhong Zhao, Wayland, MA (US); Gian Luca Araldi, Plymouth, MA (US)

(73) Assignee: Laboratoires Serono SA, Vaud (CH)

( * ) Notice: Subject to any disclaimer, the term of this patent is extended or adjusted under 35 U.S.C. 154(b) by 116 days.

(21) Appl. No.: 10/499,346

(22) PCT Filed: Dec. 19, 2002

(86) PCT No.: PCT/EP02/14593

§ 371 (c)(1),
(2), (4) Date: Feb. 28, 2005

(87) PCT Pub. No.: WO03/053923

PCT Pub. Date: Jul. 3, 2003

(65) Prior Publication Data

US 2005/0176800 A1    Aug. 11, 2005

Related U.S. Application Data

(60) Provisional application No. 60/342,620, filed on Dec. 20, 2001.

(51) Int. Cl.
  *A61K 31/40*   (2006.01)
  *C07D 207/10*  (2006.01)
  *C07D 207/08*  (2006.01)
(52) U.S. Cl. .................. 514/428; 548/572; 548/571
(58) Field of Classification Search ................ 514/428; 548/572, 578, 579
See application file for complete search history.

(56) References Cited

U.S. PATENT DOCUMENTS

| | | |
|---|---|---|
| 3,873,566 A | 3/1975 | Scribner |
| 3,976,660 A * | 8/1976 | Ondetti et al. .............. 548/531 |
| 4,003,911 A | 1/1977 | Scribner |
| 4,033,989 A | 7/1977 | Bundy |
| 4,090,019 A | 5/1978 | Williams et al. |
| 4,211,876 A | 7/1980 | Scribner |
| 4,753,945 A | 6/1988 | Gilbard et al. |
| 5,010,086 A | 4/1991 | Lesher et al. |
| 5,091,431 A | 2/1992 | Tulshian et al. |
| 5,605,814 A | 2/1997 | Abramovitz et al. |
| 5,759,789 A | 6/1998 | Abramovitz et al. |
| 5,981,527 A | 11/1999 | Daugan et al. |
| 6,001,847 A | 12/1999 | Daugan et al. |
| 6,006,735 A | 12/1999 | Schlough et al. |
| 6,040,309 A | 3/2000 | Dack et al. |
| 6,043,252 A | 3/2000 | Bombrun |
| 6,054,475 A | 4/2000 | Martin et al. |
| 6,100,270 A | 8/2000 | Campbell |
| 6,117,881 A | 9/2000 | Bombrun |
| 6,121,279 A | 9/2000 | Gutterer |
| 6,127,363 A | 10/2000 | Doherty, Jr. et al. |
| 6,140,329 A | 10/2000 | Daugan |
| 6,143,746 A | 11/2000 | Daugan et al. |
| 6,143,757 A | 11/2000 | Daugan et al. |
| 6,156,753 A | 12/2000 | Doherty, Jr. et al. |
| 6,207,829 B1 | 3/2001 | Dunn et al. |
| 6,211,197 B1 | 4/2001 | Belley et al. |
| 6,288,120 B1 | 9/2001 | Cameron et al. |
| 6,900,336 B2 * | 5/2005 | Elworthy et al. ............ 548/551 |
| 2003/0120079 A1 * | 6/2003 | Elworthy et al. ......... 546/278.4 |

FOREIGN PATENT DOCUMENTS

| | | |
|---|---|---|
| DE | 25 27 989 | 1/1977 |
| EP | 463 756 | 1/1992 |
| EP | 752 421 | 1/1997 |
| WO | 93/06104 | 4/1993 |
| WO | 93/07149 | 4/1993 |
| WO | 93/12095 | 6/1993 |
| WO | 94/00453 | 1/1994 |
| WO | 94/05661 | 3/1994 |
| WO | 96/03380 | 2/1996 |
| WO | 96/06822 | 3/1996 |
| WO | 97/00863 | 1/1997 |
| WO | 97/00864 | 1/1997 |

(Continued)

OTHER PUBLICATIONS

Tandon et al., "Substrate Specificity of Human Prolyl-4-Hydroxylase," Bioorganic and Medicinal Chemistry Letters 8 (1998) 1139-1144.*

(Continued)

*Primary Examiner*—Rebecca Anderson
*Assistant Examiner*—Jason M Nolan
(74) *Attorney, Agent, or Firm*—Oblon, Spivak, McClelland, Maier & Neustadt, P.C.

(57) ABSTRACT

Substituted pyrrolidine compounds are provided, and methods of treatment and pharmaceutical composition that utilize or comprise one or more such compounds. Compounds of the invention are useful for a variety of therapies, including treating or preventing preterm labor, dysmenorrhea, asthma, hypertension, infertility or fertility disorder, undesired blood clotting, preeclampsia or eclampsia, an eosinophil disorder, sexual dysfunction, osteoporosis and other destructive bone disease or disorder, and other diseases and disorders associated with the prostaglandin family of compounds. In a preferred aspect, a substituted pyrrolidine compound is administered to a subject in coordination with a phosphodiesterase inhibitor compound.

45 Claims, No Drawings

FOREIGN PATENT DOCUMENTS

WO 01/46140 6/2001

OTHER PUBLICATIONS

Richard M. Scribner, "Azaprostanoids I. Synthesis of (RAC)-11-Desoxy-12-Azaprostanoids", Tetrahedron Letters, No. 43, pp. 3853-3856, XP002260529 1976.

Albert D. Cale, Jr., et al., "A series of central nervous system stimulants based on the 4-substituted 3, 3-diphenyl-2-pyrrolidinone skeleton. II", Journal of Medicinal Chemistry, vol. 10, No. 2, pp. 214-222 1967.

Manish Tandon, et al., "Substrate specificity of human prolyl-4-hydroxylase", Bioorganic & Medicinal Chemistry Letters, vol. 8, No. 10, pp. 1139-1144 1998.

G.B. Bennett, et al., Journal of Medicinal Chemistry, vol. 19, No. 5, pp. 715-719 1976.

A. Ichikawa, et al., Journal of Lipid Mediators and Cell Signalling, vol. 14, pp. 83-87 1996.

Toshiaki Minami, et al., The British Journal of Pharmacology, vol. 112, pp. 735-740 1994.

Narcisse Komas, et al., Phosphodiesterase Inhibitors, Academic Press.

Simon, J.F. MacDonald, et al., Journal of Medicinal Chemistry, vol. 41, No. 21, pp. 3919-3922 Oct. 8, 1998.

Jeremy Cooper, et al., J. Chem. Soc. Perkin Trans., vol. 1, pp. 1313-1317 1993.

Robert A. Coleman, et al., "Prostanoids and their Receptors" Comprehensive Medicinal Chemistry, vol. 3, pp. 643-714, 1990.

Robert A. Coleman, et al., Pharmacological Reviews, vol. 46, No. 2, pp. 205-229 1994.

Fumitaka Ushikubi, et al., Jpn. J. Pharmacol., vol. 83, pp. 279-285 2000.

P.J. Gardiner, Br. J. Pharmac. vol. 87, pp. 45-56 1986.

\* cited by examiner

PYRROLIDINE DERIVATIVES AS PROSTAGLANDIN MODULATORS

BACKGROUND OF THE INVENTION

1. Field of the Invention

This invention provides substituted pyrrolidine compounds, and methods of treatment and pharmaceutical compositions that utilize or comprise one or more such compounds. Compounds of the invention are useful for a variety of therapies, including preterm labor, dysmenorrhea, asthma, hypertension, infertility or fertility disorder, undesired blood clotting, preeclampsia or eclampsia, an eosinophil disorder, sexual dysfunction, osteoporosis and other destructive bone disease or disorder, and other diseases and disorders associated with the prostaglandin and receptors thereof.

2. Background

Certain prostanoid receptors and modulators of those receptors have been reported. See generally *Eicosanoids: From Biotechnology to Therapeutic Applications* (Plenum Press, New York); *Journal of Lipid Mediators and Cell Signalling* 14: 83-87 (1996); *The British Journal of Pharmacology*, 112: 735-740 (1994); PCT applications WO 96/06822, WO 97/00863, WO 97/00864, and WO 96/03380; EP 752421; U.S. Pat. Nos. 6,211,197 4,211,876 and 3,873,566; and Bennett et al. *J. Med. Chem.*, 19(5): 715-717 (1976).

Certain prostaglandin ligands and analogs have been reported to provide biological activity associated with prostaglandin. See, for instance, U.S. Pat. Nos. 6,288,120; 6,211,197; 4,090,019; and 4,033,989. See also U.S. Pat. No. 4,003,911. E-type prostaglandin reported to be mediated through interaction with the prostaglandin E receptor(s). Four subtypes of the prostaglandin EP receptor have been identified: EP1, EP2, EP3, and EP4. See U.S. Pat. Nos. 5,605,814 and 5,759,789. See U.S. Pat. No. 5,605,814.

It would be desirable to have new compounds and methods for treatment of diseases and disorders associated with the prostaglandin family of compounds.

SUMMARY OF THE INVENTION

We have now found substituted pyrrolidine compounds that are useful for a variety of therapies, including alleviating, preventing and/or treating preterm labor, dysmenorrhea, asthma, hypertension, sexual dysfunction, osteoporosis and other destructive bone disease or disorder, inflammation, and other diseases and disorders associated with the prostaglandin.

Preferred compounds of the invention are substituted at least two other pyrrolidine ring positions in addition to N-substitution, particularly at the 2 and 3 ring positions in addition to N-substitution.

Generally preferred for use in accordance with the invention are substituted pyrrolidine compounds of the following Formula I:

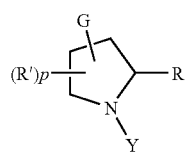

wherein Y, R and each R' are each independently hydrogen or a non-hydrogen substituent, preferably where one or both of R and R' are non-hydrogen substituents such as optionally substituted alkyl preferably having 1 to about 20 carbons; optionally substituted alkenyl preferably having from 2 to about 20 carbons; optionally substituted alkynyl preferably having from 2 to about 20 carbons; optionally substituted heteroalkyl preferably having from 1 to about 20 carbons; optionally substituted heteroalkenyl preferably having from 2 to about 20 carbons; optionally substituted heteroalkynyl preferably having from 2 to about 20 carbons; optionally substituted carbocyclic aryl; optionally substituted aralkyl; optionally substituted heteroalicyclic; optionally substituted heteroaryl; optionally substituted heteroarylalkyl; or optionally substituted heteroalicyclicalkyl;

G is oxo (=O), halogen particularly Cl or F, optionally substituted alkyl particularly fluoroalkyl, optionally substituted alkoxy, hydroxy, carboxylate, or optionally substituted alkylcarboxylate ester;

p is an integer of from zero (i.e. no R' groups) to 4; and pharmaceutically acceptable salts thereof.

For many applications, more preferred are N-substituted pyrrolidine compounds of the following Formula II:

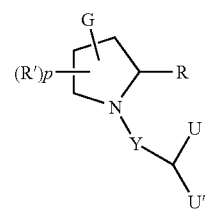

wherein R, R', G and p are the same as defined in Formula I above;

Y is $(CR^2R^3)_q$ which may include 0 or 1 carbon-carbon double bond or triple bond, q is from 1 to 6 and $R^2$ and $R^3$ are each independently selected at each occurrence from the group consisting of hydrogen, hydroxy, halogen, optionally substituted alkyl preferably having from 1 to about 12 carbon atoms, optionally substituted alkenyl preferably having from 2 to about 12 carbon atoms, optionally substituted alkynyl preferably having from 2 to about 12 carbon atoms, optionally substituted heteroalkyl preferably having from 1 to about 12 carbon atoms particularly optionally substituted alkoxy preferably having from 1 to about 12 carbon atoms, optionally substituted heteroalkenyl preferably having from 2 to about 12 carbon atoms, optionally substituted heteroalkynyl preferably having from 2 to about 12 carbon atoms, or $R^2$ and $R^3$ together may be a single oxygen to provide a carbonyl (>C=O) group; and U and U' are each independently selected from hydrogen, hydroxy, optionally substituted alkyl preferably having from 1 to about 12 carbon atoms, optionally substituted cycloalkyl preferably having 3 to about 8 carbon ring atoms, optionally substituted alkenyl preferably having from 2 to about 12 carbon atoms, optionally substituted alkynyl preferably having from 2 to about 12 carbon atoms, optionally substituted heteroalkyl preferably having from 1 to about 12 carbon atoms particularly optionally substituted alkoxy preferably having from 1 to about 12 carbon atoms, optionally substituted heteroalkenyl preferably having from 2 to about 12 carbon atoms, optionally substituted heteroalkynyl preferably having from 2 to about 12 carbon atoms; and pharmaceutically acceptable salts thereof.

Also preferred are compounds of the following Formula III:

$$\text{III}$$

(R')p—[structure with G, A, B—V—L, N, Y, U, U']

wherein G, R' and p are the same as defined in Formula I; and Y, U, U' and q are the same as defined in Formula II;

A is O, S, $(CR^2R^3)_{q'}$ where q' is an integer of from 1 to 6;

B is $(CR^2R^3)$, or absent; or

A and B taken in combination form an optionally substituted 1,2-vinylene group or an ethynyl group;

V is $(CR^2R^3)_m$, optionally substituted divalent aryl, or optionally substituted divalent heteroaryl;

L is C(O)Z;

Z is hydroxy, optionally substituted alkyl preferably having 1 to about 12 carbon atoms, optionally substituted alkenyl preferably having 2 to about 12 carbon atoms, optionally substituted alkynyl preferably having 2 to about 12 carbon atoms, optionally substituted heteroalkyl preferably having from 1 to about 12 carbon atoms particularly optionally substituted alkoxy preferably having from 1 to about 12 carbon atoms, optionally substituted heteroalkenyl preferably having from 2 to about 12 carbon atoms, optionally substituted heteroalkynyl preferably having from 2 to about 12 carbon atoms, amino, $NR^4R^5$, optionally substituted cycloalkyl preferably having 3 to 8 ring carbon atoms, optionally substituted heterocycloalkyl preferably having 3 to 8 ring atoms with at least one N, O or S ring atoms, optionally substituted carbocyclic aryl, optionally substituted heteroaryl, optionally substituted arylalkyl preferably $arylC_{1-4}alkyl$, or optionally substituted heteroarylalkyl preferably $heteroarylC_{1-4}alkyl$;

n is an integer selected from 0-3;

m is an integer selected from 1-6;

$R^2$, $R^3$ and q are the same as defined in Formula II;

$R^4$ and $R^5$ are independently selected at each occurrence from the group consisting of hydrogen optionally substituted alkyl preferably having 1 to about 12 carbon atoms, optionally substituted cycloalkyl preferably having 3 to about 8 ring carbon atoms, optionally substituted heterocycloalkyl preferably having 3 to about 8 ring atoms at least one of which is N, O or S, optionally substituted alkenyl preferably having 2 to about 12 carbon atoms, optionally substituted alkynyl preferably having 2 to about 12 carbon atoms, optionally substituted heteroalkyl preferably having from 1 to about 12 carbon atoms particularly optionally substituted alkoxy preferably having from 1 to about 12 carbon atoms, optionally substituted heteroalkenyl preferably having from 2 to about 12 carbon atoms, optionally substituted heteroalkynyl preferably having from 2 to about 12 carbon atoms, optionally substituted carbocyclic aryl, optionally substituted heteroaryl, optionally substituted arylalkyl, and optionally substituted heteroarylalkyl, or $R^4$ and $R^5$ taken in combination is an optionally substituted heterocycloalkyl preferably having 3 to about 8 ring atoms at least one of which is N, O or S; and pharmaceutically acceptable salts thereof.

Preferred compounds of the invention also include those of the following Formula IV:

$$\text{IV}$$

[structure with G, A, B—V—L, N, Q, U, HO]

wherein

A is O, S, $CR^2R^3$;

B is $(CR^2R^3)_n$, or absent; or

A and B taken in combination form an optionally substituted 1,2-vinylene group or an ethynyl group;

V is $(CR^2R^3)_m$, optionally substituted divalent aryl, or optionally substituted divalent heteroaryl;

L is C(O)Z;

G is oxo (=O), halo particularly Cl or F, optionally substituted alkyl, optionally substituted alkoxy, optionally substituted fluoroalkyl, hydroxy, carboxylate, or optionally substituted alkylcarboxylate ester;

Q is $(CR^2R^3)_q$ which may include 0 or 1 C=C double bonds;

U is an optionally substituted alkyl group;

Z is hydroxy, optionally substituted alkyl preferably having 1 to about 12 carbon atoms, optionally substituted alkenyl preferably having 2 to about 12 carbon atoms, optionally substituted alkynyl preferably having 2 to about 12 carbon atoms, optionally substituted heteroalkyl alkyl preferably having from 1 to about 12 carbon atoms particularly optionally substituted alkoxy preferably having from 1 to about 12 carbon atoms, optionally substituted heteroalkenyl preferably having from 2 to about 12 carbon atoms, optionally substituted heteroalkynyl preferably having from 2 to about 12 carbon atoms, amino, $NR^4R^5$, optionally substituted cycloalkyl preferably having 3 to 8 carbon ring atoms, optionally substituted heterocycloalkyl preferably having 3 to 8 ring atoms with at least one N, O or S ring atom, optionally substituted carbocyclic aryl, optionally substituted heteroaryl, optionally substituted arylalkyl preferably $arylC_{1-4}alkyl$, or optionally substituted heteroarylalkyl preferably $heteroarylC_{1-4}alkyl$;

n is an integer selected from 0-3;

m is an integer selected from 1-6;

q is an integer selected from 0-5;

$R^2$ and $R^3$ are independently selected at each occurrence from the group consisting of hydrogen, hydroxy, halogen, optionally substituted alkyl preferably having 1 to about 12 carbon atoms, optionally substituted alkenyl preferably having 2 to about 12 carbon atoms, optionally substituted alkynyl preferably having 2 to about 12 carbon atoms, optionally substituted heteroalkyl preferably having from 1 to about 12 carbon atoms particularly optionally substituted alkoxy preferably having from 1 to about 12 carbon atoms, optionally substituted heteroalkenyl preferably having from 2 to about 12 carbon atoms, optionally substituted heteroalkynyl preferably having from 2 to about 12 carbon atoms; and $R^4$ and $R^5$ are independently selected at each occurrence from the group consisting of hydrogen, optionally substituted alkyl preferably having 1 to about 12 carbon atoms, optionally substituted cycloalkyl preferably having 3 to about 8 ring carbon atoms, optionally substituted heterocycloalkyl preferably having 3 to about 8 ring atoms at least one of which is N, O or S, optionally substituted alkenyl preferably having 2 to about 12 carbon atoms, optionally substituted alkynyl preferably having 2 to about 12 carbon atoms, optionally substituted heteroalkyl preferably having from 1 to about 12 carbon atoms particularly optionally substituted alkoxy preferably having from 1 to about 12 carbon atoms, optionally substituted heteroalkenyl preferably having from 2 to about 12 carbon atoms, optionally substituted heteroalkynyl preferably having from 2 to about 12 carbon atoms, optionally substituted carbocyclic aryl, optionally substituted heteroaryl, optionally substituted arylalkyl preferably aryl$C_{1\text{-}4}$alkyl, and optionally substituted heteroarylalkyl preferably heteroaryl$C_{1\text{-}4}$alkyl; and pharmaceutically acceptable salts thereof.

In each of Formulae I, II, III and IV, preferably G is present at the 3-position of the pyrrolidine ring. Also preferred are compounds where the 4- and 5-pyrrolidine ring positions are unsubstituted.

Preferred compounds of the invention also include those of the following Formula V:

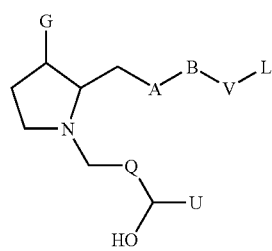

V wherein
A is selected from O and $CH_2$;
B is $CR^2R^3$ or absent wherein $R^2$ and $R^3$ are independently selected from H and optionally substituted $C_1$-$C_6$ alkyl, preferably H; or A and B taken in combination form an optionally substituted 1,2-vinylene group;
G is halogen, particularly Cl or F, preferably Cl;
L is C(O)Z;
Q is $(CR^2R^3)_q$ which may include 0 or 1 C=C double bond;
U is —$CR^6R^7$—W, wherein $R^6$ and $R^7$ are independently selected from H and optionally substituted $C_1$-$C_6$ alkyl, preferably H; or $R^6$ and $R^7$ can form an optionally substituted $C_3$-$C_6$ cycloalkyl with the carbon they are attached to, preferably an optionally substituted $C_3$ or $C_4$ cycloalkyl;
V is selected from $(CR^2R^3)_m$, optionally substituted divalent aryl and optionally substituted divalent heteroaryl;
W is selected from hydrogen, optionally substituted $C_1$-$C_6$ alkyl, optionally substituted $C_3$-$C_6$ cycloalkyl $C_1$-$C_6$ alkyl, optionally substituted aryl and optionally substituted heteroaryl;
Z is hydroxy;
m is an integer selected from 1, 2, 3, 4, 5 and 6, preferably 3;
q is an integer selected from 0, 1, 2, 3, 4 and 5, preferably selected from 1 and 2.

One more preferred group of compounds of the invention also include those of the following Formula VI:

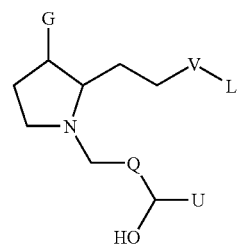

VI wherein
G is halogen, particularly Cl or F, preferably Cl;
L is C(O)Z;
Q is $(CR^2R^3)_q$ wherein $R^2$ and $R^3$ are independently selected from H and optionally substituted $C_1$-$C_6$ alkyl, preferably H;
U is —$CR^6R^7$—W, wherein $R^6$ and $R^7$ are independently selected from H and optionally substituted $C_1$-$C_6$ alkyl, preferably H; or $R^6$ and $R^7$ can form an optionally substituted $C_3$-$C_6$ cycloalkyl with the carbon they are attached to, preferably an optionally substituted $C_3$ or $C_4$ cycloalkyl;
V is selected from optionally substituted divalent aryl and optionally substituted divalent heteroaryl, preferably aryl;
W is selected from hydrogen, optionally substituted $C_1$-$C_6$ alkyl and optionally substituted $C_3$-$C_6$ cycloalkyl $C_1$-$C_6$ alkyl;
Z is hydroxy;
q is an integer selected from 1 and 2.

Another more preferred group of compounds of the invention also include those of the following Formula VII:

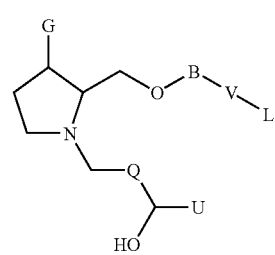

VII wherein
B is $CH_2$ or absent;
G is halogen, particularly Cl or F, preferably Cl;
L is C(O)Z;
Q is $(CR^2R^3)_q$ wherein $R^2$ and $R^3$ are independently selected from H and optionally substituted $C_1$-$C_6$ alkyl, preferably H;

U is —CR⁶R⁶⁷-W, wherein R⁶ and R⁷ are independently selected from H and optionally substituted $C_1$-$C_6$ alkyl, preferably H; or R⁶ and R⁷ can form an optionally substituted $C_3$-$C_6$ cycloalkyl with the carbon they are attached to, preferably an optionally substituted $C_3$ or $C_4$ cycloalkyl;

V is selected from optionally substituted divalent aryl and optionally substituted divalent heteroaryl;

W is selected from hydrogen, optionally substituted $C_1$-$C_6$ alkyl and optionally substituted $C_3$-$C_6$ cycloalkyl $C_1$-$C_6$ alkyl;

Z is hydroxy;

q is an integer selected from 1 or 2, preferably 1.

Another more preferred group of compounds of the invention also include those of the following Formula VIII:

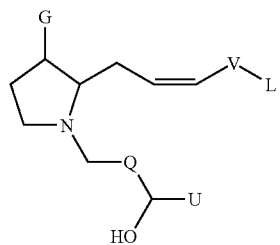

VIII wherein

G is halogen, particularly Cl or F, preferably Cl;

L is C(O)Z;

Q is $(CR^2R^3)_q$ which may include 0 or 1 C=C double bonds wherein $R^2$ and $R^3$ are independently selected from H and optionally substituted $C_1$-$C_6$ alkyl, preferably H;

U is —CR⁶R⁷—W, wherein R⁶ and R⁷ are independently selected from H and optionally substituted $C_1$-$C_6$ alkyl, preferably H; or R⁶ and R⁷ can form an optionally substituted $C_3$-$C_6$ cycloalkyl with the carbon they are attached to, preferably an optionally substituted $C_3$ or $C_4$ cycloalkyl;

V is $(CR^2R^3)_m$;

W is selected from hydrogen, optionally substituted $C_1$-$C_6$ alkyl and optionally substituted $C_3$-$C_6$ cycloalkyl $C_1$-$C_6$ alkyl;

Z is hydroxy;

m is an integer selected from 1, 2 and 3, preferably 3;

is q is an integer selected from 1 and 2, preferably 2.

Another more preferred group of compounds of the invention also include those of the following Formula IX:

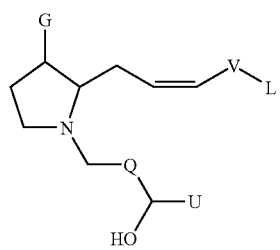

IX wherein

G is halogen, particularly Cl or F, preferably Cl;

L is C(O)Z;

Q is $(CR^2R^3)_q$ wherein $R^2$ and $R^3$ are independently selected from H and optionally substituted $C_1$-$C_6$ alkyl, preferably H;

U is —CR⁶R⁷—W, wherein R⁶ and R⁷ are independently selected from H and optionally substituted $C_1$-$C_6$ alkyl, preferably H; or R⁶ and R⁷ can form an optionally substituted $C_3$-$C_6$ cycloalkyl with the carbon they are attached to, preferably an optionally substituted $C_3$ or $C_4$ cycloalkyl;

V is $(CR^2R^3)_m$;

W is selected from optionally substituted aryl and optionally substituted heteroaryl, preferably aryl;

Z is hydroxy;

m is an integer selected from 1, 2 and 3, preferably 3;

q is an integer selected from 1 and 2, preferably 1.

Preferred compounds of the invention also include those of the following Formula X:

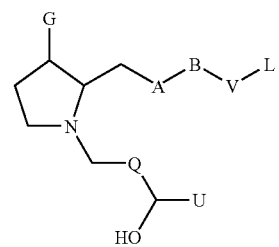

X wherein

A is selected from O and $CH_2$, preferably $CH_2$;

B is $CR^2R^3$ or absent wherein $R^2$ and $R^3$ are independently selected from H and optionally substituted $C_1$-$C_6$ alky, preferably H; or A and B taken in combination form an optionally substituted 1,2-vinylene group;

G is oxo;

L is C(O)Z;

Q is $(CR^2R^3)_q$ which may include 0 or 1 C=C double bond;

U is —CR⁶R⁷—W, wherein R⁶ and R⁷ are independently selected from H and optionally substituted $C_1$-$C_6$ alkyl, preferably H; or R⁶ and R⁷ can form an optionally substituted $C_3$-$C_6$ cycloalkyl with the carbon they are attached to, preferably an optionally substituted $C_3$ or $C_4$ cycloalkyl;

V is selected from optionally substituted divalent aryl and optionally substituted divalent heteroaryl; or when A and B taken in combination form an optionally substituted 1,2-vinylene group V is $(CR^2R^3)_m$;

W is selected from hydrogen, optionally substituted $C_1$-$C_6$ alkyl, optionally substituted $C_3$-$C_6$ cycloalkyl $C_1$-$C_6$ alkyl, optionally substituted aryl and optionally substituted heteroaryl;

Z is hydroxy, m is an integer selected from 1, 2, 3, 4, 5 and 6, preferably 3;

q is an integer selected from 0, 1, 2, 3, 4 and 5, preferably selected from 1 and 2.

Preferred compounds of the invention also include those of the following Formula X':

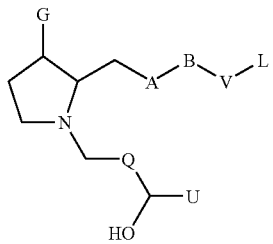

wherein

A is CH$_2$;

B is CR$^2$R$^3$ or absent wherein R$^2$ and R$^3$ are independently selected from H and optionally substituted C$_1$-C$_6$ alkyl, preferably H;

G is oxo;

L is C(O)Z;

Q is (CR$^2$R$^3$)$_q$ which may include 0 or 1 C=C double bond;

U is —CR$^6$R$^7$—W wherein R$^6$ and R$^7$ form an optionally substituted C$_3$-C$_6$ cycloalkyl with the carbon they are attached to, preferably an optionally substituted C$_3$ or C$_4$ cycloalkyl;

V is selected from (CR$^2$R$^3$)$_m$, optionally substituted divalent aryl and optionally substituted divalent heteroaryl, preferably (CR$^2$R$^3$)$_m$;

W is selected from hydrogen, optionally substituted C$_1$-C$_6$ alkyl and optionally substituted C$_3$-C$_6$ cycloalkyl C$_1$-C$_6$ alkyl;

Z is hydroxy;

m is an integer selected from 1, 2, 3, 4, 5 and 6, preferably 3;

q is an integer selected from 0, 1, 2, 3, 4 and 5, preferably selected from 1 and 2.

One more preferred group of compounds of the invention also include those of the following Formula XI:

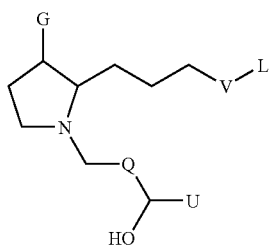

wherein

G is oxo;

L is C(O)Z;

Q is (CR$^2$R$^3$)$_q$ wherein R$^2$ and R$^3$ are independently selected from H and optionally substituted C$_1$-C$_6$ alkyl, preferably H;

U is —CR$^6$R$^7$—W, wherein R$^6$ and R$^7$ are independently selected from H and optionally substituted C$_1$-C$_6$ alkyl, preferably H; or R$^6$ and R$^7$ can form an optionally subsituted C$_3$-C$_6$ cycloalkyl with the carbon they are attached to, preferably an optionally substituted C$_3$ or C$_4$ cycloalkyl;

V is selected from optionally substituted divalent aryl and optionally substituted divalent heteroaryl, preferably aryl;

W is selected from hydrogen, optionally substituted C$_1$-C$_6$ alkyl, optionally substituted C$_3$-C$_6$ cycloalkyl C$_1$-C$_6$ alky, preferably optionally substituted C$_1$-C$_6$ alkyl;

Z is hydroxy;

m is an integer selected from 1, 2 and 3, preferably 3;

q is an integer selected from 1 and 2, preferably 1.

Another more preferred group of compounds of the invention also include those of the following Formula XII:

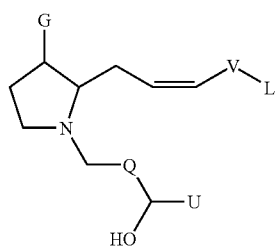

wherein

G is oxo;

L is C(O)Z;

Q is (CR$^2$R$^3$)$_q$ wherein R$^2$ and R$^3$ are independently selected from H and optionally substituted C$_1$-C$_6$ alkyl, preferably H;

U is —CR$^6$R$^7$—W, wherein R$^6$ and R$^7$ are independently selected from H and optionally substituted C$_1$-C$_6$ alkyl, preferably H; or R$^6$ and R$^7$ can form an optionally substituted C$_3$-C$_6$ cycloalkyl with the carbon they are attached to, preferably an optionally substituted C$_3$ or C$_4$ cycloalkyl;

V is (CR$^2$R$^3$)$_m$;

W is selected from optionally substituted aryl and optionally substituted divalent heteroaryl, preferably aryl;

Z is hydroxy;

m is an integer selected from 1, 2 and 3, preferably 3;

q is an integer selected from 1 and 2, preferably 1.

Preferred compounds of the invention include those of the following Formula XIII:

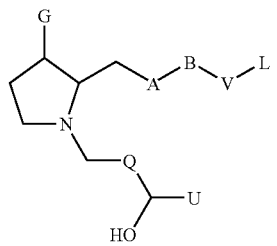

wherein Q, U, A, B, V, L and G are the same as defined in Formula IV above; and pharmaceutically acceptable salts thereof.

For at least some applications, particularly preferred compounds include those of the following Formula XIV:

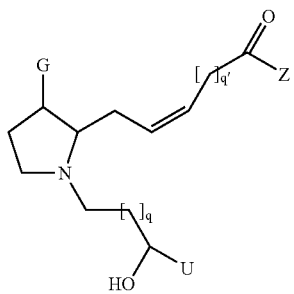

XIV wherein
q is an integer from 1-3;
q' is an integer from 2-4;
G is oxo, chloro, fluoro, methyl, methoxy;
Z is hydroxy, $C_{1-6}$alkoxy, amino or monoC$_{1-6}$alkylamino or diC$_{1-6}$alkylamino; and
U is —(CR$^2$R$^3$)$_s$—W, wherein R$^2$ and R$^3$ are independently the same as those substituents are defined in Formula IV above;
s is an integer from 0-6, preferably 2-6; W is hydrogen or $C_{3-7}$cycloalkyl; and
pharmaceutically acceptable salts thereof Also, for at least some applications, particularly preferred compounds include those of the following Formula XV:

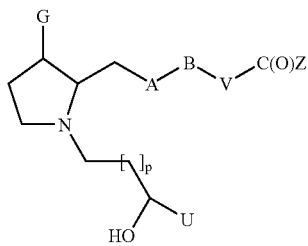

XV wherein
A is O, S or CH$_2$;
B is CH$_2$ or absent
V is divalent phenyl, divalent furan, or divalent thiophene;
p is an integer from 1-3;
G is oxo, chloro, fluoro, methyl, methoxy;
Z is hydroxy, $C_{1-6}$alkoxy, amino or monoC$_{1-6}$alkylamino or diC$_{1-6}$alkylamino;
U is —(CR$^2$R$^3$)$_s$—W, wherein R$^2$ and R$^3$ are independently the same as those substituents are defined in Formula IV above;
s is an integer from 0-6, preferably 2-6; and W is hydrogen or $C_{3-7}$cycloalkyl;
and pharmaceutically acceptable salts thereof.

The invention also includes compounds and use of optically active compounds of the above Formulae, particularly compounds of the above Formulae I through XV where a single stereoisomer of a chiral compound is present in an enaniomeric excess, e.g. where a single stereoisomer is present in an amount of at least 70 mole percent relative to other stereoisomer(s), more preferably where one stereoisomer is present in an amount of at least about 80, 85, 90, 92, 93, 94, 95, 96, 97, 98 or 99 mole percent relative to other stereosiomer(s).

Preferred compounds of the invention exhibit good binding activity in a standard prostaglandin EP2 and/or EP4 receptor binding assays. Such an assay is defined in Examples 22 and 24, which follows.

In an another aspect, the invention provides a coordinated administration regime of a substituted pyrrolidine compound with a distinct phosphodiesterase (PDE) inhibitor compound for simultaneous, sequential or separate use.

In a further aspect, the invention provides a coordinated administration regime of a substituted pyrrolidine compound with a distinct phosphodiesterase (PDE) inhibitor compound. A coordinated regime typically entails administration of a substituted pyrrolidine compound substantially simultaneously with a phosphodiesterase inhibitor compound (cocktail formulation), or where the distinct therapeutics are administered separately but within the same general time period, e.g. within the same 6, 12, 24, 48, 72, 96 or 120 hour period.

Without being bound by any theory, it is believed that such coordinated administration of a PDE inhibitor compound can provide increased cyclic GMP levels in a subject which can further enhance effects of the administered substituted pyrrolidine compound.

A variety of PDE inhibitor compounds may be employed. A specifically preferred pyrazolo[4,3-d]prymidin-7-one is sildenfil (Viagra™), also known as 5-[2-ethoxy-5-(4-methylpiperazin-1-ylsulphonyl)phenyl]-1-methyl-3-n-propyl-1,6-dihydro-7H-pyrazolo[4,3d]pyrimidin-7-one; as well as pharmaceutically acceptable salts thereof. Also preferred is zaprinast. Other preferred PDE inhibitors for use with the invention include, but are not limited to, particular bicyclic heterocylic PDE inhibitors, more preferably pyrazolo[4,3-d]prymidin-7-one is pryazolo[3,4-d]pyrimidin-4-ones, quinazolin-4-ones, purin-6-ones, pyrido[3,2-d]pyrimidin-4-ones; as well as pharmaceutically acceptable salts thereof.

Still further examples of particular phosphodiesterase (PDE) inhibitors have been previously reported in U.S. Pat. Nos. 6,100,270; 6,006,735; 6,143,757; 6,143,746; 6,140,329; 6,117,881; 6,043,252; 6,001,847; 5,981,527; and 6,207,829 B1; the disclosures of which patents are incorporated herein by reference. See also PCT/EP95/04065; WO-A-93/06104; WO-A-93/07149; WO-A-93/12095; WO-A-94/00453; EP 0 463756 B1; and WO-A-94/05661 for additional compounds. See also U.S. Pat. Nos. 4,753,945; 5,010,086; 6,121,279; 6,156,753; 6,054,475; 5,091,431; 6,127,363 and 6,040,309 for additional compounds useful as nucleic acid delivery agents in accordance with the invention. Additional PDE inhibitor compounds for use in accordance with the invention are disclosed in Komas et al., *Phosphodiesterase Inhibitors* (1996) (Schudt eds.), Academic Press, San Diego, Calif.

As discussed above, substituted pyrrolidine compounds of the invention are useful for treatment of diseases and disorders associated with the prostaglandin family of compounds.

In a yet further aspect, the invention use of a substituted pyrrolidine compound, including a compound of any one of Formulae I though XV for the preparation of a medicament for the treatment or prevention treatment of a mammal suffering from or susceptible to (prophylactic therapy) a disease or condition as disclosed herein including pre-term labor, dysmenorrhea, asthma and other conditions treated by bronchodilation, inflammation, hypertension, undesired blood-clotting and other undesired platelet activities, preeclampsia and/or eclampsia, and eosinphil-related disorders and other diseases and disorders associated with the prostaglandin EP2 and or EP4 receptor(s). Pyrrolidine compounds of the invention also are useful to treat a mammal suffering from or suspected of suffering from infertility, particularly a female suffering from infertility. Pyrrolidine compounds of the invention may be particularly beneficial for treatment of female mammals suffering from an ovulatory disorder. Additionally, pyrrolidine compounds of the invention can be administered to females undergoing reproductive treatments such as in-vitro, fertilization or implant procedures, e.g. to stimulate follicular development and maturation. Pyrrolidine compounds of the invention also are useful to treat sexual dysfunction, including erectile dysfunction.

Preferred pyrrolidine compounds of the invention also will be useful for treatment of undesired bone loss (e.g. osteoporosis, particularly in women) or otherwise promoting bone formation and treatment of other bone diseases such as Paget's disease.

Therapeutic methods of the invention in general comprise administering an effective amount of one or more substituted pyrrolidine compounds as disclosed herein to a mammal in need thereof As discussed above, in preferred aspects of the invention, a substituted pyrrolidine compound is administered in conjunction with one or more PDE inhibitor compounds.

In a further aspect, the invention provides a use of a substituted pyrrolidine compound, including a compound of any one of Formulae I through XV for the preparation of a medicament for the treatment or prevention (including prophylactic treatment) of a disease or condition as disclosed herein, including infertility, preterm labor, asthma, hypertension, sexual dysfunction, osteoporosis and other destructive bone disease or disorder, inflammation, and other diseases and disorders associated with prostaglandin. The invention also includes use of a substituted pyrrolidine compound in conjunction with one or more PDE inhibitor compounds for the treatment or prevention of such disease or condition as disclosed herein.

In a yet further aspect, the invention provides a use of a substituted pyrrolidine compound, including a compound of any one of Formulae I through XV for the preparation of a medicament for the treatment or prevention (including prophylactic treatment) of a disease or condition as disclosed herein, including infertility, preterm labor, asthma, hypertension, sexual dysfunction, osteoporosis and other destructive bone disease or disorder, inflammation, and other diseases and disorders associated with prostaglandin. The invention also includes use of a substituted pyrrolidine compound in conjunction with one or more PDE inhibitor compounds for simultaneous, sequential or separate use, for the preparation of a medicament for the treatment or prevention of such disease or condition as disclosed herein.

The invention also provides pharmaceutical compositions that comprise one or more substituted pyrrolidine compounds of the invention and a suitable carrier for the compositions, optionally formulated or packaged with one or more PDE inhibitor compounds. Other aspects of the invention are disclosed infra.

Other aspects of the invention are disclosed infra.

DETAILED DESCRIPTION OF THE INVENTION

We have now discovered that substituted pyrrolidine compounds, including compounds of the above Formulae I, II, III, IV, V, VI, VII, VIII, IX, X, XI, XII, XIII, XIV and XV are useful for treatment of a variety of disorders, particularly diseases and disorders associated with prostaglandin, such as by inhibiting prostanoid-induced smooth muscle contraction.

As discussed above, preferred compounds of the invention are substituted at both the 2 and 3-ring positions in addition to N-substitution, but are unsubstituted at the 4 and 5-positions of the pyrrolidine ring, such as compounds of the following Formulae IA, IIA and IIIA:

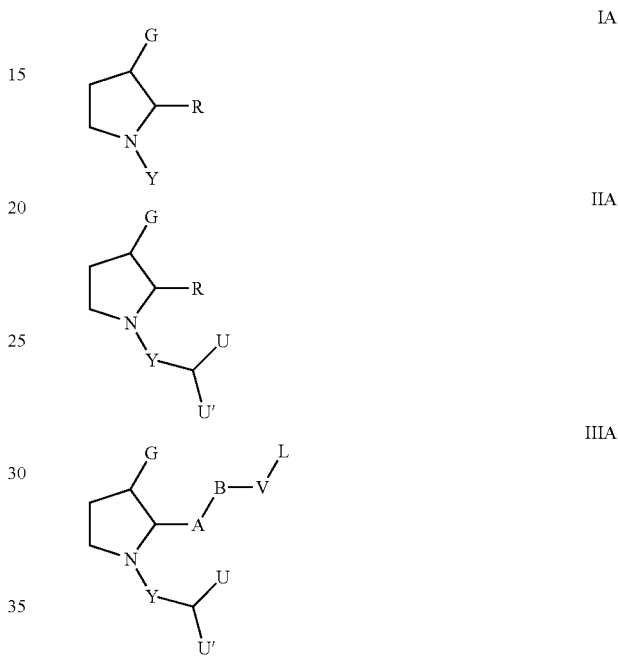

wherein the substituents G, R, Y, U, U', A, B, V and L are the same as defined in Formulae I through III above.

Suitable alkyl substituent groups of compounds of the invention (which includes compounds of Formulae I, IA, II, IIA, III, IIIA, IV, V, X, XIII, XIV and XV as those formulae are defined above) typically have from 1 to about 12 carbon atoms, more preferably 1 to about 8 carbon atoms, still more preferably 1, 2, 3, 4, 5, or 6 carbon atoms. As used herein, the term alkyl unless otherwise modified refers to both cyclic and noncyclic groups, although of course cyclic groups will comprise at least three carbon ring members. Preferred alkenyl and alkynyl groups of compounds of the invention have one or more unsaturated linkages and typically from 2 to about 12 carbon atoms, more preferably 2 to about 8 carbon atoms, still more preferably 2, 3, 4, 5, or 6 carbon atoms. The terms alkenyl and alkynyl as used herein refer to both cyclic and noncyclic groups, although straight or branched noncyclic groups are generally more preferred. Preferred alkoxy groups of compounds of the invention include groups having one or more oxygen linkages and from 1 to about 12 carbon atoms, more preferably from 1 to about 8 carbon atoms, and still more preferably 1, 2, 3, 4, 5 or 6 carbon atoms. Preferred alkylthio groups of compounds of the invention include those groups having one or more thioether linkages and from 1 to about 12 carbon atoms, more preferably from 1 to about 8 carbon atoms, and still more preferably 1, 2, 3, 4, 5, or 6 carbon atoms. Preferred alkylsulfinyl groups of compounds of the invention include those groups having one or more sulfoxide (SO) groups and from 1 to about 12 carbon atoms, more preferably from 1 to about 8 carbon atoms, and still more preferably 1, 2, 3, 4, 5, or 6 carbon atoms. Preferred alkylsulfonyl groups of compounds of the invention include those groups having one or more sulfonyl ($SO_2$) groups and from 1 to about 12 carbon atoms, more preferably from 1 to about 8 carbon atoms, and still more preferably 1, 2, 3, 4, 5 or 6 carbon atoms. Preferred aminoalkyl groups include those groups having one or more primary, secondary and/or tertiary amine groups, and from 1 to about 12 carbon atoms, more preferably 1 to about 8 carbon atoms, still more preferably 1, 2, 3, 4, 5, or 6 carbon atoms. Secondary and tertiary amine groups are generally more preferred than primary amine moieties. Suitable heteroaromatic groups of compounds of the invention contain one or more N, O or S atoms and include, e.g., coumarinyl including 8-coumarinyl, quinolinyl including 8-quinolinyl, pyridyl, pyrazinyl, pyrimidyl, furyl, pyrrolyl, thienyl, thiazolyl, oxazolyl, oxidizolyl, triazole, imidazolyl, indolyl, benzofuranyl and benzothiazole. Suitable heteroalicyclic groups of compounds of the invention contain one or more N, O or S atoms and include, e.g., tetrahydrofuranyl, thienyl, tetrahydropyranyl, piperidinyl, morpholino and pyrrolidinyl groups. Suitable carbocyclic aryl groups of compounds of the invention include single and multiple ring compounds, including multiple ring compounds that contain separate and/or fused aryl groups. Typical carbocyclic aryl groups of compounds of the invention contain 1 to 3 separate or fused rings and from 6 to about 18 carbon ring atoms. Specifically preferred carbocyclic aryl groups include phenyl; naphthyl including 1-naphthyl and 2-naphthyl; biphenyl; phenanthryl; anthracyl; and acenaphthyl. Substituted carbocyclic groups are particularly suitable including substituted phenyl, such as 2-substituted phenyl, 3-substituted phenyl, 4-substituted phenyl, 2,3-substituted phenyl, 2,4-substituted phenyl, and 2,5-substituted phenyl; and substituted naphthyl, including naphthyl substituted at the 5, 6 and/or 7 positions.

Suitable aralkyl groups of compounds of the invention include single and multiple ring compounds, including multiple ring compounds that contain separate and/or fused aryl groups. Typical aralkyl groups contain 1 to 3 separate or fused rings and from 6 to about 18 carbon ring atoms. Preferred aralkyl groups include benzyl and methylenenaphthyl (—$CH_2$-naphthyl), and other carbocyclic aralkyl groups, as discussed above.

Suitable heteroaralkyl groups of compounds of the invention include single and multiple ring compounds, including multiple ring compounds that contain separate and/or fused heteroaromatic groups, where such groups are substituted onto an alkyl linkage. More preferably, a heteroaralkyl group contains a heteroaromatic group that has 1 to 3 rings, 3 to 8 ring members in each ring and from 1 to 3 hetero N, O or S) atoms, substituted onto an alkyl linkage. Suitable heteroaromatic groups substituted onto an alkyl linkage include e.g., coumarinyl including 8-coumarinyl, quinolinyl including 8-quinolinyl, pyridyl, pyrazinyl, pyrimidyl, furyl, pyrrolyl, thienyl, thiazolyl, oxazolyl, oxidizolyl, triazole, imidazolyl, indolyl, benzofuranyl and benzothiazole.

Suitable heteroalicyclicalkyl groups of compounds of the invention include single and multiple ring compounds, where such groups are substituted onto an alkyl linkage. More preferably, a heteroalicylicalkyl group contains at least one ring that has 3 to 8 ring members from 1 to 3 hetero (N, O or S) atoms, substituted onto an alkyl linkage. Suitable heteroalicyclic groups substituted onto an alkyl linkage include e.g. tetrahydrofuranyl, thienyl, tetrahydropyranyl, piperidinyl, morpholino and pyrrolidinyl groups.

The term "$C_1$-$C_6$-alkyl" refers to monovalent branched or unbranched alkyl groups having 1 to 5 carbon atoms. This term is exemplified by groups such as methyl, ethyl, n-propyl, isopropyl, n-butyl, isobutyl, tert-butyl, n-hexyl and the like.

The term "$C_3$-$C_6$-cycloalkyl $C_1$-$C_6$-alkyl" refers to $C_1$-$C_6$-alkyl groups, as defined above, having saturated carbocyclic rings having 3 to 6 carbon atoms as substituent. Examples include ethyl cyclobutyl, cyclopropylmethyl cyclobutyl and the like.

The term "$C_3$-$C_6$-cycloalkyl" refers to saturated carbocyclic rings having 3 to 6 carbon atoms. Examples include cyclopropyl, cyclobutyl, cyclopentyl, cyclohexyl, cyclohexenyl and the like.

The term "Aryl" refers to aromatic carbocyclic groups of from 6 to 14 carbon atoms having a single ring (e.g. phenyl) or multiple condensed rings (e.g. naphthyl). Examples include phenyl, naphthyl, phenanthrenyl and the like.

The term "Heteroaryl" refers to a monocyclic heteroaromatic, or a bicyclic or a tricyclic fused-ring heteroaromatic group containing at least one heteroatom selected from S, N and O. Particular examples of heteroaromatic groups include optionally substituted pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, benzodioxolyl, quinolizinyl, quinazolinyl, pthalazinyl, quinoxalinyl, cinnnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetra-hydroisoquinolyl, purinyl, pteridinyl, carbazolyl, xanthenyl or benzoquinolyl.

The term "heteroalkyl" as used herein is inclusive of alkoxy, alkylthio, alkylamino, alkylsulfinyl and alkylsulfonyl. The term "heteroalkenyl" as used herein is inclusive of such alkoxy, alkylthio, alkylamino, alkylsulfinyl and alkylsulfonyl groups that further include one or more carbon-carbon double bonds, typically one or two carbon-carbon double bonds. The term "heteroalkynyl" as used herein is inclusive of such alkoxy, alkylthio, alkylamino, alkylsulfinyl and alkylsulfonyl groups that further include one or more carbon-carbon triple bonds, typically one or two carbon-carbon triple bonds.

As discussed above, various substituents of the above formulae, such as R, Y, G, $R^1$, $R^2$, $R^3$, $R^4$, $R^5$, U, U', A, B, V, L, Q, and Z may be optionally substituted. A "substituted" R, Y, G, $R^1$, $R^2$, $R^3$, $R^4$, $R^5$, U, U', A, B, V, L, Q, and Z group or other substituent may be substituted by other than hydrogen at one or more available positions, typically 1 to 3 or 4 positions, by one or more suitable groups such as those disclosed herein. Suitable groups that may be present on a "substituted" R, Y, G, $R^1$, $R^2$, $R^3$, $R^4$, $R^5$, U, U'A, B, V, L, Q, and Z group or other substituent include e.g. halogen such as fluoro, chloro, bromo and iodo; cyano; hydroxyl; nitro; azido; alkanoyl such as a $C_{1-6}$ alkanoyl group such as acyl and the like; carboxamido; alkyl groups including those groups having 1 to about 12 carbon atoms, or 1, 2, 3, 4, 5, or 6 carbon atoms; alkenyl and alkynyl groups including groups having one or more unsaturated linkages and from 2 to about 12 carbon, or 2, 3, 4, 5 or 6 carbon atoms; alkoxy groups including those having one or more oxygen linkages and from 1 to about 12 carbon atoms, or 1, 2, 3, 4, 5 or 6 carbon atoms; aryloxy such as phenoxy; alkylthio groups including those moieties having one or more thioether linkages and from 1 to about 12 carbon atoms, or 1, 2, 3, 4, 5 or 6 carbon atoms; alkylsulfinyl groups including those moieties having one or more sulfinyl linkages and from 1 to about 12 carbon atoms, or 1, 2, 3, 4, 5, or 6 carbon atoms; alkylsulfonyl groups including those moieties having one or more sulfonyl linkages and from 1 to about 12 carbon atoms, or 1, 2, 3, 4, 5, or 6 carbon atoms; aminoalkyl groups such as groups having one or more N atoms and from 1 to about 12 carbon atoms, or 1, 2, 3, 4, 5 or 6 carbon atoms; carbocyclic aryl having 6 or more carbons; aralkyl having 1 to 3 separate or fused rings and from 6 to about 18 carbon ring atoms, with benzyl being a preferred group; aralkoxy having 1 to 3 separate or fused rings and from 6 to about 18 carbon ring atoms, with O-benzyl being a preferred group; or a heteroaromatic or heteroalicyclic group having 1 to 3 separate or fused rings with 3 to about 8 members per ring and one or more N, O or S atoms, e.g. coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazolyl, tetrahydrofuranyl, tetrahydropyranyl, piperidinyl, morpholino and pyrrolidinyl.

It should be understood that alkoxy, alkylthio, alkylsulfinyl, alkylsulfonyl and aminoalkyl substituent groups described above include groups where a hetero atom is directly bonded to a ring system, such as a carbocyclic aryl group or heteroaromatic group or heteroalicyclic group including pyrrolidine group, as well as groups where a hetero atom of the group is spaced from such ring system by an alkylene linkage, e.g. of 1 to about 4 carbon atoms.

A particularly preferred embodiment of the invention is pyrrolidine derivatives according to formula VI wherein G is halogen, including Cl or F, preferably Cl; V is selected from optionally substituted divalent aryl and optionally substituted divalent heteroaryl, preferably aryl, more preferably phenyl; L is —C(O)OH; Q is $(CR^2R^3)_q$ wherein $R^2$ and $R^3$ are independently selected from H and optionally substituted $C_1$-$C_6$ alkyl, preferably H; q is an integer selected from 1 and 2; U is —$CR^6R^7$—W, wherein $R^6$ and $R^7$ are independently selected from H and optionally substituted $C_1$-$C_6$ alkyl, preferably H; or $R^6$ and $R^7$ can form an optionally substituted $C_3$-$C_6$ cycloalkyl with the carbon they are attached to, preferably an optionally substituted $C_3$ or $C_4$ cycloalkyl, more preferably cyclobutyl; W is selected from hydrogen, optionally substituted $C_1$-$C_6$ alkyl and optionally substituted $C_3$-$C_6$ cycloalkyl $C_1$-$C_6$ alkyl, preferably optionally substituted $C_1$-$C_6$ alkyl, more preferably butyl.

Another particularly preferred embodiment of the invention is pyrrolidine derivatives according to formula VII wherein G is halogen, including Cl or F, preferably Cl; B is $CH_2$ or absent; V is selected from optionally substituted divalent aryl and optionally substituted divalent heteroaryl, more preferably phenyl or furanyl; L is —C(O)OH; Q is $(CR^2R^3)_q$ wherein $R^2$ and $R^3$ are independently selected from H and optionally substituted $C_1$-$C_6$ alkyl, preferably H; q is an integer selected from 1 or 2, preferably 1; U is —$CR^6R^7$—W, wherein $R^6$ and $R^7$ are independently selected from H and optionally substituted $C_1$-$C_6$ alkyl, preferably H; or $R^6$ and $R^7$ can form an optionally substituted $C_3$-$C_6$ cycloalkyl with the carbon they are attached to, preferably an optionally substituted $C_3$ or $C_4$ cycloalkyl, more preferably cyclobutyl; W is selected from hydrogen, optionally substituted $C_1$-$C_6$ alkyl and optionally substituted $C_3$-$C_6$ cycloalkyl $C_1$-$C_6$ alkyl, preferably optionally substituted $C_1$-$C_6$ alkyl, more preferably butyl.

Another particularly preferred embodiment of the invention is pyrrolidine derivatives according to formula VIII wherein G is halogen, including Cl or F, preferably Cl; V is $(CR^2R^3)_m$, preferably $(CH_2)_m$; m is an integer selected from 1, 2 and 3, preferably 3; L is —C(O)OH; Q is $(CR^2R^3)_q$ wherein $R^2$ and $R^3$ are independently selected from H and optionally substituted $C_1$-$C_6$ alkyl, preferably H; q is an integer selected from 1 and 2, preferably 1; U is —$CR^6R^7$—W, wherein $R^6$ and $R^7$ are independently selected from H and optionally substituted $C_1$-$C_6$ alkyl, preferably H; or $R^6$ and $R^7$ can form an optionally substituted $C_3$-$C_6$ cycloalkyl with the carbon they are attached to, preferably an optionally substituted $C_3$ or $C_4$ cycloalkyl, more preferably cyclobutyl; W is selected from hydrogen, optionally substituted $C_1$-$C_6$ alkyl and optionally substituted $C_3$-$C_6$ cycloalkyl $C_1$-$C_6$ alkyl, preferably methyl cyclopropyl, ethyl, propyl and butyl.

Another particularly preferred embodiment of the invention is pyrrolidine derivatives according to formula IX wherein G is halogen, including Cl or F, preferably Cl; V is $(CR^2R^3)_m$, preferably $(CH_2)_m$; m is an integer selected from 1, 2 and 3, preferably 3; L is —C(O)OH; Q is $(CR^2R^3)_q$ wherein $R^2$ and $R^3$ are independently selected from H and optionally substituted $C_1$-$C_6$ alkyl, preferably H; q is an integer selected from 1 or 2, preferably 1; U is —$CR^6R^7$—W, wherein $R^6$ and $R^7$ are independently selected from H and optionally substituted $C_1$-$C_6$ alkyl, preferably H; or $R^6$ and $R^7$ can form a $C_2$-$C_6$ cycloalkyl with the carbon they are attached to, preferably an optionally substituted $C_3$ or $C_4$ cycloalkyl, more preferably cyclopropyl; W is selected from optionally substituted aryl and optionally substituted divalent heteroaryl, preferably aryl, more preferably optionally substituted phenyl, including 3-methyl phenyl and unsubsituted phenyl.

Another particularly preferred embodiment of the invention is pyrrolidine derivatives according to formula X' wherein G is oxo; A is $CH_2$; V is selected from $(CR^2R^3)_m$, optionally substituted aryl and optionally substituted heteroaryl, preferably $(CH_2)_m$; m is an integer selected from 1, 2, 3, 4, 5 and 6, preferably 3; L is —C(O)OH; Q is $(CR^2R^3)_q$ wherein $R^2$ and $R^3$ are independently selected from H and optionally substituted $C_1$-$C_6$ alkyl, preferably H; q is selected from 1 and 2, preferably 1; U is —$CR^6R^7$—W, wherein $R^6$ and $R^7$ form an optionally substituted $C_3$-$C_6$ cycloalkyl with the carbon they are attached to, preferably an optionally substituted $C_3$ or $C_4$ cycloalkyl, more preferably cyclopropyl; W is selected from hydrogen, optionally substituted $C_1$-$C_6$ alkyl, optionally substituted $C_3$-$C_6$ cycloalkyl $C_1$-$C_6$ alkyl, preferably methyl cyclopropyl;

Another particularly preferred embodiment of the invention is pyrrolidine derivatives according to formula XI wherein G is oxo; V is $(CR^2R^3)_m$, preferably $(CH_2)_m$; m is an integer selected from 1, 2 and 3, preferably 3; L is —C(O)OH; Q is $(CR^2R^3)_q$ wherein $R^2$ and $R^3$ are independently selected from H and optionally substituted $C_1$-$C_6$ alkyl, preferably H; q is selected from 1 and 2, preferably 1; U is —$CR^6R^7$—W, wherein $R^6$ and $R^7$ are independently selected from H and optionally substituted $C_1$-$C_6$ alkyl, preferably H; or $R^6$ and $R^7$ can form an optionally substituted $C_3$-$C_6$ cycloalkyl with the carbon they are attached to, preferably an optionally substituted $C_3$ or $C_4$ cycloalkyl, more preferably cyclopropyl; W is selected from hydrogen, optionally substituted $C_1$-$C_6$ alkyl, optionally substituted $C_3$-$C_6$ cycloalkyl $C_1$-$C_6$ alkyl, optionally substituted $C_3$-$C_6$ cycloalkyl, preferably $C_3$-$C_6$ cycloalkyl $C_1$-$C_6$ alkyl, more preferably methyl cyclopropyl;

Another particularly preferred embodiment of the invention is pyrrolidine derivatives according to formula XII wherein G is oxo; V is $(CR^2R^3)_m$, preferably $(CH_2)_m$; m is an integer selected from 1, 2 and 3, preferably 3; L is —C(O)OH; Q is $(CR^2R^3)_q$ wherein $R^2$ and $R^3$ are independently selected from H and optionally substituted $C_1$-$C_6$ alkyl, preferably H; q is an integer selected from 1 and 2, preferably 1; U is —$CR^6R^7$—W, wherein $R^6$ and $R^7$ are independently selected from H and optionally substituted $C_1$-$C_6$ alkyl, preferably H; or $R^6$ and $R^7$ can form an optionally substituted $C_3$-$C_6$ cycloalkyl with the carbon they are attached to, preferably an optionally substituted $C_3$ or $C_4$ cycloalkyl, more preferably cyclopropyl; W is selected from optionally substituted aryl and optionally substituted divalent heteroaryl, preferably aryl, more preferably optionally substituted phenyl, including 3-methyl phenyl and unsubsituted phenyl;

Specifically preferred substituted pyrrolidine compounds of the invention include the following depicted compounds, and pharmaceutically acceptable salts of these compounds.

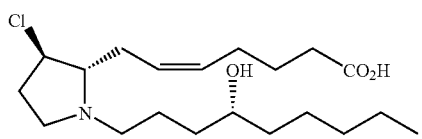

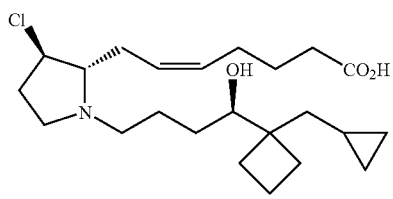

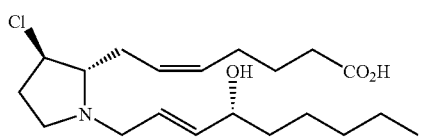

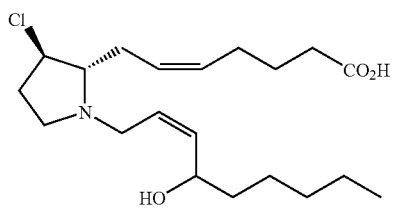

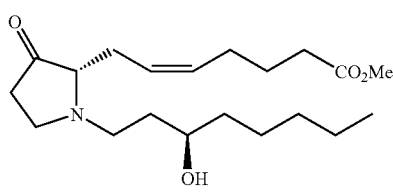

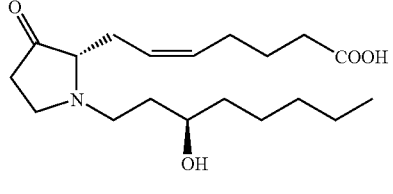

-continued

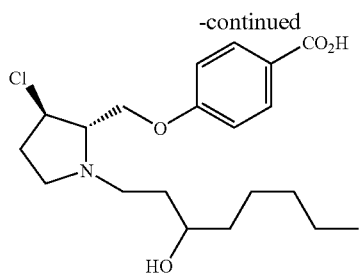

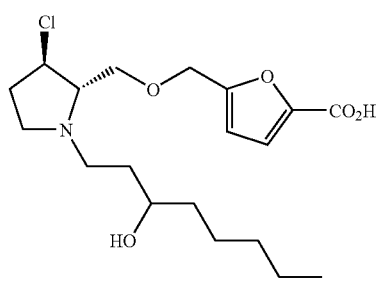

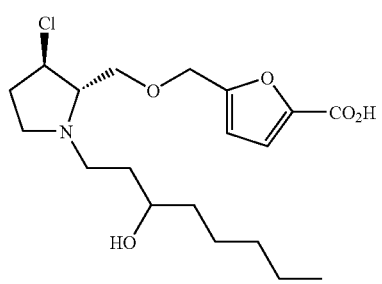

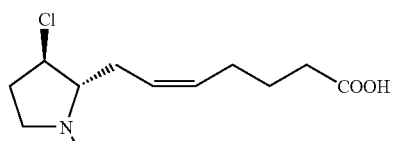

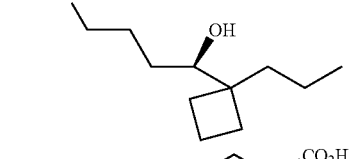

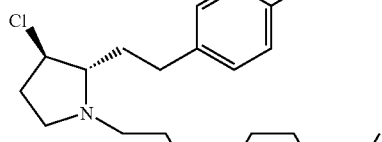

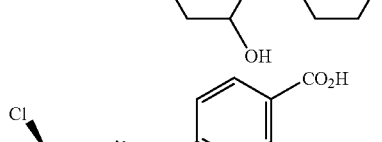

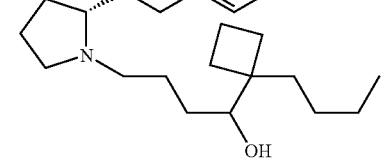

As discussed above, preferred compounds of the invention exhibit good activity in a standard prostaglandin EP2 and or EP4 receptor binding assay. References herein to "standard prostaglandin EP2 receptor binding assay" are intended to refer to the protocol as defined in Example 22, which follows. References herein to "standard prostaglandin EP2 receptor binding assay" are intended to refer to the protocol as defined in Example 24, which follows.

Generally preferred compounds of the invention have a Ki (μM) of about 100 or less, more preferably about 50 or less, still more preferably a Ki (μM) of about 10 or 20 or less, even more preferably a Ki (μM) of about 5 or less in such a defined standard prostaglandin assay as exemplified by Examples 22 and 24 which follow.

Abbreviations

The following abbreviations are hereinafter used in the accompanying examples:

min (minute), hr (hour), g (gram), mmol (millimole), ml (milliliter), μl (microliters), ACN (acetonitrile), DCM (dichloromethane), DMAP (4-dimethylamino-pyridine), DMSO (dimethyl sulfoxide), EtOAc (ethyl acetate), LDA (Lithium diisopropylamide), RT (room temperature), TBAF (Tetrabutylammonium fluoride), TFA (trifluoro-acetic acid), THF (tetrahydrofuran), TLC (Thin Layer Chromatography).

Synthesis of Compounds of the Invention:

Pyrrolidine compounds of the invention can be readily prepared from readily available starting materials using the following general methods and procedures.

Suitable synthetic procedures are exemplified in the following illustrative Schemes 1, 2, 3 and 4. It should be appreciated that the compounds shown in the following Schemes are exemplary only, and a variety of other compounds can be employed in a similar manner as described below. For instance, pyrrolidine compounds having non-hydrogen substituents at 4 and 5 ring positions can be provided using a starting reagent having such substitution. It will also be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used. Such conditions can be determined by the person skilled in the art, using routine optimisation procedures.

General Protocol:

Referring now to Scheme 1 below, hydrogenation of the pyrrolidine intermediate i (which was prepared according to the procedure of Macdonald et al: J. Med. Chem. 1998, 41(21), 3919-3922) followed by reaction with di-tert-butyl dicarbonate can give the desired pyrrolidine derivatives ii bearing the Boc group on the nitrogen of the pyrrolidine ring. Reduction of the methyl ester group e.g. using Red-Al in a suitable solvent such as benzene or other aromatic solvent preferably at elevated temperature can provide alcohol intermediate iii typically in high yield. Oxidation of the alcohol such as by Swern methodology can give corresponding aldehyde which can be further functionalized e.g. by Wittig reaction as shown in Scheme 1 using (4-carboxybutyl)triphenylphosphonium bromide and KotBu or other suitable base. The acid intermediate can be esterified such as by treatment with trimethylsylildiazomethane to provide ester intermediate iv.

The silyl protecting group may be suitably removed with fluoride ion, e.g. using TBAF in a suitable solvent such as THF to provide alcohol v which in turn can be oxidized such as by Swern methodology. The ketone intermediate is then suitably protected as ketal e.g. using trimethyl orthoformate and $H_2SO_4$ in MeOH. Those reactions conditions also provided N-deprotection was also accomplished and the intermediate vi was obtained in good yield. The compound may be resolved by suitable means including fractional crystallization using appropriate optically active reagents such as D-tartaric acid and i-PrOH. Chiral chromatography also could be employed.

For the preparation of the 16-hydroxy pyrrolidine derivatives, the chiral amine intermediate vii can undergo Michael's reaction with the desired 2,3 unsaturated ketone to provide the product intermediate viii typically in quite high yields. Reduction of the ketone (e.g. Luche's reduction) followed by hydrolysis preferably under acidic conditions can provide pyrrolidine derivative ix.

Preparation of pyrrolidine compounds bearing the hydroxyl group in position 17 can be obtained by reductive amination reaction of the pyrrolidine intermediate vii with the appropriate aldehyde and $NaCNBH_3$ in MeOH. Treatment of the intermediate x with HCl 4M in dioxane can result in deprotection of both ketal and O-silyl groups. Saponification of the ester xi gave the desired acid xii in good yields. Example 5 below particularly exemplifies this general approach.

For the preparation of the saturated derivatives xiv, the ester intermediate of general formula xi was hydrogenated at 1 atm using Pd/C in MeOH (Step N). Saponification of the ester xiii using NaOH gave the correspondent acid xiv in good yield. Example 19 below particularly exemplifies this general approach.

Scheme 1

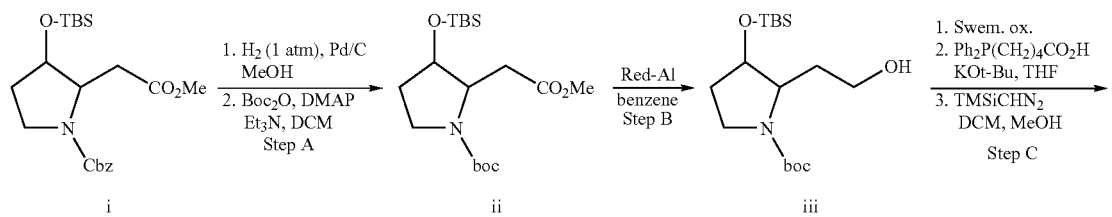

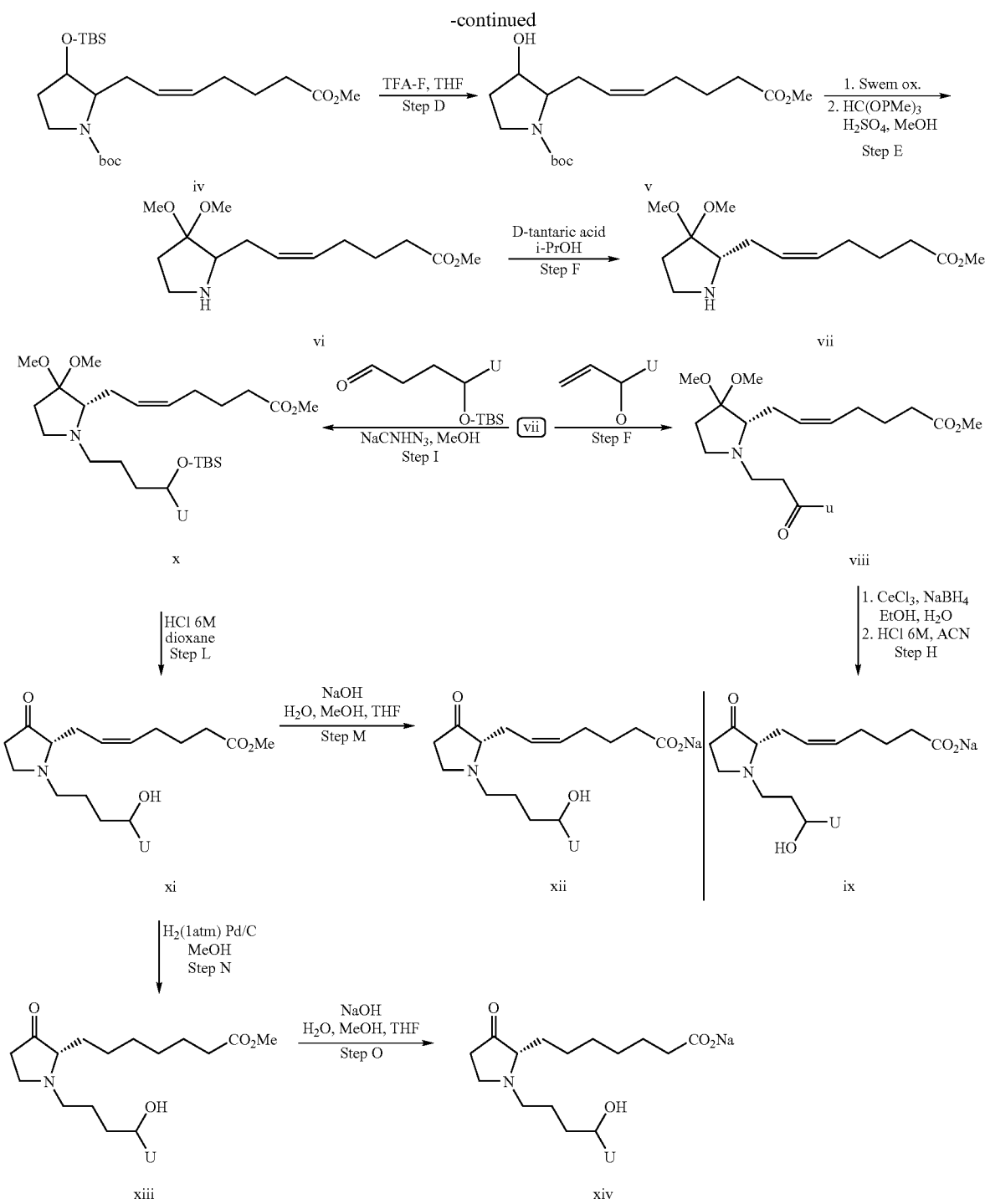

Referring now to Scheme 2 below, alcohol i (suitably obtained as described in Scheme 1 above, intermediate v) can be activated such as by forming a sulfonyl ester, e.g. by reaction with tosyl chloride in the presence of pyridine or other base to afford the tosylate intermediate ii. That 3-position of the pyrrolidine ring can be then further fictionalized as desired by nucleophilic substitution such as by treatment with tetrabutylammonium chloride in toluene or other suitable solvent to provide the depicted 3-chloro pyrrolidine compound. Acid deprotection using HCl in dioxane can provide pyrrolidine intermediate iii. Preparation of the further 16-hydroxy or 17-hydroxy pyrrolidine compounds can be accomplished as described with respect to Scheme 1 (steps G, H and I, L, M, respectively) above using the pyrrolidine derivative iii. Example 1 below particularly exemplifies this general approach of Scheme 2.

Preparation of compounds having the double bond in position 14 (prostaglandin numbering) can be obtained by N-alkylation of the pyrrolidine intermediate iii with the desired allyl bromide derivatives. Deprotection of the alcohol using standard acidic condition followed by saponification reaction (step E and F respectively) afford the desired product xii. Example 3 below particularly exemplifies this general approach of Scheme 2.
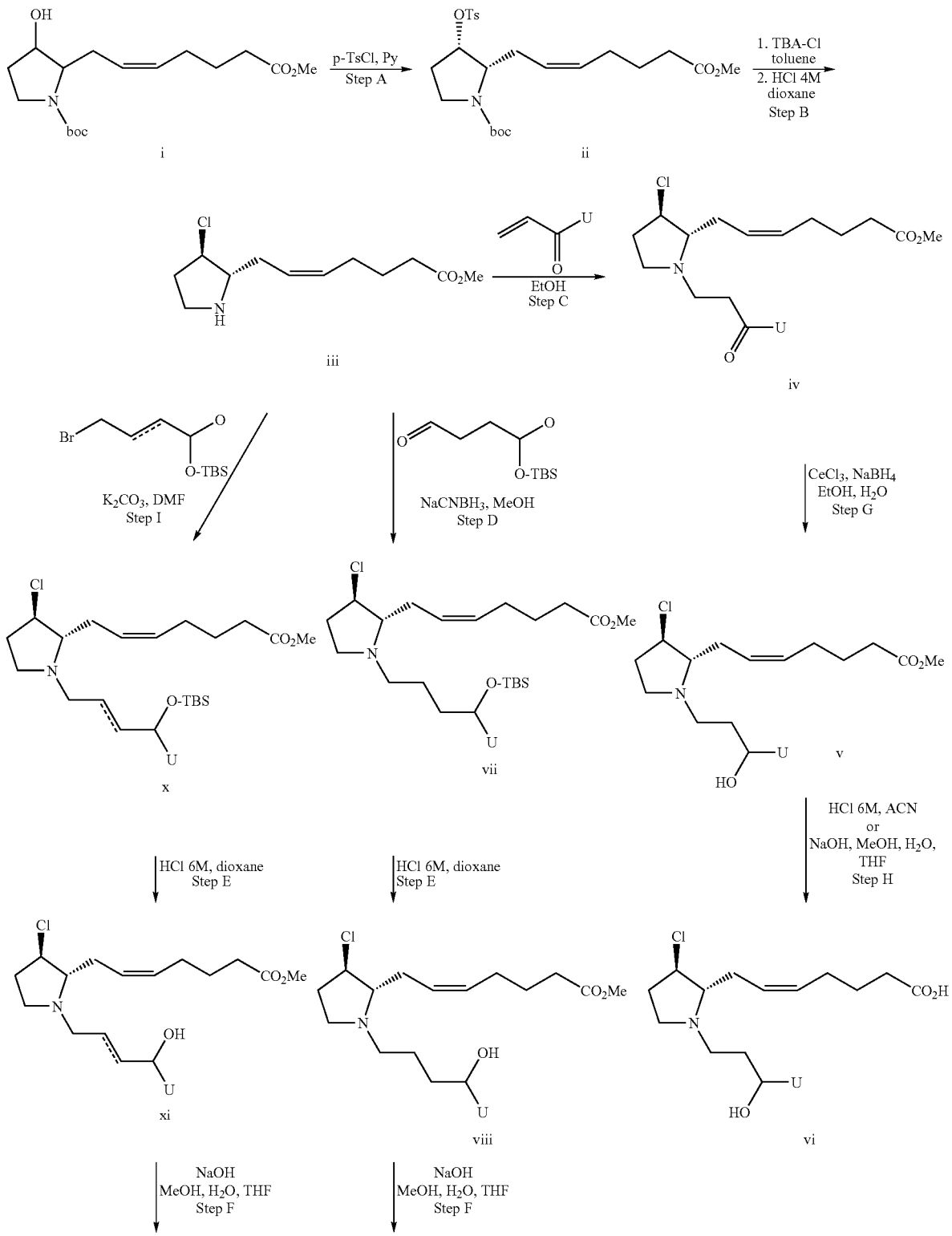
Scheme 2

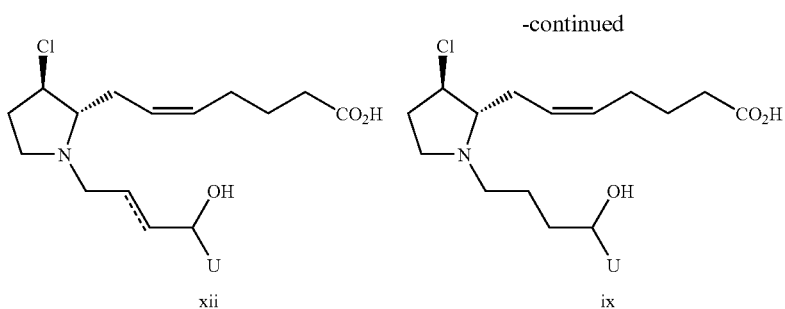

Referring now to Scheme 3 below, reduction of the pyrrolidine intermediate ii (which was prepared from GlyOEt according to the procedure described in *J. Chem. Soc. Perkin Trans.* 1, 1993, 1313-1317) e.g. with L-selectride can give the depicted cis alcohol derivative iii. The same reduction can also be carried out with baker's yeast to afford the desired chiral cis alcohol iii. The 3-positon of the pyrrolidine ring can be substituted to provide a variety of groups, e.g. oxidized to provide an oxo (>C=O) ring atom, or the ring carbon can be substituted through a nucleophilic displacement. Thus, as shown in Scheme 3, the alcohol iii can be tosylated followed by reaction with tetrabutylammonium chloride can provide the 3-chloro pyrrolidine derivative iv. Reduction of the ester group using NaBH$_4$ in THF/MeOH (9/1) gave the alcohol intermediate v.

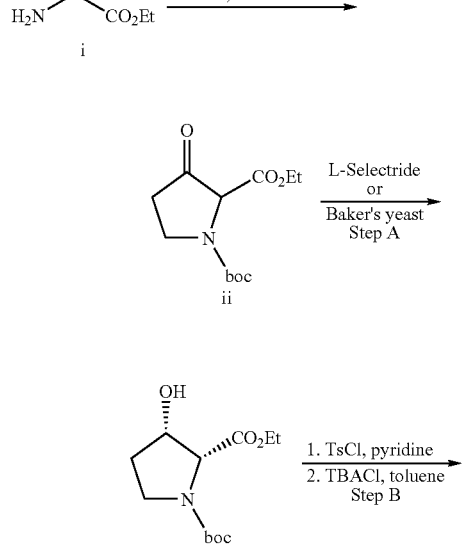

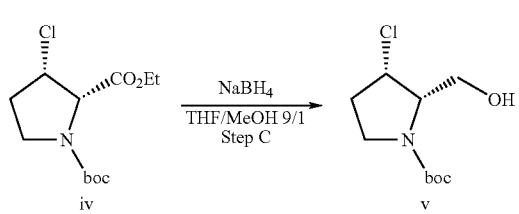

-continued

Mitsunobu Reaction

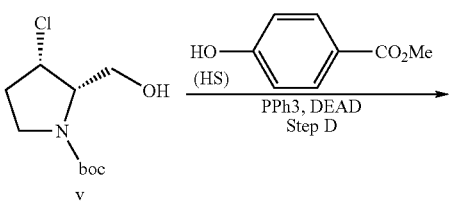

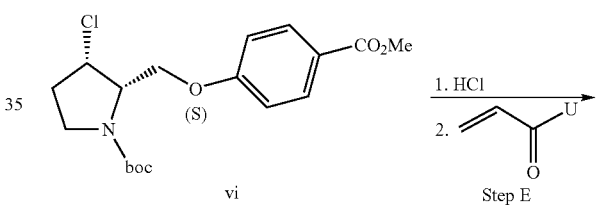

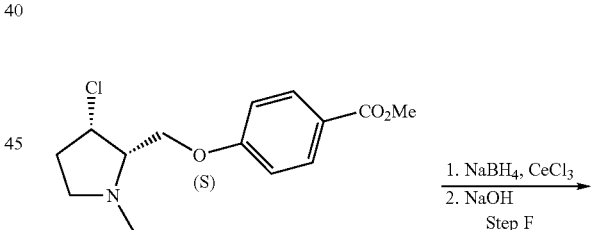

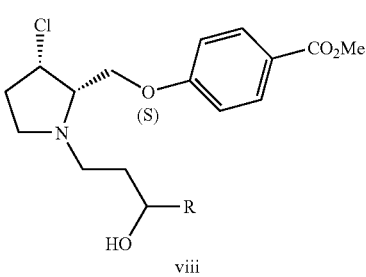

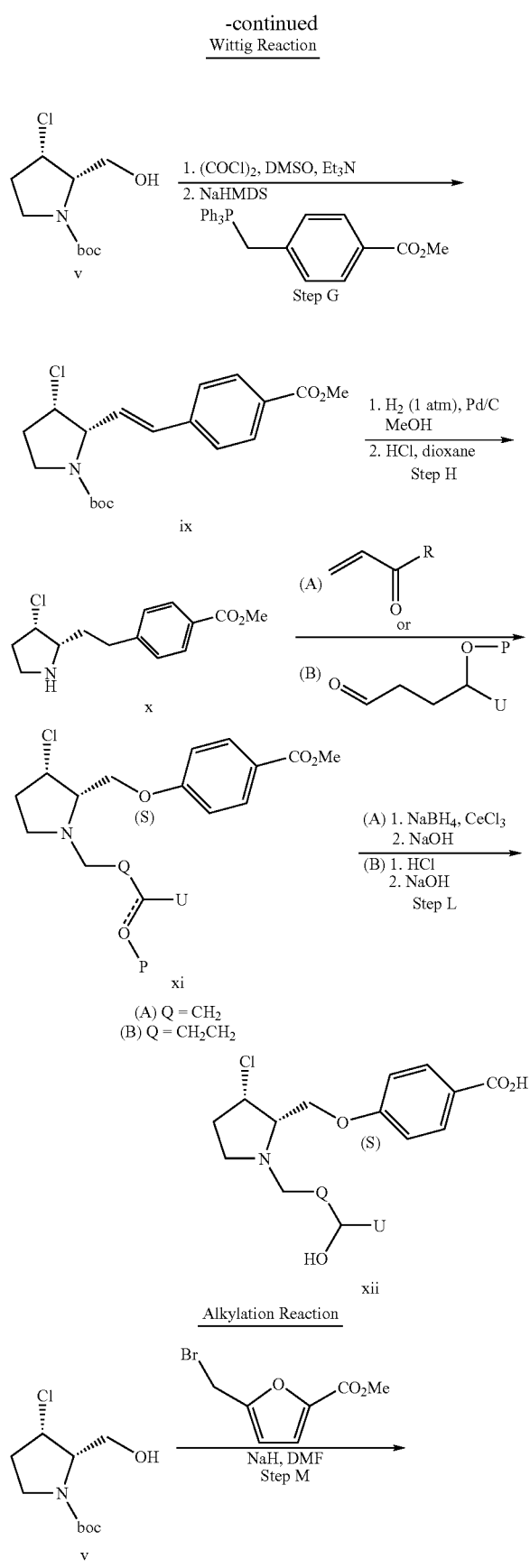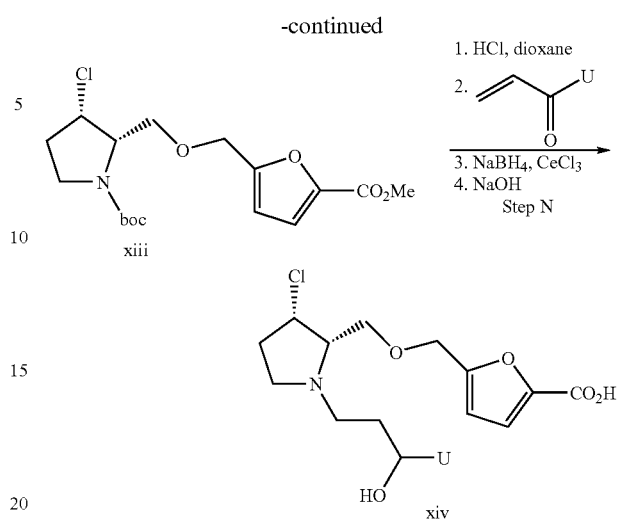

Preparation of the corresponding phenyl ether derivatives (viii) was obtained via Mitsunobu reaction between the alcohol v and the appropriate phenol derivatives. The ethers or thioethers derivative vi then can be converted to the corresponding 16-hydroxy or 17-hydroxy pyrrolidine compounds as generally described with respect to Scheme 1.

Synthesis of the phenethyl derivatives of general formula xii can be obtained by Wittig reaction between the aldehyde intermediate obtained e.g. by Swern oxidation of the alcohol v and the desired phosphorane derivatives. Catalytic hydrogenation followed by acid deprotection can provide the pyrrolidine intermediate x. Synthesis of the corresponding 16-hydroxy and 17-hydroxy pyrrolidine compounds can be obtained as described above with respect to Scheme 1.

Preparation of the furyl ether derivatives of general formula xiv can be obtained by alkylation of the alcohol v with the appropriate bromide using a strong base such as NaH in DMF. The intermediate xiii then can be converted to the desired pyrrolidine derivatives using protocols described above.

Examples 6-8 below particularly exemplify this general approach of Scheme 3.

Referring now to Scheme 4 below, which shows a preferred route to compounds of Formula IX and XII above, a deprotection reaction of the pyrrolidine intermediate (which can be prepared according to the procedure of Macdonald et al: *J. Med. Chem.* 1998, 41(21), 3919-3922) followed by reaction with di-tert-butyl dicarbonate gives the desired pyrrolidine derivatives bearing the Boc group on the nitrogen of the pyrrolidine ring (ii).

Reduction of the methyl ester group using Red-Al in suitable solvent such as an aromatic solvent e.g. benzene at reflux or other elevated temperature can provide alcohol intermediate iii in almost quantitative yield. Oxidation of the alcohol moiety e.g. using the traditional Swern methodology can provide the corresponding aldehyde that can be used in a Wittig reaction with (4-carboxybutyl)triphenylphosphonium bromide and suitable base such as KOtBu. The free acid intermediate is suitably protected in situ e.g. as methyl ester using tri-methylsylildiazomethane to lead to intermediate iv. Removal of the silyl group using fluoride such TBAF in THF can give the alcohol v that is oxidized e.g. using the Swern methodology, followed by protecting the ketone intermediate e.g. as a ketal using trimethyl orthoformate and H₂SO₄ in MeOH. Under such reaction conditions, N-deprotection also can result thereby providing intermediate vi. The racemic mixture can be resolved, e.g. by fractional crystallization using D-tartaric acid in i-PrOH. Intermediate vii can undergo Michael addition with suitable electrophile such as the depicted 2,3-unsaturated ketone to provide the ketone intermediate viii in almost quantitative yield. Luche reduction of the ketone followed by acid hydrolysis can provide in good yield the desired pyrrolidine derivatives ix.

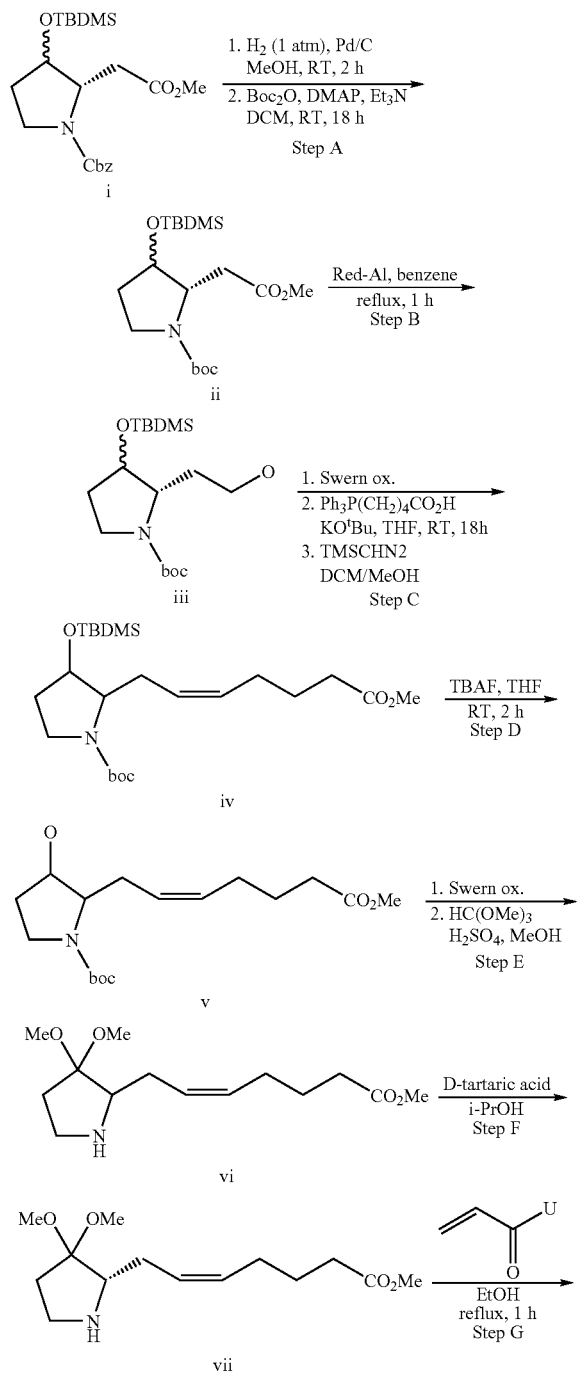

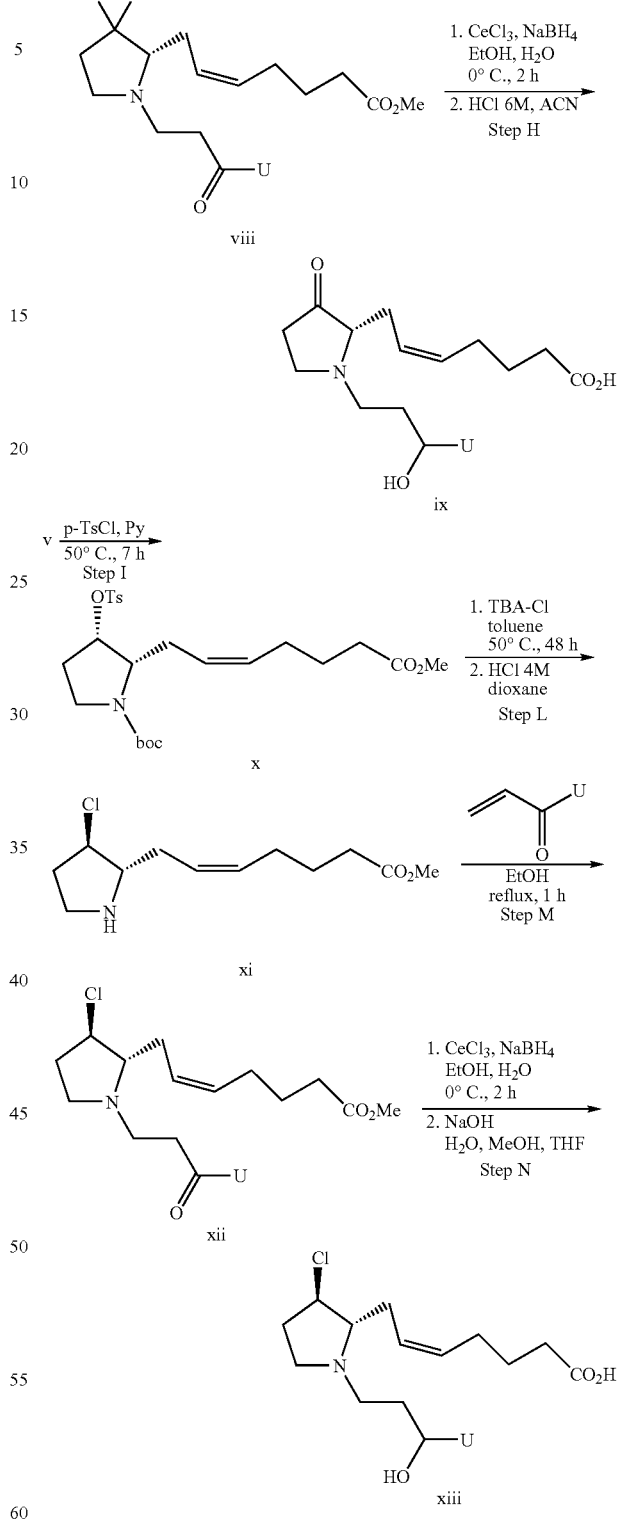

Preparation of the depicted 3-chloro pyrrolidine derivatives can be accomplished starting from the alcohol intermediate v. Replacement of the alcohol function with chloro can be obtained in a two-step procedure via activation of intermdiate x e.g. the preparation of the tosylate intermediate x. Displacement of the tosyl group can be accomplished using tetrabutylammonium chloride in toluene at 50-60° C. Deprotection of the nitrogen atom using HCl in dioxane can give in quantitative yield the desired intermediate xi. Michael reaction with the desired unsaturated ketone can yield xii in good yield. Luche's reduction followed by saponification of the methyl ester intermediate can provide the desired pyrrolidine derivatives xiii. Examples 12 through 14 below particularly exemplify this general approach.

Additional preferred syntheses of compounds of the invention are detailed in the examples which follow.

As discussed above, a preferred aspect of the invention includes coordinated administration of a substituted pyrrolidine compound, such as a compound of any one of Formulae I through XV, with one or more PDE inhibitor compounds.

In addition to the PDE inhibitor compounds discussed above, suitable PDE inhibitor compounds for use in the methods and compositions of the invention are disclosed below, including compounds of the following Formulae XVI to XXIII, which are generally preferred for use with the present invention. It should be appreciated however that the present invention is not limited by any particular PDE inhibitor compound, and the invention is applicable to any such PDE inhibitor compound now known or subsequently discovered or developed. As discussed below, in addition to the PDE inhibitor compounds specifically identified herein, suitable PDE inhibitor compounds also may be identified by simple testing.

In general, PDE-5 inhibitor compounds are preferred for use in the methods and compositions of the invention.

More specifically, in one invention embodiment, at least one of the administered compounds is a bicyclic heterocyclic PDE inhibitor such as described in the U.S. Pat. No. 6,100,270, preferably at least one of the following pyrazolo[4,3-d]prymidin-7-ones, pryazolo[3,4-d]pyrimidin4-ones, a quinazolin-4-ones, a purin-6-ones, or pyrido[3,2-d]pyrimidin-4-ones set forth in the following Formulae I-V including pharmaceutically acceptable salts thereof.

Suitable PDE inhibitor compounds include those of the following Formula XVI:

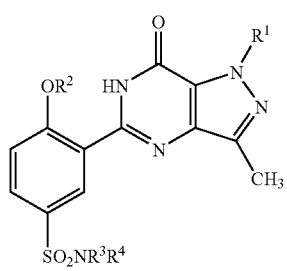

(XVI)

wherein in Formula XVI, $R^1$ is methyl or ethyl; $R^2$ is ethyl or n-propyl; and $R^3$ and $R^4$ are each independently H, or $C_1$-$C_6$ alkyl optionally substituted with $C_5$-$C_7$ cycloalkyl or with morpholino; and pharmaceutically acceptable salts thereof.

Suitable PDE inhibitor compounds also include those of the following Formula XVII:

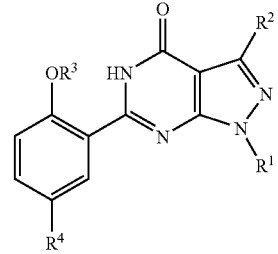

(XVII)

wherein in Formula IX is $C_1$-$C_6$ alkyl; $R^2$ is H; methyl or ethyl;

$R^3$ is $C_2$-$C_4$ alkyl;

$R^4$ is H; $C_1$-$C_4$ alkyl optionally substituted with $NR^5R^6$, CN, $CONR^5R^6$ or $CO_2R^7$; $C_2$-$C_4$ alkenyl optionally substituted with CN, $CONR^5$, $R^6$ or $CO_2R^7$; $C_2$-$C_4$ alkanoyl optionally substituted with NR $R^6$; $SO_2$ $NR^5R^6$; $CONR^5$, $R^6$; $CO_2R^7$ or halo;

$R^5$ and $R^6$ are each independently H or $C_1$-$C_4$ alkyl; or, together with the nitrogen atom to which they are attached, form a pyrrolidino, piperidino, morpholino, 4-($NR^8$)-1-piperazinyl or 1-imidazolyl group wherein said group is optionally substituted with one or two $C_1$-$C_4$ alkyl groups;

$R^7$ is H or $C_1$-$C_4$ alkyl;

and $R^8$ is H; $C_1$-$C_3$ alkyl or (hydroxy)$C_2$-$C_3$ alkyl; and pharmaceutically salts thereof.

Additional suitable PDE inhibitor compounds include those of the following Formula (XVI):

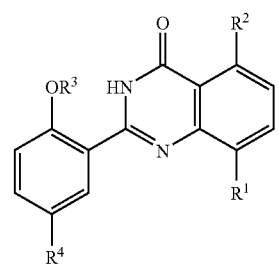

(XVIII)

wherein in Formula XVIII $R^1$ is H; $C_1$-$C_4$ alkyl; $C_1$-$C_4$ alkoxy or $CONR^5$, $R^6$;

$R^2$ is H or $C_1$-$C_4$ alkyl;

$R^3$ is $C_2$-$C_4$ alkyl;

$R^4$ is H; $C_2$-$C_4$ alkanoyl optionally substituted with $NR^7R^8$; (hydroxy)$C_2$-$C_4$ alkyl optionally substituted with $NR^7R^8$; CH=CHCO$_2R^9$; CH=CHCONR$^7$, $R^8$; CH$_2$ CH$_2$ CO$_2R^9$; CH$_2$CH$_2$ CONR$^7R^1$; SO$_2$ NR$^7R^8$; SO$_2$ NH(CH$_2$)$_n$NR$^7R^8$ or imidazolyl;

$R^5$ and $R^6$ are each independently H or $C_1$-$C_4$ alkyl;

$R^7$ and $R^8$ are each independently H or $C_1$-$C_4$ alkyl; or, together with the nitrogen atom to which they are attached, form a pyrrolidino, piperidino, morpholino or 4-($NR^{10}$)-1-piperazinyl group wherein any of said groups is optionally substituted with $CONR^5R^6$;

$R^9$ is H or $C_1$-$C_4$ alkyl;

$R^{10}$ is H; $C_1$-$C_3$ alkyl or (hydroxy)$C_2$-$C_3$ alkyl;

and n is 2, 3 or 4;

preferably with the proviso that $R^4$ is not H when $R^1$ is H, $C_1$-$C_4$ alkyl or $C_1$-$C_4$ alkoxy; and pharmaceutically acceptable salts thereof.

Suitable PDE inhibitor compounds include those of the following Formula XIX:

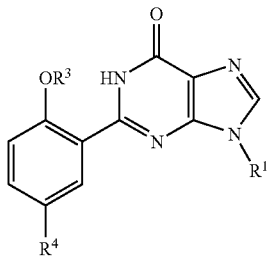

(XIX)

wherein in Formula XIX $R^1$ is $C_1$-$C_4$ alkyl; $R^2$ is $C_2$-$C_4$ alkyl;

$R^3$ is H or $SO_2 NR^4R^5$;

$R^4$ and $R^5$ together with the nitrogen atom to which they are attached form a pyrrolidino, piperidino, morpholino or 4-($NR^6$)-1-piperazinyl group;

and $R^6$ is H or $C_1$-$C_3$ alkyl; and pharmaceutically acceptable salts thereof.

Additional suitable PDE inhibitor compounds include those of the following Formula (XX):

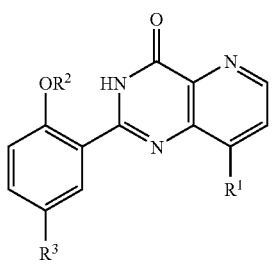

(XX)

wherein in Formula XX $R^1$ is H; $C_1$-$C_4$ alkyl; CN or $CONR^4R^5$; $R^2$ is $C_2$-$C_4$ alkyl;

$R^3$ is $SO_2 NR^6R^7$; $NO_2$; $NH_2$; $NHCOR^8$; $NHSO_2R^8$ or $N(SO_2R^8)_2$;

$R^4$ and $R^5$ are each independently selected from H and $C_1$-$C_4$ alkyl;

$R^6$ and $R^7$ are each independently selected from H and $C_1$-$C_4$ alkyl optionally substituted with $CO_2R^9$, OH, pyridyl, 5-isoxazolin-3-onyl, morpholino or 1-imidazolidin-2-onyl; or, together with the nitrogen atom to which they are attached, form a pyrrolidino, piperidino, morpholino, 1-pyrazolyl or ($NR^{10}$)-1-piperazinyl group wherein any of said groups may optionally be substituted with one or two substituents selected from $C_1$-$C_4$ alkyl, $CO_2R^9$, $NH_2$ and OH;

$R^8$ is $C_1$-$C_4$ alkyl or pyridyl;

$R^9$ is H or $C_1$-$C_4$ alkyl;

and $R^{10}$ is H; $C_1$-$C_4$ alkyl or (hydroxy)$C_2$-$C_3$ alkyl; and a pharmaceutically acceptable salt thereof.

A preferred group of compounds of Formula XVI above include those wherein:

$R^3$ is H; methyl or ethyl;

$R^4$ is $C_1$-$C_6$ alkyl optionally substituted with cyclohexyl or with morpholino; and pharmaceutically acceptable salts thereof.

Preferred compounds of Formula XVII above include those wherein $R^1$ is n-propyl; $R^2$ is H or methyl; $R^3$ is ethyl or n-propyl; $R^4$ is H; ethyl substituted with $CONR^5R^6$ or $CO_2R^7$; vinyl substituted with $CONR^5R^6$ or $CO_2R^7$; acetyl substituted with $NR^5R^6$; $SO_2NR^5R^6$; $CONR^5R^6$; $CO_2R^7$ or bromo; $R^5$ and $R^6$ together with the nitrogen atom to which they are attached form a morpholino, 4-($NR^8$)-1-piperazinyl or 2,4-dimethyl-1-imidazolyl group; $R^7$ is H or t-butyl; and $R^8$ is methyl or 2-hydroxyethyl; and pharmaceutically acceptable salts thereof.

Preferred compounds of Formula XVIII above include those where $R^1$ is H; methyl; methoxy or $CONR^5R^6$; $R^2$ is H or methyl; $R^3$ is ethyl or n-propyl; $R^4$ is H; acetyl optionally substituted with $NR^7R^8$; hydroxyethyl substituted with $NR^7R^8$; CH=$CHCO_2R^9$; CH=$CHCONR^7R^8$; $CH_2$ $CH_2$ $CO_2R^9$; $SO_2NR^7R^8$; $SO_2NH(CH_2)_3NR^7R^8$ or 1-imidazolyl; $R^5$ and $R^6$ are each independently H or ethyl; $R^7$ and $R^8$ together with the nitrogen atom to which they are attached form a piperidino, 4-carbamoylpiperidino, morpholino or 4-($NR^{10}$)-1-piperazinyl group; $R^9$ is H or t-butyl; and $R^{10}$ is H; methyl or 2-hydroxyethyl; and pharmaceutically acceptable salts thereof.

Preferred compounds of Formula XIX above include those wherein $R^1$ and $R^2$ are each independently ethyl or n-propyl; $R^4$ and $R^5$ together with the nitrogen atom to which they are attached form a 4-($NR^6$)-1-piperazinyl group; and $R^3$ and $R^6$ are as previously defined for Formula XI; and pharmaceutically acceptable salts thereof.

Preferred compounds of Formula XX above include compounds wherein $R^1$ is H; n-propyl; CN or $CONH_2$; $R^2$ is ethyl; $R^3$ is $SO_2NR^6R^7$; $NO_2$; $NH_2$; $NHCOCH(CH_3)_2$; $NHSO_2CH(CH_3)_2$; $NHSO_2$(3-pyridyl) or $N[SO_2$(3-pyridyl)]$_2$; $R^6$ is H; methyl or 2-hydroxyethyl; $R^7$ is methyl optionally substituted with 2-pyridyl or 5-isoxazolin-3-onyl; or ethyl 2-substituted with OH, $CO_2$ $CH_2$ $CH_3$, morpholino or 1-imidazolidin-2-onyl; or $R^6$ and $R^7$ together with the nitrogen atom to which they are attached form a (4-$CO_2R^9$)piperidino, 5-amino-3-hydroxy-1-pyrazolyl or 4-($NR^{10}$)-1-piperazinyl group; $R^9$ is H or ethyl; and $R^{10}$ is H; methyl or 2-hydroxyethyl.

In another aspect, at least one of the administered PDE inhibitor compounds is a tetracyclic cGMP specific PDE inhibitor such as those described in U.S. Pat. No. 6,143,746 and as set forth in the following Formulae XXI-XXIII including pharmaceutically acceptable salts thereof.

Mores specifically, suitable compounds include those of the following Formula XXI:

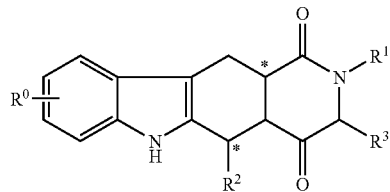

(XXI)

wherein in Formula XXI R⁰ represents hydrogen, halogen, or $C_{1-6}$ alkyl;

R¹ represents hydrogen, $C_{1-6}$ alkyl, $C_{2-6}$ alkenyl, $C_{2-6}$ alkynyl, halo$C_{1-6}$ alkyl, $C_{3-8}$ cycloalkyl, $C_{3-8}$ cycloalkyl$C_{1-3}$ alkyl, aryl$C_{1-3}$ alkyl, or heteroaryl$C_{1-3}$ alkyl;

R² represents an optionally substituted monocyclic aromatic ring selected from benzene, thiophene, furan, and pyridine, or an optionally substituted bicyclic ring;

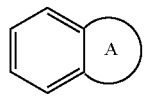

attached to the rest of the molecule via one of the benzene ring carbon atoms and wherein the fused ring A is a 5- or 6-membered ring which may be saturated or partially or fully unsaturated and comprises carbon atoms and optionally one or two heteroatoms selected from oxygen, sulphur, and nitrogen; and R³ represents hydrogen of $C_{1-3}$ alkyl, or R¹ and R³ together represent a 3- or 4-membered alkyl or alkenyl chain; and pharmaceutically and salts and solvates (e.g., hydrates) thereof.

Suitable compounds also include those of the following Formula XXII:

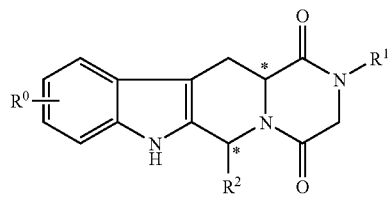

(XXII)

wherein in Formula XXII R⁰ represents hydrogen, halogen, or $C_{1-6}$ alkyl;

R¹ represents hydrogen, Clue alkyl, halo$C_{1-6}$ alkyl, $C_{3-8}$ cycloalkyl$C_{1-3}$ alkyl, aryl$C_{1-3}$ alkyl, or heteroaryl$C_{1-3}$ alkyl; and R² represents an optionally substituted monocyclic aromatic ring selected from benzene, thiophene, furan, and pyridine, or an optionally substituted bicyclic ring

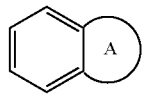

attached to the rest of the molecule via one of the benzene ring carbon atoms, and wherein the fused ring A is a 5- or 6-membered ring which can be saturated or partially or fully unsaturated and comprises carbon atoms and optionally one or two heteroatoms selected from oxygen, sulphur, and nitrogen; and pharmaceutically acceptable salts and solvates (e.g., hydrates) thereof.

A further subgroup of compounds of Formula XXI preferred for use in the methods of the invention, are compounds of the following Formula XXIII:

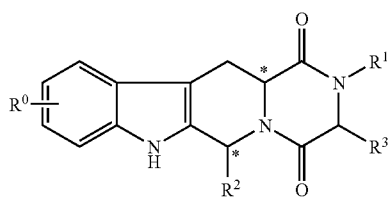

(XXIII)

wherein in Formula XXIII:

R⁰ represents hydrogen, halogen, or $C_{1-6}$ alkyl;

R¹ represents hydrogen or $C_{1-6}$ alkyl;

R² represents the bicyclic ring

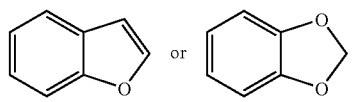

which can be optionally substituted by one or more groups selected from halogen and $C_{1-3}$ alkyl; and R³ represents hydrogen or $C_{1-3}$ alkyl; and pharmaceutically acceptable salts and solvates (e.g., hydrates) thereof.

In Formula XXII above, with respect to R¹, the term "aryl" as part of an aryl$C_{1-3}$ alkyl group means phenyl or phenyl substituted by one or more (e.g., 1, 2, or 3) substituents selected from halogen, $C_{1-6}$ alkyl, $C_{1-6}$ alkoxy, and methylenedioxy. The term "heteroaryl" as part of a heteroaryl$C_{1-3}$ alkyl group means thienyl, furyl, or pyridyl, each optionally substituted by one or more (e.g., 1, 2, or 3) substituents selected from halogen, $C_{1-6}$ alkyl, and $C_{1-6}$ alkoxy. The term "$C_{3-8}$ cycloalkyl" as a group or part of a $C_{3-8}$ cycloalkyl$C_{1-3}$ alkyl group means a monocyclic ring comprising three to eight carbon atoms. Examples of suitable cycloalkyl rings include the $C_{3-6}$ cycloalkyl rings cyclopropyl, cyclobutyl, cyclopentyl, and cyclohexyl.

In Formula XXII above, with respect to R², optional benzene ring substituents are selected from one or more (e.g., 1, 2, or 3) atoms or groups comprising halogen, hydroxy, $C_{1-6}$ alkyl, $C_{1-6}$ alkoxy, $CO_2R^b$, halo$C_{1-6}$ alkyl, halo$C_{1-6}$ alkoxy, cyano, nitro, and $NR^aR^b$, where $R^a$ and $R^b$ are each hydrogen or $C_{1-6}$ alkyl, or $R^a$ also can represent $C_{2-7}$ alkanoyl or $C_{1-6}$ alkylsulphonyl. Optional substituents for the remaining ring systems are selected from one or more (e.g., 1, 2, or 3 atoms or groups comprising halogen, $C_{1-6}$ alkyl, $C_{1-6}$ alkoxy, and aryl$C_{1-3}$ alkyl as defined above. The bicyclic ring

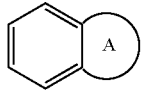

can, for example, represent naphthalene, a heterocycle such as benzoxazole, benzothiazole, benzisoxazole, benzimidazole, quinoline, indole, benzothiophene, benzofuran, or

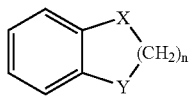

wherein n is an integer 1 or 2 and X and Y each can represent $CH_2$, O, S, or NH.

An administered PDE inhibitor compound also may be a carboline derivative or N-cinnamoyl derivative or (β) carbolines as described in the U.S. Pat. Nos. 6,043,252 and 6,117,881.

Particular PDE inhibitors compounds include the following:

cis-2,3,6,7,12,12a-hexahydro-2-(4-pyridyl-methyl)-6-(3,4-methylenedioxyphenyl)-pyrazino[2',1';6,1]-pyrido[3,4-b]indole-1,4-dione;

cis-2,3,6,7,12,12a-hexahydro-6-(2,3-dihydrobenzo[b]furan-5-yl)-2-methylpyrazino[2',1';6,1]-pyrido[3,4-b]indole-1,4-dione;

cis-2,3,6,7,12,12a-hexahydro-6-(5-bromo-2-thienyl)-2-methylpyrazino[2',1';6, 1]pyrido[3,4-b]indole-1,4-dione;

cis-2,3,6,7,12,12a-hexahydro-2-butyl-6-(4-methylphenyl)-pyrazino[2',1';6,1]pyrido[3,4-b]indole-1,4-dione;

(6R,12aR)-2,3,6,7,12,12a-hexahydro-2-isopropyl-6-(3,4-methylenedioxyphenyl)-pyrazino[2',1';6,1]pyrido-[3,4-b]indole-1,4-dione;

(6R,12aR)-2,3,6,7,12,12a-hexahydro-2-cyclopentyl-6-(3,4-methylenedioxyphenyl)-pyrazino[2',1';6,1]-pyrido[3,4-b]indole-1,4-dione;

(6R,12aR)-2,3,6,7,12,12a-hexahydro-2-cyclopropylmethyl-6-(4-methoxyphenyl)-pyrazino[2',1';6,1]-pyrido[3,4-b]indole-1,4-dione;

(6R,12aR)-2,3,6,7,12,12a-hexahydro-6-(3-chloro-4-methoxyphenyl)-2-methyl-pyrazino[2',1';6,1]pyrido[3,4-b]indole-1,4-dione;

(6R,12aR)-2,3,6,7,12,12a-hexahydro-2-methyl-6-(3,4-methylenedioxyphenyl)-pyrazino[2',1';6,1]pyrido[3,4-b]indole-1,4-dione;

(6R,12aR)-2,3,6,7,12,12a-hexahydro-6-(3,4-methylenedioxyphenyl)-pyrazino[2',1';6,1]pyrido[3,4-b]indole-1,4-dione;

(5aR, 12R, 14aS)-1,2,3,5,6,11,12,14a-octahydro-12-(3,4-methylenedioxyphenyl)-pyrrolo[1",2":4'5']-pyrazino[2',1';6, 1]pyrido[3,4-b]indole-5-1,4-dione;

(6R,12aR)-2,3,6,7,12,12a-hexahydro-6-(5-benzofuranyl)-2-methyl-pyrazino[2',1';6,1]pyrido[3,4-b]indole-1,4-dione;

(6R,12aR)-2,3,6,7,12,12a-hexahydro-6-(5-benzofuranyl)-pyrazino[2',1';6,1]pyrido[3,4-b]indole-1,4-dione;

(3S, 6R, 12aR)-2,3,6,7,12,12a-hexahydro-6-(5-benzofuranyl)-3-methyl-pyrazino[2',1'; 6,1]pyrido[3,4-b]indole-1, 4-dione;

(3S, 6R, 12aR)-2,3,6,7,12,12a-hexahydro-6-(5-benzofuranyl)-2,3-dimethyl-pyrazino[2',1',6,1]pyrido[3,4-b]indole-1,4-dione;

(6R,12aR)-2,3,6,7,12,12a-hexahydro-6-6-(5-benzofuranyl)-2-isopropyl-pyrazino[2',1',6,1]pyrido[3,4-b]indole-1,4-dione;

cis-2,3,6,7,12,12a-hexahydro-2-(4-pyridylmethyl)-6-(3,4-methylenedioxyphenyl)-pyrazino[2',1':6,1]pyrido[3,4-b]indole-1,4-dione;

cis-2,3,6,7,12,12-hexahydro-6-(2,3-dihydrobenzo[b]furan-5-yl)-2-methyl-pyrazino[2',1':6,1]pyrido[3,4-b]indole-1,4-dione;

cis-2,3,6,7,12,12a-hexahydro-6-(5-bromo-2-thienyl)-2-methyl-pyrazino[2',1':6,1]pyrido[3,4-b]indole-1,4-dione;

cis-2,3,6,7,12,12a-hexahydro-2-butyl-6-(4-methylphenyl)-pyrazino[2',1':6,1]pyrido[3,4-b]indole-1,4-dione;

(6R,12aR)-2,3,6,7,12,12a-Hexahydro-2-isopropyl-6-(3,4-methylenedioxyphenyl)-pyrazino[2',1':6,1]pyrido[3,4-b]indole-1,4-dione;

(6R,12aR)-2,3,6,7,12,12a-Hexahydro-2-cyclopentyl-6-(3,4-methylenedioxyphenyl)-pyrazino[2',1':6,1]pyrido[3,4-b]indole-1,4-dione;

(6R,12aR)-2,3,6,7,12,12a-Hexahydro-2-cyclopropylmethyl-6-(4-methoxyphenyl)-pyrazino[2',1':6,1]pyrido[3,4-b]indole-1,4-dione;

(6R,12aR)-2,3,6,7,12,12a-Hexahydro-6-(3-chloro-4-methoxyphenyl)-2-methyl-pyrazino[2',1':6,1]pyrido[3,4-b]indole-1,4-dione;

(6R,12aR)-2,3,6,7,12,12a-Hexahydro-2-methyl-6-(3,4-methylenedioxyphenyl)-pyrazino[2',1':6,1]pyrido[3,4-b]indole-1,4-dione;

(6R,12aR)-2,3,6,7,12,12a-Hexahydro-6-(3,4-methylenedioxyphenyl)-pyrazino[2',1':6,1]pyrido[3,4-b]indole-1,4-dione;

(5aR, 12R,14aS)-1,2,3,5,6,11,12,14a-Octahydro-12-(3,4-methylenedioxyphenyl)-pyrrolo[1",2":4',5']pyrazino[2',1':6, 1]pyrido[3,4-b]indole-5-1,4-dione;

cis-2,3,6,7,12,12a-hexahydro-2-cyclopropyl-6-(3,4-methylenedioxyphenyl)-pyrazino[2',1':6,1]pyrido[3,4-b]indole-1,4-dione;

(3S, 6R,12aR)-2,3,6,7,12,12a-hexahydro-3-methyl-6-(3,4-methylenedioxyphenyl)-pyrazino[2',1':6,1]pyrido[3,4-b]indole-1,4-dione;

(6R,12aR)-2,3,6,7,12,12a-hexahydro-2-methyl-6-(3,4-methylenedioxyphenyl)-pyrazino[2',1':6,1]pyrido[3,4-b]indole-1,4-dione;

(3S, 6R,12aR)-2,3,6,7,12,12a-hexahydro-2,3-dimethyl-6-(3,4-methylenedioxyphenyl)-pyrazino[2',1':6,1]pyrido[3,4-b]indole-1,4-dione;

(E)-1-(1-Phenyl-9,3,4,9-tetrahydro-β-carbolin-2-yl)-3-phenylpropene-1-one;

(E)-1-(1-Phenyl-1,3,4,9-tetrahydro-β-carbolin-2-yl)-3-(4-nitrophenyl)propene-1-one;

(E)-1-(1-Phenyl-1,3,4,9-tetrahydro-β-carbolin-2-yl)-3-(4-trifluoromethylphenyl)propene-1-one;

(E)-1-(1-Phenyl-1,3,4,9-tetrahydro-β-carbolin-2-yl)-3-(4-methoxyphenyl)propene-1-one;

(E)-1-[1-(4-Methoxyphenyl)-1,3,4,9-tetrahydro-β-carbolin-2-yl]-3-(4-trifluoromethylphenyl) propene-1-one;

(E)-N-[4-[3-Oxo-3-(1-phenyl-1,3,4,9-tetrahydro-β-carbolin-2-yl)propenyl]phenyl]acetamide;

(E)-1-[1-(4-Methoxyphenyl)-1,3,4,9-tetrahydro-β-carbolin-2-yl]-3-phenylpropene-1-one;

(E)-1-[1-(3,4-Methylenedioxyphenyl)-1,3,4,9-tetrahydro-β-carbolin-2-yl]-3-phenylpropene-1-one;

(E)-1-(1-Phenyl-1,3,4,9-tetrahydro-β-carbolin-2-yl)-3-(4-formylphenyl) propene-1-one;

(E)-N-[4-[3-Oxo-3-(1-(4-nitrophenyl)-1,3,4,9-tetrahydro-β-carbolin-2-yl)propenyl]phenyl]acetamide;

(E)-1-[1-(4-Nitrophenyl)-1,3,4,9-tetrahydro-β-carbolin-2-yl]-3-phenylpropene-1-one;

(E)-1-[1-(4-Trifluoromethoxyphenyl)-1,3,4,9-tetrahydro-β-carbolin-2-yl]-3-phenylpropene-1-one;

(E)-1-[1-(4-Methylphenyl)-1,3,4,9-tetrahydro-β-carbolin-2-yl]-3-phenyl propene-1-one;

(E)-N-[4-[3-Oxo-3-(1-(3,4-methylenedioxyphenyl)-1,3,4,9-tetrahydro-β-carbolin-2-yl)-propenyl]phenyl]acetamide;

(E)-4-[3-Oxo-3-(1-phenyl-1,3,4,9-tetrahydro-β-carbolin-2-yl)-propenyl]benzoic acid, methyl ester;

(E)-1-[1-(2-Chlorophenyl)-1,3,4,9-tetrahydro-β-carbolin-2-yl]-3-phenylpropene-1-one;

(E)-1-(1-Phenyl-1,3,4,9-tetrahydro-β-carbolin-2-yl)-3-(3,4-methylenedioxyphenyl)-propene-1-one;

(E)-N-[1-(3,4-Methylenedioxyphenyl)-1,3,4,9-tetrahydro-β-carbolin-2-yl]-3-(4-bromophenyl)-propene-1-one;

(E)-1-[1-(4-Chlorophenyl)-1,3,4,9-tetrahydro-β-carbolin-2-yl]-3-phenylpropene-1-one;

(E)-1-[1-(3,4-Methylenedioxyphenyl)-1,3,4,9-tetrahydro-β-carbolin-2-yl]-3-(4-ethoxyphenyl)propene-1-one;

(E)-4-[3-Oxo-3-(1-(3,4-methylenedioxyphenyl)-1,3,4,9-tetrahydro-β-carbolin-2-yl)propenyl]acetic acid, phenyl ester;

(E)-1-[1-(3,4-Methylenedioxyphenyl)-1,3,4,9-tetrahydro-β-carbolin-2-yl]-3-(4-hydroxyphenyl)propene-1-one;

(E)-1-[1-(3,4-Methylenedioxyphenyl)-1,3,4,9-tetrahydro-β-carbolin-2-yl]-3-(4-formylphenyl)propene-1-one;

(E)-1-[4-[3-Oxo-3-(1-(3,4-methylenedioxyphenyl)-1,3,4,9-tetrahydro-β-carbolin-2-yl)-propenyl]phenyl]-3-phenylurea;

(E)-1-[1-(3,4-Methylenedioxyphenyl)-1,3,4,9-tetrahydro-β-carbolin-2-yl]-3-(4-aminophenyl)-propene-1-one;

(E)-1-[1-(3,4-Methylenedioxy-phenyl)-1,3,4,9-tetrahydro-β-carbolin-2-yl]-3-(4-nitrophenyl)-propene-1-one;

(E)-1-[1-(3,4-Methylenedioxyphenyl)-1,3,4,9-tetrahydro-β-carbolin-2-yl]-3-[(4-bis(methylsulfonyl)-aminophenyl]-propene-1-one;

(E)-4-[3-Oxo-3-[1-(3,4-methylenedioxyphenyl)-1,3,4,9-tetrahydro-β-carbolin-2-yl]-propenyl]benzoic acid, methyl ester;

(E)-N-[4-[3-Oxo-3-[1-(3,4-methylenedioxyphenyl)-1,3,4,9-tetrahydro-β-carbolin-2-yl]propenyl]phenyl]methanesulfonamide;

(E)-4-[3-Oxo-3-[1-(3,4-methylenedioxyphenyl)-1,3,4,9-tetrahydro-β-carbolin-2-yl]propenyl]benzamide];

(E)-4-[3-Oxo-3-[1-(3,4-methylenedioxyphenyl)-1,3,4,9-tetrahydro-β-carbolin-2-yl]-propenyl]benzoic acid;

(E)-1-[1-(3,4-Methylenedioxyphenyl)-1,3,4,9-tetrahydro-β-carbolin-2-yl]-3-(4-cyanophenyl)propene-1-one;

(E)-1-[1-(3,4-Methylenedioxyphenyl)-1,3,4,9-tetrahydro-(3-carbolin-2-yl)-3-(4-trifluoromethylphenyl)propene-1-one;

(E)-1-[1-(3,4-Methylenedioxyphenyl)-1,3,4,9-tetrahydro-β-carbolin-2-yl]-3-(3,4-methylenedioxyphenyl)propene-1-one;

(E)-1-[1-(3,4-Methylenedioxyphenyl)-1,3,4,9-tetrahydro-β-carbolin-2-yl]-3-(4-chlorophenyl)-propene-1-one;

(E)-1-[1-(3,4-Methylenedioxyphenyl)-1,3,4,9-tetrahydro-β-carbolin-2-yl]-3-(4-trifluoromethoxyphenyl)propene-1-one;

(E)-1-[1-(3,4-Methylenedioxyphenyl)-1,3,4,9-tetrahydro-β-carbolin-2-yl]-3-(4-methylphenyl)propene-1-one;

(E)-[4-[3-Oxo-3-(1-(3,4-methylenedioxyphenyl)-1,3,4,9-tetrahydro-β-carbolin-2-yl)propenyl]phenyl]urea;

(E)-1-[1-(3,4-Methylenedioxyphenyl)-1,3,4,9-tetrahydro-β-carbolin-2-yl]-3-(4-hydroxymethylphenyl)propene-1-one;

(E)-N-Benzyl-4-[3-oxo-3-(1-(3,4-methylenedioxyphenyl)-1,3,4,9-tetrahydro-beta.-carbolin-2-yl)propenyl]benzamide;

(E)-1-[1-(3,4-Methylenedioxyphenyl)-1,3,4,9-tetrahydro-β-carbolin-2-yl]-3-(2,4-dichlorophenyl)propene-1-one;

(E)-1-[1-(3,4-Methylenedioxyphenyl)-1,3,4,9-tetrahydro-β-carbolin-2-yl]-3-(3-methoxy-4-hydroxyphenyl)propene-1-one;

(E)-1-[1-(3,4-Methylenedioxyphenyl)-1,3,4,9-tetrahydro-β-carbolin-2-yl]-3-(3-hydroxy-4-methoxyphenyl)propene-1-one;

(E)-1-[1-(3,4-Methylenedioxyphenyl)-1,3,4,9-tetrahydro-β-carbolin-2-yl]-3-(4-fluorophenyl)-propene-1-one;

(E)-1-[1-(3,4-Methylenedioxyphenyl)-1,3,4,9-tetrahydro-β-carbolin-2-yl]-3-indan-5-yl-1-propene-1-one;

(E)-N-[4-[3-Oxo-3-(1-(3,4-methylenedioxyphenyl)-1,3,4,9-tetrahydro-β-carbolin-2-yl)propenyl]benzoyl]benzenesulfonamide;

(E)-1-[1-(3,4-Methylenedioxyphenyl)-1,3,4,9-tetrahydro-β-carbolin-2-yl]-3-(3,4-dichlorophenyl)propene-1-one;

(E)-1-[1-(3,4-Methylenedioxyphenyl)-1,3,4,9-tetrahydro-β-carbolin-2-yl]-3-(3,4-dimethoxyphenol)propene-1-one;

(E)-1-[1-(3,4-Methylenedioxyphenyl)-1,3,4,9-tetrahydro-β-carbolin-2-yl]-3-(3,4-dihydroxyphenyl)propene-1-one;

(E)-N-Methyl-N-[4-[3-oxo-3-(1-(3,4-methylenedioxyphenyl)-1,3,4,9-tetrahydro-β-carbolin-2-yl)propenyl]phenyl]acetamide;

(E)-2,2-Dimethyl-N-[4-[3-Oxo-3-(1-(3,4-methylenedioxyphenyl)-1,3,4,9-tetrahydro-β-carbolin-2-yl)propenyl]phenyl]propionamide;

(E)-1-[1-(3,4-Methylenedioxyphenyl)-1,3,4,9-tetrahydro-β-carbolin-2-yl]-3-(3,5-dimethoxyphenyl)propene-1-one;

(E)-(N)-{4-[3-[1-(3,4-Methylenedioxyphenyl)-6-fluoro-1,3,4,9-tetrahydro-beta-carbolin-2-yl]-3-oxopropenyl]-phenyl}-acetamide;

(E)-1-[1-(3,4-Methylenedioxyphenyl)-1,3,4,9-tetrahydro-β-carbolin-2-yl]-3-(3,4,5-trimethoxyphenyl)propene-1-one;

(E)-N-[4-[3-Oxo-3-(1-(3,4-methylenedioxyphenyl)-1,3,4,9-tetrahydro-β-carbolin-2-yl)propenyl]phenyl]isobutyramide;

(E)-1-[1-(3,4-Methylenedioxyphenyl)-6-fluoro-1,3,4,9-tetrahydro-β-carbolin-2-yl]-3-phenylpropene-1-one;

(E)-N-(2-Methoxyethyl)-4-[3-oxo-3-(1-(3,4-methylenedioxyphenyl)-1,3,4,9-tetrahydro-β-carbolin-2-yl)propenyl]benzamide;

(E)-1-[1-(3,4-Methylenedioxyphenyl)-1,3,4,9-tetrahydro-β-carbolin-2-yl]-3-(3-hydroxyphenyl)propene-1-one;

(E)-1-[1-(3,4-Methylenedioxyphenyl)-1,3,4,9-tetrahydro-β-carbolin-2-yl]-3-(3-methoxyphenyl)propene-1-one;

(E)-1-[1-(3,4-Methylenedioxyphenyl)-1,3,4,9-tetrahydro-β-carbolin-2-yl]-3-(3-nitrophenyl)propene-1-one;

(E)-1-[1-(3,4-Methylenedioxyphenyl)-1,3,4,9-tetrahydro-β-carbolin-2-yl]-3-[4-(2-dimethylaminoethoxy)phenyl]propene-1-one;

(E)-N-(2-Morpholin-4-ylethyl)-4-[3-oxo-3-(1-(3,4-methylenedioxyphenyl)-1,3, 4,9-tetrahydro-β-carbolin-2-yl)propenyl]benzamide;

(E)-1-[1-(3,4-Methylenedioxyphenyl)-1,3,4,9-tetrahydro-β-carbolin-2-yl]-3-[4-(1H-tetrazol-5-yl)phenyl]propene-1-one;

(E)-1-[1-(3,4-Methylenedioxyphenyl)-1,3,4,9-tetrahydro-β-carbolin-2-yl]-3-(3-aminophenyl)propene-1-one;

(E)-N-Cyclohexyl-4-[3-oxo-3-(1-(3,4-methylenedioxyphenyl)-1,3,4,9-tetrahydro-β-carbolin-2-yl)propenyl]benzamide;

(E)-N-(Tetrahydrofuran-2-ylmethyl)-4-[3-oxo-3-(1-(3,4-methylenedioxyphenyl)-1,3,4,9-tetrahydro-β-carbolin-2-yl)propenyl]benzamide;

(E)-1-[1-(3,4-Methylenedioxyphenyl)-1,3,4,9-tetrahydro-β-carbolin-2-yl-3-(3-cyanophenyl)propene-1-one;

(E)-N-(4-Piperidine-4-carboxylic acid, ethyl ester)-4-[3-oxo-3-(1-(3,4-methylenedioxyphenyl)-1,3,4,9-tetrahydro-β-carbolin-2-yl)propenyl]benzamide;

(E)-N-(4-Piperidine-4-carboxylic acid)-4-[3-oxo-3-(1-(3,4-methylenedioxyphenyl)-1,3,4,9-tetrahydro-β-carbolin-2-yl)propenyl]benzamide;

(E)-3-[3-Oxo-3-[1-(3,4-methylenedioxyphenyl)-1,3,4,9-tetrahydro-β-carbolin-2-yl]-propenyl]benzoic acid;

(E)-1-[1-(3,4-Methylenedioxyphenyl)-1,3,4,9-tetrahydro-β-carbolin-2-yl]-3-(3-(4-methylpiperazine-1-carbonyl)-phenyl)propene-1-one;

(E)-N-(2-piperazin-1-ylethyl)-3-[3-oxo-3-(1-(3,4-methylenedioxyphenyl)-1,3, 4,9-tetrahydro-β-carbolin-2-yl)propenyl]benzamide;

(E)-4-[3-Oxo-3-(1-(3,4-methylenedioxyphenyl)-1,3,4,9-tetrahydro-β-carbolin-2-yl)-propenyl]acetic acid ethyl ester;

(E)-1-[1-(3,4-Methylenedioxyphenyl)-1,3,4,9-tetrahydro-β-carbolin-2-yl]-3-(3-tetrazolophenyl)propene-1-one;

(E)-2-[3-Oxo-3-[1-(3,4-methylenedioxyphenyl)-1,3,4,9-tetrahydro-β-carbolin-2-yl]propenyl]benzoic acid, methyl ester;

(E)-3-[3-Oxo-3-[1-(3,4-methylenedioxyphenyl)-1,3,4,9-tetrahydro-β-carbolin-2-yl]propenyl]benzoic acid, methyl ester;

(E)-1-(4-[3-Oxo-3-(1-(3,4-methylenedioxyphenyl)-1,3,4, 9-tetrahydro-β-carbolin-2-yl)-propenyl]phenyl)piperidine-4-carboxylic acid, ethyl ester;

(E)-N-(1-Ethylpyrrolidin-2-yl-methyl)-3-[3-oxo-3-(1-(3, 4-methylenedioxyphenyl)-1,3,4,9-tetrahydro-β-carbolin-2-yl)propenyl]benzamide;

(E)-1-[1-(3,4-Methylenedioxyphenyl)-1,3,4,9-tetrahydro-β-carbolin-2-yl]-3-(3-(2-dimethylaminoethoxy)phenyl)propene-1-one;

(E)-1-[1-(3,4-Methylenedioxyphenyl)-1,3,4,9-tetrahydro-β-carbolin-2-yl]-3-(3,5-diterbutyl-4-hydroxyphenyl)propene-1-one;

(E)-3-[3-Oxo-3-[1-(4-methoxycarbonylphenyl)-1,3,4,9-tetrahydro-β-carbolin-2-yl]propenyl]benzoic acid, methyl ester;

(E)-2-[3-Oxo-3-[1-(3,4-methylenedioxyphenyl)-1,3,4,9-tetrahydro-β-carbolin-2-yl]propenyl]benzoic acid;

(E)-(4-[3-Oxo-3-(1-(3,4-methylenedioxyphenyl)-1,3,4,9-tetrahydro-β-carbolin-2-yl)propenyl]phenoxy)acetic acid, ethyl ester;

(E)-(4-[3-Oxo-3-(1-(3,4-methylenedioxyphenyl)-1,3,4,9-tetrahydro-β-carbolin-2-yl)-propenyl]phenyl)acetic acid;

(E)-(4-[3-Oxo-3-(1-(3,4-methylenedioxyphenyl)-1,3,4,9-tetrahydro-β-carbolin-2-yl)propenyl]phenoxy)acetic acid;

(E)-1-[1-(3,4-Methylenedioxyphenyl)-1,3,4,9-tetrahydro-β-carbolin-2-yl]-3-(3-nitro-4-chlorophenyl)propene-1-one;

(E)-1-[1-(3,4-Methylenedioxyphenyl)-1,3,4,9-tetrahydro-β-carbolin-2-yl]-3-(5-nitro-2-chlorophenyl)propene-1-one;

(E)-3-Chloro-4-[3-oxo-3-(1-(3,4-methylenedioxyphenyl)-1,3,4,9-tetrahydro-beta.-carbolin-2-yl]propenyl]benzoic acid, methyl ester;

(E)-(4-[3-Oxo-3-(1-(3,4-methylenedioxyphenyl)-1,3,4,9-tetrahydro-β-carbolin-2-yl)propenyl]benzyloxy)acetic acid;

(E)-1-[1-(3,4-Methylenedioxyphenyl)-1,3,4,9-tetrahydro-β-carbon-2-yl]-3-(5-amino-2-chlorophenyl)propene-1-one;

(E)-3-Chloro-4-[3-oxo-3-[1-(3,4-methylenedioxyphenyl)-1,3,4,9-tetrahydro-beta-carbolin-2-yl]propenyl]benzoic acid;

(E)-1-[1-(3,4-Methylenedioxyphenyl)-1,3,4,9-tetrahydro-β-carbolin-2-yl]-3-(3,5-dibromo-4-hydroxyphenyl)propene-1-one;

(E)-1-[1-(3,4-Methylenedioxyphenyl)-1,3,4,9-tetrahydro-β-carbolin-2-yl]-3-(4-(2-dimethylaminopropoxy)phenyl)propene-1-one;

(E)-2-Chloro-5-[3-oxo-3-[1-(3,4-methylenedioxyphenyl)-1,3,4,9-tetrahydro-beta-carbolin-2-yl]propenyl]benzoic acid, methyl ester;

(E)-1-[1-(3,4-Methylenedioxyphenyl)-1,3,4,9-tetrahydro-β-carbolin-2-yl]-3-(4-(2-diisopropylaminoethoxy)phenyl)propene-1-one;

(E)-2-Chloro-5-[3-oxo-3-[1-(3,4-methylenedioxyphenyl)-1,3,4,9-tetrahydro-beta-carbolin-2-yl]propenyl]benzoic acid;

(E)-1-[1-(3,4-Methylenedioxyphenyl)-1,3,4,9-tetrahydro-β-carbolin-2-yl]-3-(3-hydroxy-4-nitro-phenyl)propene-1-one;

(E)-1-[1-(3,4-Methylenedioxyphenyl)-1,3,4,9-tetrahydro-1-carbolin-2-yl]-3-(3,5-dimethyl-4-hydroxyphenyl)propene-1-one;

(E)-1-[1-(3,4-Methylenedioxyphenyl)-1,3,4,9-tetrahydro-β-carbolin-2-yl]-3-(3-(2-dimethylaminoethoxy)-4-nitrophenyl)propene-1-one;

(E)-1-[1-(3,4-Methylenedioxyphenyl)-1,3,4,9-tetrahydro-β-carbolin-2-yl]-3-(3-(2-dimethylaminoethoxy)-4-aminophenyl)propene-1-one;

(E)-1-[1-(3,4-Methylenedioxyphenyl)-1,3,4,9-tetrahydro-β-carbolin-2-yl]-3-(3-nitro-4-hydroxy-5-methoxyphenyl)propene-1-one;

(E)-1-[1-(3,4-Methylenedioxyphenyl)-1,3,4,9-tetrahydro-β-carbolin-2-yl]-3-(3-chlorophenyl)propene-1-one;

(E)-1-[1-(4-Methoxy-phenyl)-1,3,4,9-tetrahydro-β-carbolin-2-yl]-3-(2-chloro-5-nitrophenyl)propene-1-one;

(E)-1-[1-(3,4-Methylenedioxyphenyl)-1,3,4,9-tetrahydro-β-carbolin-2-yl]-3-(2,6-dichlorophenyl)propene-1-one;

(E)-1-[1-(3,4-Methylenedioxyphenyl)-1,3,4,9-tetrahydro-β-carbolin-2-yl]-3-(4-methylaminomethylphenyl)propene-1-one;

(E)-1-[1-(3,4-Methylenedioxyphenyl)-1,3,4,9-tetrahydro-β-carbolin-2-yl]-3-(3-methylphenyl)propene-1-one;

(E)-N-Methyl-(4-[3-oxo-3-(1-(3,4-methylenedioxyphenyl)-1,3,4,9-tetrahydro-beta-carbolin-2-yl)propenyl]benzenesulfonamide;

(E)-1-[1-(3,4-Methylenedioxyphenyl)-1,3,4,9-tetrahydro-β-carbolin-2-yl]-3-(3-hydroxy-4-acetylphenyl)propene-1-one;

(E)-1-[1-(2,3-Dihydrobenzofuran-5-yl)-1,3,4,9-tetrahydro-β-carbolin-2-yl]-3-(2-chloro-5-nitrophenyl)propene-1-one;

(E)-1-[1-(3,4-Methylenedioxyphenyl)-1,3,4,9-tetrahydro-β-carbolin-2-yl]-3-(2-hydroxyphenyl)propene-1-one;

(E)-1-[1-(3,4-Methylenedioxyphenyl)-1,3,4,9-tetrahydro-β-carbolin-2-yl]-3-(3-nitro-2-piperidin-1-ylphenyl)propene-1-one;

(E)-1-[1-(2,3-Dihydrobenzofuran-5-yl)-1,3,4,9-tetrahydro-β-carbolin-2-yl]-3-phenylpropene-1-one;

(E)-1-[1-(4-Isopropylphenyl)-1,3,4,9-tetrahydro-β-carbolin-2-yl]-3-(3-nitrophenyl)propene-1-one;

(E)-1-[1-(2,3-Dihydrobenzofuran-5-yl)-1,3,4,9-tetrahydro-β-carbolin-2-yl]-3-(3-nitrophenyl)propene-1-one;

(E)-(R)-1-[1-(3,4-Methylenedioxyphenyl)-1,3,4,9-tetrahydro-β-carbolin-2-yl]-3-phenylpropene-1-one;

(E)-(S)-1-[1-(3,4-Methylenedioxyphenyl)-1,3,4,9-tetrahydro-β-carbolin-2-yl]-3-phenylpropene-1-one;

(E)-1-[1-(4-Methoxyphenyl)-1,3,4,9-tetrahydro-β-carbolin-2-yl]-3-(3-nitrophenyl)propene-1-one;

(E)-1-[1-(4-Methylphenyl)-1,3,4,9-tetrahydro-β-carbolin-2-yl]-3-(2-chloro-5-nitrophenyl)propene-1-one;

(E)-N-(Tetrahydrofuran-2-ylmethyl)-3-[3-oxo-3-(1-(3,4-methylenedioxy)-1,3,4,9-tetrahydro-β-carbolin-2-yl)propenyl]benzamide;

(E)-1-[1-(Indan-5-yl)-1,3,4,9-tetrahydro-β-carbolin-2-yl]-3-phenylprop ene-1-one;

(E)-1-[1-(3,4-Methylenedioxyphenyl)-1,3,4,9-tetrahydro-β-carbolin-2-yl]-3-(3-acetylphenyl)propene-1-one;

(E)-1-[1-(2,3-Dihydrobenzofuran-5-yl)-1,3,4,9-tetrahydro-β-carbolin-2-yl]-3-(4-(2-dimethylaminoethoxy)phenyl)propene-1-one;

(E)-4-[3-Oxo-3-[1-(4-methoxyphenyl)-1,3,4,9-tetrahydro-β-carbolin-2-yl]propenyl]benzoic acid, methyl ester;

(E)-1-[1-(3,4-Methylenedioxyphenyl)-1,3,4,9-tetrahydro-β-carbolin-2-yl]-3-(4-methyl-3,4-dihydro-2H-benzo[1,4]oxazin-6-yl)propene-1-one;

(E)-1-[1-(3,4-Methylenedioxyphenyl)-1,3,4,9-tetrahydro-β-carbolin-2-yl]-3-(2-hydroxy-5-nitrophenyl)propene-1-one;

(E)-4-[3-Oxo-3-[1-(2,3-dihydrobenzofuran-5-yl)-1,3,4,9-tetrahydro-β-carbolin-2-yl]propenyl]benzoic acid, methyl ester;

(E)-4-[3-Oxo-3-[1-(4-methoxyphenyl)-1,3,4,9-tetrahydro-β-carbolin-2-yl]propenyl]benzoic acid;

(E)-4-[3-Oxo-3-[1-(2,3-dihydrobenzofuran-5-yl)-1,3,4,9-tetrahydro-β-carbolin-2-yl]propenyl]benzoic acid;

(E)-1-[1-(Benzofuran-5-yl)-1,3,4,9-tetrahydro-β-carbolin-2-yl]-3-phenylpropene-1-one;

(E)-3-[3-Oxo-3-(1-(3,4-methylenedioxyphenyl)-1,3,4,9-tetrahydro-β-carbolin-2-yl)-propenyl]phenyl)trifluoromethanesulfonic acid, phenyl ester;

(E)-1-[1-(3,4-Methylenedioxyphenyl)-1,3,4,9-tetrahydro-β-carbolin-2-yl]-3-[4-(2-hydroxyethoxy)phenyl]propene-1-one;

(E)-1-[1-(Benzofuran-5-yl-1,3,4,9-tetrahydro-β-carbolin-2-yl)]-3-(4-(2-dimethylaminoethoxy)phenyl)propene-1-one;

(E)-1-[1(3,4-Methylenedioxyphenyl)-1,3,4,9-tetrahydro-β-carbolin-2-yl]-3-(2-dimethylaminophenyl)propene-1-one;

(E)-1-[1-(3,4-Methylenedioxyphenyl)-1,3,4,9-tetrahydro-β-carbolin-2-yl]-3-(2-piperidin-1-ylphenyl)propene-1-one;

(E)-4-[3-Oxo-3-[1-(benzofuran-5-yl-1,3,4,9-tetrahydro-β-carbolin-2-yl]-propenyl]-benzoic acid, methyl ester;

(E)-4-[3-(1-Benzofuran-5-yl-1,3,4,9-tetrahydro-β-carbolin-2-yl)-3-oxo-propenyl]-benzoic acid;

(E)-4-[3-Oxo-3-(1-(3,4-methylenedioxyphenyl)-1,3,4,9-tetrahydro-β-carbolin-2-yl)propenyl]phenyl)trifluoromethanesulfonic acid, phenyl ester;

(E)-1-[1-(3,4-Methylenedioxyphenyl)-1,3,4,9-tetrahydro-β-carbolin-2-yl]-3-(2-(2-dimethylaminoethoxy)phenyl)propene-1-one;

(E)-1-[1-(3-Fluoro-4-methoxyphenyl)-1,3,4,9-tetrahydro-β-carbolin-2-yl]-3-phenylpropene-1-one;

(E)-(R)-1-[1-(2,3-Dihydrobenzofuran-5-yl)-1,3,4,9-tetrahydro-β-carbolin-2-yl)]-3-(4-(2-dimethylaminoethoxy)phenyl)propene-1-one;

(E)-[1-(2,3-Dihydrobenzo[1,4]dioxin-6-yl)-1,3,4,9-tetrahydro-β-carbolin-2-yl]-3-phenylpropene-1-one;

(E)-1-[1-(2,3-Dihydrobenzofuran-5-yl)-1,3,4,9-tetrahydro-β-carbolin-2-yl)]-3-(4-(2-pyrrolidin-1-ylethoxy)phenyl)propene-1-one;

(E)-1-[1-(3,4-Methylenedioxyphenyl)-1,3,4,9-tetrahydro-β-carbolin-2-yl]-3-[4-pyrrolidin-1-ylphenyl]propene-1-one;

(E)-(R)-1-[1-(2,3-Dihydrobenzofuran-5-yl)-1,3,4,9-tetrahydro-β-carbolin-2-yl)]-3-(3-nitrophenyl)propene-1-one;

(E)-1-[1-(3,4-Methylenedioxyphenyl)-1,3,4,9-tetrahydro-β-carbolin-2-yl]-3-[4-imidazol-1-ylphenyl]propene-1-one;

(E)-4-[3-[1-(2,3-Dihydrobenzo[1,4]dioxin-6-yl)-1,3,4,9-tetrahydro-β-carbolin-2-yl]-3-oxo-propenyl]benzoic acid, methyl ester;

(E)-1-[1-(2,3-Dihydrobenzo[1,4]dioxin-6-yl)-1,3,4,9-tetrahydro-β-carbolin-2-yl]-3-(3-nitrophenyl)propene-1-one;

(E)-1-[1-(2,3-Dihydrobenzo[1,4]dioxin-6-yl)-1,3,4,9-tetrahydro-β-carbolin-2-yl)]-3-(4-(2-dimethylaminoethoxy)phenyl)propene-1-one;

(E)-1-[1-(3-Fluoro-4-methoxyphenyl)-1,3,4,9-tetrahydro-β-carbolin-2-yl)]-3-(4-(2 dimethylaminoethoxy)phenyl)propene-1-one;

(E)-4-[3-[1-(2,3-Dihydrobenzo[1,4]dioxin-6-yl)-1,3,4,9-tetrahydro-β-carbolin-2-yl]-3-oxopropenyl]benzoic acid;

(E)-(R)-1-[1-(2,3-Dihydrobenzofuran-5-yl)-1,3,4,9-tetrahydro-β-carbolin-2-yl]-3-phenylpropene-1-one;

(E)-(S)-1-[1-(2,3-Dihydrobenzofuran-5-yl)-1,3,4,9-tetrahydro-β-carbolin-2-yl)]-3-(4-(2-dimethylaminoethoxy)phenyl)propene-1-one;

(E)-1-[1-(2,3-Dihydrobenzofuran-5-yl)-1,3,4,9-tetrahydro-β-carbolin-2-yl]-3-(4-aminophenyl)propene-1-one;

(E)-(S)-1-[1-(2,3-Dihydrobenzofuran-5-yl)-1,3,4,9-tetrahydro-β-carbolin-2-yl]-3-phenylpropene-1-one;

(E)-(S)-1-[1-(2,3-Dihydrobenzofuran-5-yl)-1,3,4,9-tetrahydro-β-carbolin-2-yl]-3-(3-nitrophenyl)propene-1-one;

(E)-(R)-1-[1-(2,3-Dihydrobenzofuran-5-yl)-1,3,4,9-tetrahydro-β-carbolin-2-yl)]-3-(4-(1-(S)-methylpyrrolidin-2-yl-methoxy)phenyl)propene-1-one;

(E)-(R)-1-[1-(2,3-Dihydrobenzofuran-5-yl)-1,3,4,9-tetrahydro-β-carbolin-2-yl)]-3-(3-hydroxyphenyl)propene-1-one;

(E)-(R)-1-[1-(2,3-Dihydrobenzofuran-5-yl)-1,3,4,9-tetrahydro-β-carbolin-2-yl)]-3-(4-(2-dimethylamino-1-methylethoxy)phenyl)propene-1-one;

(E)-1-(1-Phenyl-1,3,4,9-tetrahydro-β-carbolin-2-yl)-3-(4-(4-methylpyperazin-1-yl)-phenyl)propene-1-one;

(E)-(R)-1-[1-(3,4-Methylenedioxyphenyl)-1,3,4,9-tetrahydro-β-carbolin-2-yl)]-3-(4-(1-(S)-methylpyrrolidin-2-yl-methoxy)phenyl)propene-1-one;

(E)-R)-1-[1-(3,4-Methylenedioxyphenyl)-1,3,4,9-tetrahydro-β-carbolin-2-yl]-3-(4-(2-dimethylamino-1-methyl-ethoxy)phenyl)propene-1-one;

(E)-(R)-1-[1-(3,4-Methylenedioxyphenyl)-1,3,4,9-tetrahydro-β-carbolin-2-yl)]-3-(4-(2-dimethylaminopropoxy)phenyl)propene-1-one;

(E)-4-[3-Oxo-3-[1-(3,4-fluorophenyl)-1,3,4,9-tetrahydro-β-carbolin-2-yl]propenyl]benzoic acid, methyl ester;

(E)-(R)-[1-(2,3-Dihydrobenzofuran-5-yl)-1,3,4,9-tetrahydro-β-carbolin-2-yl)]-3-(4-(2-diethylaminoethoxy)phenyl)propene-1-one;

(E)-(R)-1-[1-(2,3-Dihydrobenzofuran-5-yl)-1,3,4,9-tetrahydro-β-carbolin-2-yl)]-3-(4-(2-dimethylaminopropoxy)phenyl)propene-1-one;

(E)-4-[3-Oxo-3-[1-(3,4-difluorophenyl)-1,3,4,9-tetrahydro-β-carbolin-2-yl]propenyl]benzoic acid;

(E)-(R)-1-[1-(2,3-Dihydrobenzofuran-5-yl)-1,3,4,9-tetrahydro-β-carbolin-2-yl)]-3-(4-aminophenyl)propene-1-one;

(E)-(R)-1-[1-(3,4-Methylenedioxyphenyl)-1,3,4,9-tetrahydro-β-carbolin-2-yl]-3-(4-aminophenyl)propene-1-one;

(E)-(R)-1-[1-(3,4-Methylenedioxyphenyl)-1,3,4,9-tetrahydro-β-carbolin-2-yl)]-3-(4-(2-pyrrolidin-1-ylethoxy) phenyl)propene-1-one;

(E)-(R)-1-[1-(3,4-Methylenedioxyphenyl)-1,3,4,9-tetrahydro-β-carbolin-2-yl)]-3-(4(2-diethylaminoethoxy)phenylpropene-1-one;

(E)-1-[1-(3-Fluoro-4-methoxyphenyl)-1,3,4,9-tetrahydro-β-carbolin-2-yl)]-3-(3-nitrophenyl)propene-1-one;

(E)-(R)-1-[1-(2,3-Dihydrobenzofuran-5-yl)-1,3,4,9-tetrahydro-β-carbolin-2-yl]-3-(4-trifluoromethylphenyl)propene-1-one;

(E)-(R)-1-[1-(2,3-Dihydrobenzofuran-5-yl)-1,3,4,9-tetrahydro-β-carbolin-2-yl]-3-(3-trifluoromethylphenyl)propene-1-one;

(E)-(R)-1-[1-(2,3-Dihydrobenzofuran-5-yl)-1,3,4,9-tetrahydro-β-carbolin-2-yl]-3-(4-(2-morpholin-4-ylethoxy) phenyl)propene-1-one;

(E)-(R)-1-[1-(2,3-Dihydrobenzofuran-5-yl)-1,3,4,9-tetrahydro-β-carbolin-2-yl]-3-(4-(2-(ethylmethylamino) ethoxy)phenyl)propene-1-one;

(E)-1-[1 (2,3-Dihydrobenzofuran-5-yl)-1,3,4,9-tetrahydro-β-carbolin-2-yl]-3-(4-(3-(dimethylamino)propenyl)phenyl)propene-1-one;

(E)-(R)-1-[1-(2,3-Dihydrobenzofuran-5-yl)-1,3,4,9-tetrahydro-β-carbolin-2-yl]-3-(4-(3-dimethylamino-2-hydroxypropoxy)phenyl)propene-1-one;

(E)-(R)-1-(1-(2,3-Dihydrobenzofuran-5-yl)-1,3,4,9-tetrahydro-(3-carbolin-2-yl)-3-(4-formylphenyl)propene-1-one;

(E)-(R)-1-[1-(2,3-Dihydrobenzofuran-5-yl)-1,3,4,9-tetrahydro-β-carbolin-2-yl]-3-(4-propylaminomethyl)phenyl) propene-1-one;

(E)-(R)-1-[1-(2,3-Dihydrobenzofuran-5-yl)-1,3,4,9-tetrahydro-β-carbolin-2-yl]-3-[4-(2-dimethylaminoethylamino)phenylpropene-1-one;

(E)-(R)-1-[1-(2,3-Dihydrobenzofuran-5-yl)-1,3,4,9-tetrahydro-β-carbolin-2-yl]-3-(4-(2-aminoethoxy)phenyl)propene-1-one;

(E)-(R)-1-[1-(2,3-Dihydrobenzofuran-5-yl)-1,3,4,9-tetrahydro-β-carbolin-2-yl]-3-(4-hydroxyphenyl)propene-1-one;

(E)-(R)-1-[1-(2,3-Dihydrobenzofuran-5-yl)-1,3,4,9-tetrahydro-β-carbolin-2-yl]-3-(4-(4-methylpiperazin-1-yl)phenylpropene-1-one;

(E)-(R)-1-[1-(2,3-Dihydrobenzofuran-5-yl)-1,3,4,9-tetrahydro-β-carbolin-2-yl]-3-(4-methylaminomethyl)phenyl) propene-1-one;

(E)-(R)-1-[1-(2,3-Dihydrobenzofuran-5-yl)-1,3,4,9-tetrahydro-β-carbolin-2-yl]-3-(4-isopropylaminomethyl)phenyl)propene-1-one;

(E)-(R)-1-[1-(2,3-Dihydrobenzofuran-5-yl)-1,3,4,9-tetrahydro-β-carbolin-2-yl]-3-(4-dimethylaminomethyl)phenyl)propene-1-one;

(E)-(R)-1-[1-(2,3-Dihydrobenzofuran-5-yl)-1,3,4,9-tetrahydro-β-carbolin-2-yl]-3-[4-(3-dimethylaminopropoxy) phenyl]propene-1-one;

(E)-(R)-1-[1-(2,3-Dihydrobenzofuran-5-yl)-1,3,4,9-tetrahydro-β-carbolin-2-yl]-3-(4-(2-piperidin-1-ylethoxy)phenyl)propene-1-one;

(E)-1-[1-(3,4-Methylenedioxyphenyl)-1,3,4,9-tetrahydro-β-carbolin-2-yl)-3-(4-(2-piperidin-1-yl-ethoxy)phenyl]propene-1-one;

(E)-(R)-[2-(4-{3-[1-(2,3-Dihydrobenzofuran-5-yl)-1,3,4,9-tetrahydro-β-carbolin-2-yl]-3-oxopropenyl}-phenoxy) ethyl]methylcarbamic acid, tertbutyl ester;

(E)-(R)-1-[1-(2,3-Dihydrobenzofuran-5-yl)-1,3,4,9-tetrahydro-carbolin-2-yl]-3-[4-(2-methylaminoethoxy)phenyl] propene-1-one; and pharmaceutically acceptable salts and solvates (e.g., hydrates) of such compounds.

Additional preferred PDE inhibitor compounds for use in accordance with the invention may be identified by simple testing, such as in by exhibiting an $ID_{50}$ of less than about 10 mM, preferably less than about 1 mM in an in vitro assay for determining PDE or PDE-5 inhibitory action as disclosed in U.S. Pat. No. 6,100,270; WO-A-93/06104; WO-A-93/07149; WO-A-93/12095; and WO-A-94/00453.

As indicated above, the present invention includes methods for treating or preventing prostalandin mediated or associated diseases or disorders.

Preferred therapeutic methods of the invention include inhibiting undesired smooth muscle contraction, including undesired prostanoid-induced smooth muscle contraction. Methods of the invention include treatment of a patient suffering from or susceptible to dysmenorrhea, premature labor, asthma and other conditions that can be relieved by bronchodilation, inflammation, hypertension, undesired blood-clotting (e.g. to reduce or prevent thromboses) and other undesired platelet activities, preeclampsia and/or eclampsia and eosinophil-related disorders (eosinophil disorders).

Treatment and/or prevention of undesired blood clotting may include treatment and prophylaxis of venous thrombosis and pulmonary embolism, arterial thrombosis e.g. myocardial ischemia, myocardial infarction, unstable angina, stroke associated with thrombosis, and peripheral arterial thrombosis. Pyrrolidine compounds of the invention also may be useful for anticoagulation involving artificial organs, cardiac valves, medical implementation (e.g. an indwelling device such as a catheter, stent, etc.) and the like.

The invention also includes methods for treatment of infertility, which generally comprise administration of one or more pyrrolidine compounds of the invention to a mammal, particularly a primate such as a human, suffering from or suspected of suffering from infertility. See the *Merck Manual*, vol. 2, pages 12-17 (16$^{th}$ ed.) for identification of patients suffering from or suspected of suffering from inferility, which in the case of humans, can include failure to conceive within one year of unprotected intercourse.

The treatment methods of the invention may be particularly beneficial for female mammals suffering from an ovulatory disorder. Additionally, compounds of the invention can be administered to females undergoing assisted reproductive treatments such as in-vitro fertilization, e.g. to stimulate follicular development and maturation, as well as implantation procedures. In particular, treatment methods of the invention may be used in conjunction with in vitro fertilization technology to enhance survival and/or fertilization of a mammalian egg such as in IVF setting.

Treatment methods of the invention also may be employed for control of cervical ripening in late pregnancy (e.g. in humans, late pregnancy would be third trimester, particularly week 30 onward).

Therapeutic methods of the invention also include treatment of glaucoma, inhibition or prevention of bone loss such as to treat osteoporosis, and for promoting bone formation (e.g. to use as a therapy in a bone fracture) and other bone diseases such as Paget's disease.

Compounds of the invention also will be useful to treat sexual dysfunction, including male erectile dysfunction.

The therapeutic methods of the invention generally comprise administration of an effective amount of one or more pyrrolidine compounds of the invention to a subject including a mammal, such as a primate, especially a human, in need of such treatment.

Typical candidates for treatment in accordance with the methods of the invention persons suffering from or suspected of suffering from any of the above disorders or diseases, such as a female susceptible or suffering from preterm labor, or a subject suffering from or susceptible to dysmenorrhea or undesired bone loss.

The treatment methods of the invention also will be useful for treatment of mammals other than humans, including for veterinary applications such as to treat horses and livestock e.g. cattle, sheep, cows, goats, swine and the like, and pets such as dogs and cats. Methods of the invention to treat premature labor will be particularly useful for such veterinary applications. Therapeutic methods of the invention also will be useful for treatment of infertility in such veterinary applications.

For diagnostic or research applications, a wide variety of mammals will be suitable subjects including rodents (e.g. mice, rats, hamsters), rabbits, primates and swine such as inbred pigs and the like. Additionally, for in vitro applications, such as in vitro diagnostic and research applications, body fluids (e.g., blood, plasma, serum, cellular interstitial fluid, saliva, feces and urine) and cell and tissue samples of the above subjects will be suitable for use.

In addition to coordinated administration with a PDE inhibitor compound as discussed above, pyrrolidine compounds of the invention may be administered as a "cocktail" formulation with other therapeutics, i.e. coordinated administration of one or more compounds of the invention together with one or more other active therapeutics, particularly one or more other known fertility agents. For instance, one or more compounds of the invention may be administered in coordination with a regime of a pain relief agent, an anti-inflammatory agent, or an anti-cogulant, depending on the indication being treated. Suitable anti-coagulants for such coordinated drug therapies include e.g. warfarin, heparin, hirudin or hirulog or an antiplatelet such as ReoPro.

For treatment of fertility disorders, one or more compounds of the invention may be suitably administered in coordination with known fertility agents such as Follicle Stimulating and/or Leutinizing Hormone such as Gonal-F, Metrodin HP or Pergonal.

Pyrrolidine compounds of the invention either as the sole active therapeutic or in a coordinated regime such as together with one or more PDE inhibitor compounds can be administered by a variety of routes, such as orally or by injection, e.g., intramuscular, intraperitoneal, subcutaneous or intravenous injection, or topically such as transdermally, vaginally and the like. Pyrrolidine compounds of the invention may be suitably administered to a subject in the protonated and water-soluble form, e.g., as a pharmaceutically acceptable salt of an organic or inorganic acid, e.g., hydrochloride, sulfate, hemi-sulfate, phosphate, nitrate, acetate, oxalate, citrate, maleate, mesylate, etc. If the compound has an acidic group, e.g. a carboxy group, base addition salts may be prepared. Lists of additional suitable salts may be found, e.g. in Part 5 of *Remington's Pharmaceutical Sciences*, 20$^{th}$ Edition, 2000, Marck Publishing Company, Easton, Pa.

Pyrrolidine compounds of the invention can be employed, either alone or in combination with one or more other therapeutic agents as discussed above, as a pharmaceutical composition in mixture with conventional excipient, i.e., pharmaceutically acceptable organic or inorganic carrier substances suitable for oral, parenteral, enteral or topical application which do not deleteriously react with the active compounds and are not deleterious to the recipient thereof Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

Pharmaceutical compositions of the invention include a pyrrolidine compound of the invention packaged together with instructions (written) for therapeutic use of the compound to treat e.g. premature labor, dysmenorrhea or asthma, or other disorder as disclosed herein, such as a disease or disorder associated with or mediated by prostaglandin.

For oral administration, pharmaceutical compositions containing one or more substituted pyrrolidine compounds of the invention may be formulated as e.g. tablets, troches, lozenges, aqueous or oily suspensions, dispersible powders or granules, emulsions, hard or soft capsules, syrups, elixers and the like. Typically suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is is protected with differentially degradable coatings, e.g., by microencapsulation, multiple coatings, etc.

For parenteral application, e.g., sub-cutaneous, intraperitoneal or intramuscular, particularly suitable are solutions, preferably oily or aqueous solutions as well as suspensions, emulsions, or implants, including suppositories. Ampules are convenient unit dosages.

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines. See also *Remington's Pharmaceutical Sciences*, supra. In general, a suitable effective dose of one or more pyrrolidine compounds of the invention, particularly when using the more potent compound(s) of the invention, will be in the range of from 0.01 to 100 milligrams per kilogram of bodyweight of recipient per day, preferably in the range of from 0.01 to 20 milligrams per kilogram bodyweight of recipient per day, more preferably in the range of 0.05 to 4 milligrams per kilogram bodyweight of recipient per day. The desired dose is suitably administered once daily, or several sub-doses, e.g. 2 to 4 sub-doses, are administered at appropriate intervals through the day, or other appropriate schedule. Such sub-doses may be administered as unit dosage forms, e.g., containing from 0.05 to 10 milligrams of compound(s) of the invention, per unit dosage.

The entire text of all documents cited herein are incorporated by reference herein. The following non-limiting examples are illustrative of the invention. In the examples below, "rac." refers to a racemate or racemic mixture of the specified compound.

EXAMPLES 1-21

Synthesis of Compounds of the Invention

The Compounds of Examples 1 to 21 are Preferred Embodiments of the Invention:

Example 1

Synthesis of (5Z)7-[(2R,3R)-3-Chloro-1-(4-hydroxynonyl)-pyrrolidin-2-yl]-hept-5-enoic Acid (Scheme 2, Steps A-B and D-F)

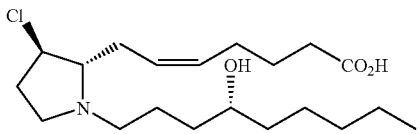

Intermediate 1.1: methyl(3-{[tert-butyl(dimethyl)silyl]oxy}pyrrolidin-2-yl)acetate.

To a methanolic solution (50 mL) of 3-(tert-butyl-dimethyl-silanyloxy)-2-methoxycarbonylmethyl-pyrrolidine-1-carboxylic acid benzyl ester (obtained from 3-aminopropanal according to the procedure of Macdonald et al: *J. Med. Chem.* 1998, 41(21), 3919-3922)) (10.0 g. 0.025 mol) was added Pd/C (1.0 g). The mixture was stirred under $H_2$ atmosphere (1 atm) for 4 h, then filtered through celite and concentrated under reduced pressure to afford the desired intermediate (6.0 g, 90%) as a colorless oil used in the next step without further purification. $^1$H NMR (CDCl$_3$) δ (mixture of diastereoisomers) 0.05 (s, 6H), 0.87 (s, 9H), 1.65-1.82 (m, 1H), 1.95-2.05 (m, 1H), 2.3-2.7 (m, 2H), 2.95-3.4 (m, 2H), 3.67-3.68 (2s, 3H), 3.90-4.31 (m, 1H); MS (m/z) 274.2 (M+1).

Intermediate 1.2: tert-butyl 3-{[tert-butyl(dimethyl)silyl]oxy}-2-(2-methoxy-2-oxoethyl)pyrrolidine-1-carboxylate.

To a solution of intermediate 1.1 (6.0 g, 0.022 mol) in DCM (100 mL) were added di-tert-butyl dicarbonate (3.7 mL, 0.026 mol), Et$_3$N (3.7 mL, 0.026 mol), and DMAP (0.6 g). The resulting solution was stirred at RT for 18 h then was washed with HCl 1.0M (2×100 mL) and brine (100 mL), dried over sodium sulfate and concentrated in vacuo to afford the desired intermediate (8.0 g, 97%) as a pale yellow oil used in the next step without further purification. R$_f$ 0.6 EtOAc/hexane 1/4); $^1$H NMR (CDCl$_3$) δ (mixture of diastereoisomers) 0.04-0.06 (2s, 6H), 0.88-0.90 (2s, 9H), 1.42-1.45 (2s, 9H), 1.70-2.20 (m, 2H), 2.55-2.90 (m, 2H), 3.30-3.55 (m, 2H), 3.60-3.70 (2s, 3H), 3.8-4.0 (m, 1H).

Intermediate 1.3 and 1.4: tert-butyl 3-{[tert-butyl(dimethyl)silyl]oxy}-2-(2-hydroxyethyl)pyrrolidine-1-carboxylate.

To a solution of intermediate 1.2 (7.5 g, 0.02 mol) in dry benzene (150 mL) was added dropwise a solution of Red-Al (6.3 mL, 65+wt % solution in toluene, 0.022 mol). This solution was stirred at reflux for 1 h then cooled to RT and quenched with a saturated solution of Rochelle salt. The mixture was extracted with EtOAc (2×150 mL) and the collected organic phase was washed with brine (200 mL), dried and concentrated in vacuo. The crude mixture of diastereoisomers was purified by silica gel flash column chromatography using EtOAc/hexane as eluent to afford the desired intermediates.

Intermediate 1.3 (cis isomer): R$_f$ 0.30 (EtOAc/hexane 1/4); $^1$H NMR (CDCl$_3$) δ 0.06 (s, 6H), 0.88 (s, 9H), 1.2-1.4 (m, 2H), 1.45 (s, 9H), 1.90-2.10 (m, 2H), 3.20-3.40 (m, 2H), 3.50-3.72 (m, 2H), 4.00-4.10 (m, 1H), 4.25-4.40 (m, 2H); MS (m/z): 346 (M+1).

Intermediate 1.4 (trans isomer): R$_f$ 0.25 (EtOAc/hexane 1/4); $^1$H NMR (CDCl$_3$) δ 0.05 (s, 6H), 0.85 (s, 9H), 1.1-1.2 (m, 1H), 1.45 (s, 9H), 1.70-2.00 (m, 2H), 3.30-3.70 (m, 5H), 3.85-4.02 (m, 2H), 4.53 (dd, J=5.5 and 9.5 Hz, 1H); MS (nt/z): 346 (M+1).

Intermediate 1.5: tert-butyl (2R)-3-{[tert-butyl(dimethyl)silyl]oxy}-2-[(2Z)-7-methoxy-7-oxohept-2-enyl]pyrrolidine-1-carboxylate.

Step A (Swern Oxidation):

A DCM solution of oxalyl chloride (5.3 mL, 2.0 M, 10.55 mmol) was diluted with dry DCM (50 mL) and cooled to −70° C. then a solution of DMSO (0.92 mL, 13 mmol) in DCM (10 mL) was added dropwise. After 15 min. to this solution was added dropwise a solution of intermediate 1.3 (2.8 g, 8.1 mmol) in DCM (20 mL). The resulting solution was stirred at −78° C. for 45 min. then Et$_3$N (5.6 mL, 40.6 mmol) was added and the solution warmed to RT. After 15 min. the solution was diluted with DCM (100 mL) and washed with a saturated solution of NH$_4$Cl (2×100 mL), brine (100 mL), dried over sodium sulfate and concentrated in vacuo to afford the aldehyde intermediate (2.75 g, 97%) used in the next step without further purification. R$_f$ 0.40 (EtOAc/hexane 1/4); $^1$H NMR (CDCl$_3$) δ 0.04-0.07 (2s, 6H), 0.86 (s, 9H), 1.43 (s, 9H), 1.70-2.05 (m, 2H), 2.50-2.85 (m, 2H), 3.30-3.45 (m, 2H), 4.20-4.30 (m, 1H), 4.39 (dd, J=6.2 and 12.5 Hz, 1H); MS (m/z): 344 (M+1).

Step B (Wittig Reaction):

A suspension of (4-carboxybutyl)triphenylphosphonium bromide (5.1 g, 11.6 mmol) in THF (40 mL) was cooled to 0° C. and KO$^t$Bu was added portionwise. After 15 min. was added a solution of the aldehyde (2.75 g, 8.1 mmol) in THF (10 mL). The resulting mixture was stirred at RT for 18 h then was diluted EtOAc (150 mL) and washed with HCl 1M solution (100 mL) and brine. The organic phase was dried over sodium sulfate and concentrated in vacuo to afford the crude acid used directly in the next step.

Step C (Esterification Reaction):

To a solution of the crude acid in DCM (30 mL) and MeOH (7 mL) was added dropwise a solution of trimethylsylildiazomethane (50 mL, 2 M solution in hexane, 12 mmol). The resulting solution was stirred at RT for 18 h then was concentrated under reduced pressure. The crude residue was subjected to flash chromatography and was eluted with EtOAc/hexane to afford the desired intermediate (3.1 g, 88%) as a colorless oil. R$_f$ 0.50 (EtOAc/hexane 1/4); $^1$H NMR (CDCl$_3$) δ 0.07 (s, 6H), 0.88 (s, 9H), 1.44 (s, 9H), 1.60-1.70 (m, 2H), 1.80-2.15 (m, 4H), 2.20-2.45 (m, 4H), 3.25-3.40 (m, 2H), 3.65 (s, 3H), 3.66-3.90 (m, 1H), 4.25-4.33 (m, 1H), 5.30-5.40 (m, 1H), 5.43-5.58 (m, 1H).

Intermediate 1.6: rac. tert-butyl (2R)-3-hydroxy-2-[(2Z)-7-methoxy-7-oxohept-2-enyl]pyrrolidine-1-carboxylate.

To a solution of intermediate 1.5 (3.0 g, 6.8 mmol) in THF (20 mL) was added a solution of TBAF (7.5 mL, 1.0 M, 7.5 mmol) in THF. The clear solution was stirred at RT for 2 h then was concentrated under reduced pressure. The residue was diluted with EtOAc (100 mL), washed with water (100 mL), brine (100 mL), dried over sodium sulfate and concentrated in vacuo to afford the alcohol intermediate (1.95 g, 88%) used in the next step without further purification. $R_f$ 0.40 (EtOAc/hexane 1/1); $^1$H NMR (CDCl$_3$) δ 1.45 (s, 9H), 1.65-1.75 (m, 2H), 1.80-2.00 (m, 2H), 2.10-2.20 (m, 2H), 2.26-2.45 (m, 4H), 3.32-3.50 (m, 3H), 3.66 (s, 3H), 3.75-3.86 (m, 1H), 4.32-4.42 (m, 1H), 5.35-5.55 (m, 2H).

Intermediate 1.7: rac. tert-butyl (2R)-2-[(2Z)-7-methoxy-7-oxohept-2-enyl]-3-{[(4-methylphenyl)sulfonyl]oxy}pyrrolidine-1-carboxylate.

To a solution of intermediate 1.6 (0.5 g, 1.53 mmol) in pyridine (5 mL) was added tosyl chloride. The solution was stirred at RT for 10 h then at 50° C. for an additional 4 h. The reaction mixture was concentrated in vacuo, diluted with EtOAc (100 mL) and washed with HCl 1.0 M (100 mL), brine (100 mL), dried over sodium sulfate and concentrated in vacuo. The crude residue was subjected to flash chromatography and was eluted with EtOAc/hexane to afford the desired intermediate (0.51 g, 70%) as colorless oil. $R_f$ 0.3 (EtOAc/hexane 1/4); $^1$H NMR (CDCl$_3$) δ 1.20-1.30 (m, 1H), 1.41 (s, 9H), 1.60-1.75 (m, 2H), 1.90-2.15 (m, 4H), 2.20-2.50 (m, 3H), 2.45 (s, 3H), 3.20-3.45 (m, 2H), 3.64 (s, 3H), 3.85-3.95 (m, 1H), 4.91 (q, J=6.6 Hz, 11, 5.30-5.45 (m, 2H), 7.32 (d, J=8.1 Hz, 2H)), 7.78 (d, J=8.1 Hz, 2H).

Intermediate 1.8: rac. tert-butyl (2R)-3-chloro-2-[(2Z)-7-methoxy-7-oxohept-2-enyl]pyrrolidine-1-carboxylate.

To a solution of intermediate 1.7 (0.9 g, 1.80 mmol) in dry toluene (60 mL) was added tetrabutyl ammonium chloride (5.0 g, 18.0 mmol). The reaction mixture was stirred at 55° C. for 48 h then was diluted with water and extracted with EtOAc (2×100 mL). The collected organic phase was washed with water (2×100 mL), saturate solution of NaHCO$_3$ (100 mL), and brine (100 mL). The organic solution was dried over sodium sulfate and concentrated in vacuo to afford the desired intermediate (0.6 g, 96%) as a colorless oil. $R_f$ 0.50 (EtOAc/hexane 1/4); $^1$H NMR (CDCl$_3$) δ 1.46 (s, 9H), 1.60-1.75 (m, 2H), 2.02-2.16 (m, 4l), 2.25-2.55 (m, 4H), 3.38-3.70 (m, 2H), 3.66 (s, 3H), 3.87-4.08 (m, 1H), 4.15-4.25 (m, 1H), 5.30-5.55 (m, 2H).

Intermediate 1.9: rac. Methyl (5Z)-7-[(2R,3R)-3-chloropyrrolidin-2-yl]hept-5-enoate.

Intermediate 1.8 (0.30 g, 0.87 mmol) was treated with a solution of HCl in dioxane (6 mL, 4M solution). The resulting solution was stirred at 0° C. for 2 h then was concentrated under reduced pressure. The crude residue was diluted with a saturated solution of NaHCO$_3$ (50 mL) and extracted with EtOAc (3×40 mL). The collected organic phase was washed with brine (100 mL), dried over sodium sulfate and concentrated under reduced pressure to afford the amine intermediate (0.24 g, 95%) used in the next step without further purification. MS (m/z): 246 (M+1).

Intermediate 1.10: tert-Butyl(dimethyl)[(1-pentylprop-2-ynyl)oxy]silane.

To a solution of (R)-1-octyn-3-ol (5.0 g, 0.039 mol) in DMF (50 mL) were added tert-butyldimethylsylil chloride (7.16 g, 0.0475 mol) and imidazole (3.2 g, 0.0475 mol). The resulting solution was stirred at RT for 18 h then diluted with ether (200 mL) and washed with water (2×200 ml), saturated solution of NH$_4$Cl (200 mL), and brine (200 mL). The organic solution was dried over sodium sulfate and concentrated in vacuo to afford the desired compound (9.0 g, 95%) as a colorless oil used in the next step without further purification. $R_f$ 0.9 (EtOAc/hexane 1/9); $^1$H NMR (CDCl$_3$) δ 0.09 (s, 3H), 0.12 (s, 3H), 0.89 (s, 91), 0.85-1.00 (t, 3H), 1.20-1.70 (m, 8H), 2.35 (s, 1H), 4.30-4.35 (m, 1H).

Intermediate 1.11: (4R)-4-{[tert-Butyl(dimethyl)silyl]oxy}non-2-yn-1-ol.

To a solution of intermediate 1.10 (0.50 g, 2.08 mmol) in dry THF (15 mL) cooled at −70° C. was added dropwise a solution of n-BuLi in hexane (1.36 mL, 1.6 M, 2.18 mmol). The resulting solution was stirred at −70° C. for 10 minutes then para-formaldehyde (0.16 g, 5.46 mmol) was added. The resulting mixture was stirred at RT for 4 h then was diluted with EtOAc (100 mL) and washed with a saturated solution of NH$_4$Cl (100 mL), brine (100 mL), dried and concentrated in vacuo. The crude residue was purified by flash column chromatography (EtOAc/hexane) to afford the title compound (0.42 g, 75%) as a colorless oil. $R_f$ 0.3 (EtOAc/hexane 1/9); $^1$H NMR (CDCl$_3$) δ 0.09 (s, 3H), 0.11 (s, 3H[), 0.89 (s, 9H), 0.85-0.90 (t, 3H), 1.20-1.70 (m, 8H), 4.27 (s, 2H), 4.30-4.40 (m, 1H).

Intermediate 1.12: (4R)-4-{[tert-Butyl(dimethyl)silyl]oxy}nonan-1-ol.

A heterogeneous mixture of intermediate 1.11 (1.0 g, 5.3 mmol) and 10% Pd/C (catalytic amount) in EtOAc (20 mL) was stirred in an atmosphere of hydrogen for 3 h. The solvent was filtered via celite, concentrated in vacuo to give a glassy residue of two products which were separated by flash chromatography (EtOAc-hexane 1-9) gave the saturated alcohol 1.12 (0.79 g, 77%): $R_f$ 0.10 (EtOAc/hexane 1/9), MS (m/z) 276 (M+1) and the correspondent aldehyde 1.13 (0.24 g 23%): $R_f$=0.47 (EtOAc/hexane 1/9), MS (m/z) 273 (M+1).

Intermediate 1.13: (4R)-4 {[tert-Butyl(dimethyl)silyl]oxy}nonanal.

A solution of oxalyl chloride in DCM (1.85 mL, 2.0 M, 3.70 mmol) was diluted with dry DCM (20 mL) and cooled to −70° C. and a solution of DMSO (0.32 mL, 4.55 mmol) in DCM (5.0 mL) was added dropwise. After 15 min., to the above solution was added dropwise a solution of intermediate 1.12 (0.78 g, 2.84 mmol) in DCM (10 mL). The resulting solution was stirred at −78° C. for 45 min. then Et$_3$N (2.0 mL, 14.23 mmol) was added and the solution was warmed to RT. After 15 min. the solution was diluted with DCM (50 mL) and washed with a saturated solution of NH4Cl (2×50 mL), brine (50 mL), dried over sodium sulfate and concentrated in vacuo to afford the aldehyde intermediate (0.80 g, 98%) used in the next step without further purification. $R_f$ 0.50 (EtOAc/hexane 1/9).

Intermediate 1.14: rac. Methyl (5Z)-7-[(2R,3R)-1-(4-{[tert-butyl(dimethyl)-silyl]oxy}nonyl)-3-chloropyrrolidin-2-yl]hept-5-enoate.

To a solution of intermediate 1.9 (0.15 g, 0.61 mmol) and intermediate 1.13 (0.20 g, 0.74 mmol) in MeOH (10 mL) was added a solution of NaCNBH$_3$ in THE (1.2 mL, 1.0 M, 1.20 mmol). The resulting solution was stirred at RT for 18 h then was concentrated in vacuo, diluted with EtOAc (50 mL) and washed with a saturated solution of NaHCO$_3$ (50 mL), and brine (50 mL). The organic solution was dried over sodium sulfate and concentrated in vacuo. The crude residue was purified by silica gel flash column chromatography using EtOAc/hexane as eluent to afford the desired intermediate (0.29 g, 96%) as a colorless oil. $R_f$ 0.75 (EtOAc/hexane 1/4); MS (m/z): 503 (M+1).

Intermediates 1.15 and 1.16: methyl(5Z)-7-[3-chloro-1-(4-hydroxynonyl)-pyrrolidin-2-yl]hept-5-enoate.

To a solution of intermediate 1.14 (1.20 g, 1.22 mmol) in dioxane (40 mL) was added a solution of HCl in dioxane (10 mL, 4.0 M). The solution was stirred at RT for 2 h then was concentrated under reduced pressure. The crude residue was diluted with a saturated solution of NaHCO$_3$ (20 mL) and extracted with EtOAc (3×30 mL). The collected organic phase was washed with brine, dried, and concentrated under reduced pressure. Silica gel column chromatography eluted with EtOAc/hexane allowed the separation of the two diastereoisomers intermediate. Intermediate 1.15 (first isomer, 240 mg): $R_f$ 0.5 (EtOAc/hexane 1/1); $^1$H NMR (CDCl$_3$) δ 0.80-0.95 (m, 3H), 1.20-1.80 (m, 15H), 1.95-2.52 (m, 10H), 2.65-2.72 (m, 1H), 2.75-2.85 (m, 1H), 3.15-3.27 (m, 1H), 3.40-3.52 (m, 1H), 3.66 (s, 3H), 3.95-4.05 (m, 1H), 5.40-5.55 (m, 2H). Intermediate 1.16 (second isomer, 220 mg): $R_f$ 0.45 (EtOAc/hexane 1/1); $^1$H NMR (CDCl$_3$) δ 0.80-0.95 (m, 3H), 1.20-1.80 (m, 15H), 1.95-2.60 (m, 10), 2.65-2.85 (m, 2H), 3.10-3.25 (m, 1H), 3.40-3.52 (m, 1H), 3.65 (s, 3H), 3.95-4.05 (m, 1H), 5.40-5.55 (m, 2H).

The title compound, (5Z)7-[(2R,3R)-3-chloro-1-(4-hydroxynonyl)-pyrrolidin-2-yl]-hept-5-enoic acid, was then prepared as follows. To a solution of intermediate 1.16 (0.22 g, 0.56 mmol) in MeOH (3.4 mL) and THF (3.4 mL) was added a solution of NaOH in water (1.13 mL, 1.0 M, 1.134 mmol). The resulting solution was stirred at RT for 20 h, then was concentrated under reduced pressure. The crude residue was diluted with water (10 mL) and washed with ether (2×10 mL). The aqueous solution was lyophilized to obtain the desired compound (240 mg) as a pale yellow solid. MS (m/z) 374 (M+1).

Example 2a and 2b

Preparation of rac. (5Z)-7-(-3-chloro-1-{4-[1-(cyclopropyl-methyl)cyclobutyl]-4-hydroxybutyl}pyrrolidin-2-yl)hept-5-enoic Acid (Scheme 2, Steps A-B and D-F)

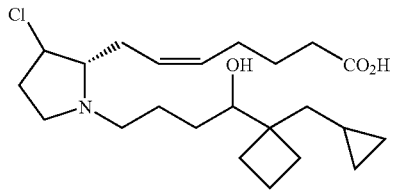

Intermediate 2.1: 1-(cyclopropylmethyl)cyclobutanecarboxylic acid

To a solution of LDA (100 ml, 2.0 M THF solution) in THF (100 ml) was added dropwise over a period of 20 minutes at 0° C., a solution of cyclobutane carboxylic acid (10 g, 0.1 mol) in THF (15 ml). The resulting mixture was stirred at RT for 2 h then bromoethyl cyclopropane (15 g, 0.11 mol) was added dropwise and the mixture was stirred at RT overnight. To the reaction mixture was added 2N HCl and the mixture was extracted with EtOAc. The organic layer was washed with water and brine to afford the title compound as light yellow oil (19.2 g), which was used in the next step without purification.

Intermediate 2.2: [1-(cyclopropylmethyl)cyclobutyl] methanol

To a solution of lithium aluminum hydride (150 ml, 1.0 M THF solution) was added dropwise a solution of intermediate 2.1 (19 g) in THF (25 ml) and the mixture was refluxed for 0.5 hours. The reaction mixture was cooled with ice and quenched with the slowly addition of water. The mixture was filtered through celite and the filtrate was concentrated. The crude residue was purified by flash column chromatography (EtOAc/hexane) to afford the title compound (8.83 g) as a colorless oil. $R_f$ 0.40 (EtOAc/hexane 1/5) $^1$H NMR (CDCl$_3$) δ: 0.05 (m, 2H), 0.42 (m, 2H), 0.62 (m, 1H), 1.42 (d, J=6.96 Hz, 2H), 1.78-1.84 (m, 6H), 3.64 (s, 2H).

Intermediate 2.3: tert-butyl({1-[1-(cyclopropylmethyl) cyclobutyl]prop-2-ynyl}-oxy)dimethylsilane.

To a solution of oxalyl chloride (47 ml, 2.0 M solution in DCM) in methylene chloride (100 ml) at −78° C. was added dropwise a solution of DMSO (13.4 ml) in methylene chloride (12 ml) and the mixture was stirred at that temperature for 30 minutes. To this solution was added dropwise a solution of intermediate 2.3 (8.8 g) in methylene chloride (12 ml) and the temperature was raised to −40° C. over a period of 30 minutes. To this solution was added Et$_3$N (53 mL) dropwise and the temperature was raised to 0° C over a period of one hour. To the reaction mixture was added water and 2N HCl and the mixture was extracted with methylene chloride. The organic layer was washed by water and brine, dried over anhydrous magnesium sulfate to afford the desired aldehyde as yellow oil, which will be used in the next step quickly without purification. $R_f$ 0.7 (EtOAC/hexane 1/5).

To a solution of the aldehyde intermediate in THF (50 ml) at 60° C. was added dropwise ethynylmagnesium bromide (400 ml, 0.5 M in THF solution) and the solution was stirred for 30 minutes allowing the temperature to reach 0° C. The reaction was quenched at −60° C. with saturated ammonium chloride solution (40 ml) and warmed to RT. The aqueous layer was extracted with EtOAc (2×). The combined organic portions were washed with brine, dried over magnesium sulfate, filtered, and concentrated to afford the desired alcohol as s light yellow oil, which was used quickly in the next step without purification.

To a solution of the alcohol intermediate (7.86 g, 0.048 mol) in dry DMF (160 mL) was added imidazole (16.25 g, 0.34 mol) and tert-butyldimethylsilyl chloride (18.0 g, 0.119 mol). The mixture was stirred at room temperature then was quenched with saturated aqueous solution of ammonium chloride and diluted with ethyl acetate. The organic layer was washed with saturated ammonium chloride, water, brine, dried over sodium sulfate, and evaporated in vacuo to give an oily residue which was purified by flash column chromatography to afford the title compound (3.44 g) as colorless oil. $^1$H NMR (CDCl$_3$) δ: 0.10 (m, 2H), 0.11 (s, 3H), 0.15 (s, 3H), 0.44 (d, J=7.69 Hz, 2H), 0.71 (m, 1H), 0.91 (s, 9H), 1.36 (d, J=Hz, 2H), 1.80 (m, 4H), 2.08 (m, 2H), 2.30 (s, 1H), 4.40 (s, 1H).

Intermediate 2.4: 4-{[tert-butyl(dimethyl)silyl]oxy}-4-[1-(cyclopropylmethyl)cyclobutyl]but-2-yn-1-ol.

To a solution of intermediate 2.3 (3.44 g, 12.4 mmol) in THF (100 ml) at −78° C. was added dropwise n-BuLi (9.3 ml, 1.6 M in hexane) over a period of 10 minutes. The reaction mixture was stirred for 30 minutes before paraformaldehyde (1.49 g, 49.6 mmol) was added in one portion. After the mixture was stirred for 10 minutes, the cooling bath was removed and the mixture was stirred at RT for 18 hours. The resulting mixture was treated with saturated ammonium chloride and EtOAc. The organic layer was washed with water and brine, dried with magnesium sulfate, concentrated and purified by flash column chromatography to afford the title compound (2.37 g, 52%) as colorless oil. $R_f$ 0.6 (EtOAc/hexane 1/4) $^1$H NMR (CDCl$_3$) δ: 0.10 (m, 2H), 0.11 (s, 3H), 0.15 (s, 3H), 0.44 (m, 2H[), 0.71 (m, 1H), 0.91 (s, 9H), 1.31 (m, 1H), 1.62 (m, 1H), 2.04 (m, 4H), 4.28 (s, 2H), 4.43 (s, 1H).

Intermediate 2.5: 4-{[tert-butyl(dimethyl)silyl]oxy}-4-[1-(cyclopropylmethyl)-cyclobutyl]butan-1-ol.

A heterogeneous mixture of intermediate 2.4 (2.3 g) and 10% Pd/C (catalytic amount) in MeOH (20 mL) was stirred in an atmosphere of hydrogen for 3 h. The solvent was filtered via celite, concentrated in vacuo to give a residue used in the next step without further purification (2.2 g, 95%): $R_f$ 0.10 (EtOAc/hexane 1/9).

Intermediate 2.6: 4-{[tert-butyl(dimethyl)silyl]oxy}-4-[1-(cyclopropylmethyl)-cyclobutyl]butanal.

A solution of oxalyl chloride in DCM (10 mL, 2.0 M, 2.1 mmol) was diluted with dry DCM (10 mL) and cooled to −70° C. and a solution of DMSO (0.18 mL, 2.6 mmol) in DCM (5 mL) was added dropwise. After 15 min., to the above solution was added dropwise a solution of intermediate 2.5 (0.50 g, 1.6 mmol) in DCM (5 mL). The resulting solution was stirred at −78° C. for 45 min. then Et$_3$N (1.1 mL, 8.0 mmol) was added and the solution was warmed to RT. After 15 min. the solution was diluted with DCM (50 mL) and washed with a saturated solution of NH4Cl (2×50 mL), brine (50 mL), dried over sodium sulfate and concentrated in vacuo to afford the aldehyde intermediate (0.37 g, 80%) used in the next step without further purification. $R_f$ 0.40 (EtOAc/hexane 1/9).

Intermediate 2.7: rac. Methyl (5Z)-7-((2R,3R)-1-{4-{[tert-butyl(dimethyl)silyl]-oxy}-4-[1-(cyclopropylmethyl)cyclobutyl]butyl}-3-chloropyrrolidin-2-yl)hept-5-enoate.

To a solution of intermediate 2.6 (0.37 g, 1.16 mmol) and intermediate 1.9 (0.28 g, 1.16 mmol) in MeOH (10 mL) was added a solution of NaCNBH$_3$ in THF (2.3 mL, 1.0 M, 2.32 mmol). The resulting solution was stirred at RT for 18 h then was concentrated in vacuo, diluted with EtOAc (50 mL) and washed with a saturated solution of NaHCO$_3$ (50 mL), and brine (50 mL). The organic solution was dried over sodium sulfate and concentrated in vacuo. The crude residue was subjected to flash chromatography and was eluted with EtOAc/hexane to afford the desired intermediate (0.64 g, 99%) as colorless oil. $R_f$ 0.60 (EtOAc/hexane 1/4); MS (m/z): 540 (M+1).

Intermediate 2.8 and 2.9: rac. Methyl (5Z)-7-(3-chloro-1-{4-[1-(cyclopropyl-methyl)cyclobutyl-]4-hydroxybutyl}pyrrolidin-2-yl)hept-5-enoate.

Intermediate 2.7 (0.64 g, 1.19 mmol) was diluted with HCl in dioxane solution (10 mL. 4M). The solution was stirred at 0° C. for 2 h then concentrated under reduced pressure. The crude residue was diluted with EtOAc (50 mL) and washed with a saturated solution of NaHCO$_3$ (20 mL) and brine (20 mL). The organic phase was dried over sodium sulfate and concentrated under reduced pressure. Silica gel column chromatography eluted with EtOAc/hexane allowed the separation of the two diastereoisomers intermediate. Intermediate 2.8 (first isomer, 70 mg): $R_f$ 0.4 (EtOAc/hexane 1/1); Intermediate 2.9 (second isomer, 90 mg): $R_f$ 0.35 (EtOAc/hexane 1/1).

The title compound, (52)-7-(−3-chloro-1-{4-[1-(cyclopropylmethyl)cyclobutyl]-4-hydroxybutyl}pyrrolidin-2-yl)hept-5-enoic acid, was then prepared as follows. To a solution of intermediate 2.8 (81 mg, 0.19 mmol) in MeOH (0.9 mL) and THF (0.9 mL) was added a solution of NaOH in water (0.29 mL, 1.0 M, 0.29 mmol). The resulting solution was stirred at RT for 20 h, and then was concentrated under reduced pressure. The crude residue was diluted with water (10 mL) and washed with ether (2×10 mL). The aqueous solution was lyophilized to obtain the desired compound (50 mg) as a pale yellow solid.

The title compound, rac. (5Z)-7-(−3-chloro-1-{4-[1-(cyclopropylmethyl)cyclobutyl]-4-hydroxybutyl}pyrrolidin-2-yl)hept-5-enoic acid, was then prepared as follows. To a solution of intermediate 2.9 (100 mg, 0.23 mmol) in acetonitrile (5 mL) was added hydrochloric acid (5 mL, 6M solution). The resulting solution was stirred at RT for 24 h then lyophilized to afford the desired compound (110 mg) as a white solid. MS (m/z) 413 (M+1).

Example 3

Preparation of rac. (5Z)-7-{(3R)-3-chloro-1-[(2E)$_4$-hydroxynon-2-enyl]pyrrolidin-2-yl}hept-5-enoic acid (scheme 2, steps A, B, I, E, and F)

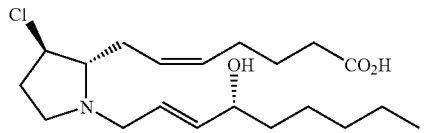

Intermediate 3.1: (2E)-4-{[tert-butyl(dimethyl)silyl]oxy}non-2-en-1-ol.

To a solution of intermediate (R)-1.11 (236.1 mg, 0.874 mmol) in ether (5.0 mL), cooled in an ice-water bath, was added a solution of sodium bis(2-methoxyethoxy) aluminum hydride (Red-A1) in toluene (0.320 mL, 65% wt. in toluene) by syringe dropwise. The mixture is stirred for 5 h and the reaction quenched with a Rochelle salt, diluted with ethyl acetate (20 mL). The organic layer is washed with water, brine, dried over sodium sulfate, evaporated to give a colorless oily residue (0.216 g, 0.794 mmol, 90.8%). $R_f$ 0.10 (EtOAc/hexane 1/9).

Intermediate 3.2: {[(2E)-4-bromo-1-pentylbut-2-enyl]oxy}(tert-butyl)di-methylsilane.

To a solution of intermediate 3.1 (0.216 g, 0.794 mmol, 1.0 eq) in DCM (9.0 mL, 0.12 M) were added CBr$_4$ (0.289 g, 0.873 mmol, 1.1 eq) followed by PPh$_3$ (0.249 g, 0.952 mmol, 1.2 eq). The resulting solution was stirred at RT for ½ h and then concentrated in vacuo. The crude product was purified by flash column chromatography (hexanes) to afford fractions of the desired compound (0.208 g, 0.622 mmol, 78.40%) as a colorless oil. $R_f$ 0.68, (EtOAc/hexanes 1/9).

Intermediate 3.3: rac. Methyl (5Z)-7-{(3R)-3-chloro-1-[(2E)-4-(1,1,2,2, -tetra-methylpropoxy)non-2-enyl]pyrrolidin-2-yl}hept-5-enoate.

To a solution of intermediate 3.2 (0.175 g, 0.524 mol) in DMF (3.0 mL, 0.1 M) were added the intermediate 1.9 (0.130 g, 0.524 mmol) and K$_2$CO$_3$ (275 mg, 1.99 mmol). The resulting mixture was stirred at 60° C. for 18 h and then diluted with EtOAc (25 mL). The organic layer was washed with a saturated solution of NH$_4$Cl (2×10 mL), water (4×10 mL), brine (2×10 mL), dried over sodium sulfate, filtered, and evaporated in vacuo to give a crude product (311.2 mg) which on flash column chromatography (EtOAc/hexanes 3/7) gave fractions of the desired compound (241.2 mg, 0.483 mmol, 92.2%) as a yellow oil, $R_f$ 0.68, (EtOAc/hexanes 1/9).

Intermediate 3.4: rac. Methyl (5Z)-7-{(3R)-3-chloro-1-[(2E)-4-hydroxynon-2-enyl]pyrrolidin-2-yl}hept-5-enoate.

Intermediate 3.3 (122.0 mg, 0.236 mmol) was dissolved in a 4M HCl solution in dioxane (10 mL). The resulting solution was stirred for 1 hr at RT and then concentrated in vacuo to afford the title compound (0.10 g, 97.5%).

The title compound, rac. (5Z)-7-{(3R)-3-chloro-1-[(2E)-4-hydroxynon-2-enyl]-pyrrolidin-2-yl}hept-5-enoic acid, was then prepared as follows. To a solution of intermediate 3.4 (93.0 mg, 0.241 mmol) in MeOH (1.1 mL), THF (1.1 mL), and 1M solution of NaOH in water (0.36 mL, 0.362 mol). The resulting solution was stirred at RT for 18 h then concentrated under reduced pressure to give the sodium salt. The sodium salt was dissolved in water (10 mL) and organic residue extracted with EtOAc (10 mL×2). The water layer was concentrated on a rotary evaporator to give a solid residue. This residue was dissolved in water and subjected to lyophilized to afford the title compound (55.4 mg, 0.123 mmol, 49%/0) as a colorless oil. MS (m/z) 372 (M+1).

Example 4

Preparation of: rac. (5Z)-7-{(3R)-3-chloro-1-[(2Z)-4-hydroxynon-2-enyl]pyrrolidin-2-yl}hept-5-enoic acid (Scheme 2, Steps A, B, I, E, and F)

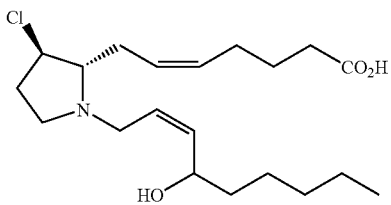

Intermediate 4.1: (2Z)-4 {[tert-butyl(dimethyl)siloxy]oxy}non-2-en-1-ol.

To a solution of intermediate 1.11 (423.3 mg, 1.556 mmol), in DCM (20.0 mL) was hydrogenated in the presence of Pd/CaCO3/lead (42.5 mg, Lindlar catalyst). The heterogeneous mixture is stirred for 3.5 h and then filtered via celite. The filtrate is evaporated to give a glassy residue (0.354 g, 1.29 mmol, 83.2%). $R_f$ 0.10 (EtOAc/hexane 1/9).

The title compound, rac. (5Z)-7-{(3R)-3chloro-1-[(2Z)$_4$-hydroxynon-2-enyl]pyrrolidin-2-yl}hept-5-enoic acid was then prepared from intermediate 4.1 and intermediate 1.9 using the procedure of Example 3. MS (m/z) 372 (M+1).

Example 5a and 5b

Preparation of methyl(5Z)-7-[(2R)-1-(3-hydroxyoctyl)-3-oxopyrrolidin-2-yl]hept-5-enoate (Scheme 1, Steps A-H)

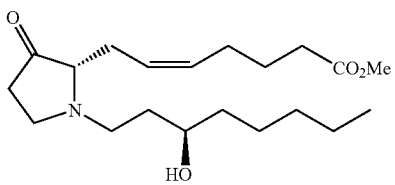

Intermediate 5.1: tert-butyl 2-[(2Z)-7-methoxy-7-oxohept-2-enyl]-3-oxo-pyrrolidine-1-carboxylate.

A DCM solution of oxalyl chloride (1.0 mL, 2.0 M, 2.0 mmol) was diluted with dry DCM (15 mL) and cooled to −70° C. then a solution of DMSO (0.17 mL, 2.44 mmol) in DCM. (7 mL) was added dropwise. After 15 min. to this solution was added dropwise a solution of intermediate 1.6 (0.5 g, 1.53 mmol) in DCM (7 mL). The resulting solution was stirred at −70° C. for 45 min. then Et$_3$N (1.06 mL, 7.6 mmol) was added dropwise and the solution warmed to RT. After 15 min. the solution was diluted with DCM (50 mL) and washed with a saturated solution of NH4 Cl (2×50 mL), brine (50 mL), dried over sodium sulfate and concentrated in vacuo to afford the aldehyde intermediate (0.49 g, 98%) used in the next step without further purification. $R_f$ 0.75 (EtOAc/hexane 1/1); $^1$H NMR (CDCl$_3$) δ 1.48 (s, 9H), 1.50-1.75 (m, 4H), 2.00-2.15 (m, 2H), 2.28 (t, 2H), 2.35-2.70 (m, 4H), 3.45-3.55 (m, 1H), 3.65 (s, 3H), 3.90-4.05 (m, 2H), 5.25-5.55 (m, 2H).

Intermediate 5.2: methyl(5Z)-7-(3,3-dimethoxypyrrolidin-2-yl)hept-5-enoate.

A solution of intermediate 5.1 (200 mg, 0.62 mmol), trimethyl orthoformate (0.86 mL, 7.86 mmol), and H$_2$SO$_4$ (0.03 mL) in MeOH (3 mL) was stirred at RT for 24 h. The solution was then concentrated in vacuo, diluted with EtOAc (50 mL) and washed with saturated solution of NaHCO$_3$ (30 mL), and brine (30 mL). The organic solution was dried and concentrated under reduced pressure to afford the desired intermediate (160 mg, 98%) as a pale yellow oil used in the next step without purification. $^1$H NMR (CDCl$_3$) a 1.60-1.74 (m, 2H), 1.80-2.20 (m, 6H), 2.22-2.38 (m, 3H), 2.85-2.95 (m, 1H), 2.96-3.07 (m, 1H), 3.20 (s, 3H), 3.26 (s, 3H), 3.67 (s, 3H), 5.35-5.55 (m, 2H); MS (m/z) 272 (M+1).

Intermediate 5.3: methyl(5Z)-7-[(2S)-3,3-dimethoxypyrrolidin-2-yl]hept-5-enoate.

To a solution of intermediate 5.2 (1.50 g, 5.5 mmol) in i-PrOH (13 mL) was added a solution of D-tartaric acid (0.83 g, 5.5 mmol) in i-PrOH (12 mL). The mixture was stirred at RT for 2 h then at 0 C for 30 min. The white precipitate was filtered out and washed with small amount of i-PrOH. The residue was diluted with EtOAc and washed with a saturated solution of NaHCO$_3$, brine, dried and concentrated in vacuo to afford the desired chiral amine (0.38 g).

Intermediate 5.4: methyl(5Z)-7-[(2S)-3,3-dimethoxy-1-(3-oxooctyl)pyrrolidin-2-yl]hept-5-enoate.

To a solution of intermediate 5.3 (100 mg, 0.37 mmol) in MeOH (10 mL) was added 1-octen-3-one (0.17 mL, 1.11 mmol). The resulting solution was stirred at reflux for 2 h, then was concentrated in vacuo. The crude residue was subjected to flash chromatography and was eluted with EtOAc/hexane to afford the desired intermediate (130 mg, 89%) as colorless oil. $R_f$ 0.75 (EtOAc/hexane 1/1); $^1$H NMR (CDCl$_3$) δ 0.87 (t, 3H), 1.20-1.35 (m, 4H), 1.63-1.75 (m, 2H), 1.80-2.00 (m, 2H), 2.00-2.15 (m, 4H), 2.20-2.60 (m, 10H), 2.95-3.10 (m, 2H), 3.13 (s, 3H), 3.20 (s, 3H), 3.65 (s, 3H), 5.31-5.58 (m, 2H); MS (m/z) 398 (M+1).

Intermediate 5.5 and 5.6: methyl(5Z)-7-[(2S)-1-(3-hydroxyoctyl)-3,3-di-methoxypyrrolidin-2-yl]hept-5-enoate.

To a mixture of intermediate 5.4 (0.12 g, 0.30 mmol) in MeOH (4 mL) and water (5 mL) were added CeCl$_3$ (75 mg, 0.30 mmol) followed by NaBH$_4$ (23 mg, 0.60 mmol). After 1 h the reaction was diluted with EtOAc (20 mL) and washed with a saturated solution of NaHCO$_3$ (20 mL), brine (20 mL), dried and concentrated in vacuo to afford a mixture of the 2 diastereoisomers intermediate that were separated by silica gel flash column chromatography (EtOAc/hexane). Intermediate 5.5 (50 mg): $R_f$ 0.30 (EtOAc/hexane 1/1); $^1$H NMR (CDCl$_3$) δ 0.87 (t, 3H), 1.20-1.50 (m, 10H), 1.51-1.86 (m, 4H), 1.90-2.00 (dd, 1H), 2.05-2.20 (m, 4H), 2.30-2.45 (m, 4H), 2.50-2.60 (m, 1H), 2.90-3.02 (m, 1H), 3.11 (s, 3H), 3.20 (s, 3H), 3.25 (t, 1H), 3.64 (s, 3H), 3.66-3.80 (m, 1H), 5.33-5.57 (m, 2H); MS (m/z) 400 (M+1). Intermediate 5.6 (50 mg): $R_f$ 0.20 (EtOAc/hexane 1/1); $^1$H NMR (CDCl$_3$) δ 0.85 (t, 3H), 1.20-1.55 (m, 10H), 1.61-1.80 (m, 4H), 1.92-2.20 (m, 4H), 2.22-2.40 (m, 3H), 2.45-2.60 (m, 2H), 2.90-

3.02 (m, 1H), 3.11 (s, 3H), 3.20 (s, 3H), 3.12 (t, 1H), 3.64 (s, 3H), 3.66-3.80 (m, 1H), 5.33-5.57 (m, 2H); MS (m/z) 400 (M+1).

The title compound, methyl(5Z)-7-[(2R)-1-(3-hydroxyoctyl)-3-oxopyrrolidin-2-yl]hept-5-enoate, was then prepared as follows. To a solution of intermediate 3.7 (50 mg, 0.13 mmol) in THF (2 mL) and $H_2O$ (0.2 mL) was added a solution of HCl in dioxane (2 mL, 4M solution). The resulting solution was stirred at room temperature for 2 hours then concentrated in vacuo to afford the desired compound (29 mg, 66%). MS (m/z) 354 (M+1).

The title compound, methyl(5Z)-7-[(2R)-1-(3-hydroxyoctyl)-3-oxopyrrolidin-2-yl]hept-5-enoate, was then prepared as follows. To a solution of intermediate 3.8 (50 mg, 0.13 mmol) in THF (2 mL) and $H_2O$ (0.2 mL) was added a solution of HCl in dioxane (2 mL, 4M solution). The resulting solution was stirred at $R_T$ 2 h then concentrated in vacuo to afford the desired compound (32 mg, 70%/O). MS (m/z) 354 (M+1).

Example 6

Preparation of rac. 4-{[3-chloro-1-(3-hydroxyoctyl) pyrrolidin-2-yl]methoxy}benzoic acid (Scheme 3, Steps A-F)

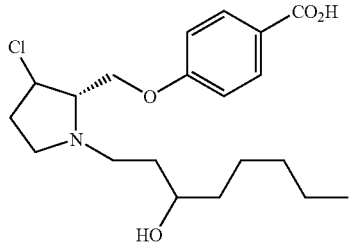

Intermediate 6.1: rac. 1-tert-butyl 2-ethyl (2R,3S)-3-hydroxypyrrolidine-1,2-dicarboxylate.

To a solution of the 3-oxopyrrolidine-1,2-dicarboxylic acid 1-tert-butyl ester 2-ethyl ester (obtained from diethyl 3-azahexane-1,6-dicarboxylate according to the procedure of Cooper, J. et al. *J. Chem. Soc. Perkin Trans.* 1, 1993, 1313-1317) (15.0 g, 0.058 mol) in THF (600 mL) cooled at −78° C. was added dropwise a THF solution of L-Selectride (58 mL, 1 M, 0.058 mol). The solution was stirred at −78° C. for 1 h then the reaction was quenched with hydrogen peroxide solution (35 mL, 30%) and the reaction mixture was allowed to warm up to 0° C. The reaction was then diluted with EtOAc and washed with HCl 1M, brine, dried over sodium sulfate and concentrated in vacuo. The crude residue was purified by silica gel flash column chromatography using EtOAc/hexane as eluent to afford the desired intermediate (10 g, 66%) as a colorless oil. $R_f$ 0.50 (EtOAc/hexane 4/1); $^1$H NMR (CDCl$_3$) δ 1.20-1.35 (t, 3H), 1.44 (s, 9H), 1.95-32 (m, 2H), 3.40-3.70 (m, 2H), 4.10-4.42 (m, 3H), 4.55-4.65 (m, 1H); MS (m/z) 260 (M+1).

Intermediate 6.2: 1-tert-butyl 2-ethyl 3-{[(4-methylphenyl)sulfonyl]oxy}pyrrolidine-1,2-dicarboxylate.

To a solution of intermediate 6.1 (7.0 g, 0.028 mol) in pyridine (50 mL) cooled at 0 C was added portionwise p-toluenesulfonyl chloride (10.4 g, 0.054 mol). The resulting solution was stirred at RT for 20 h then concentrated in vacuo. The crude residue was diluted with EtOAc (200 mL) and washed with HCl 1M (200 mL), water (100 mL), saturated solution of NaHCO$_3$ (200 mL), and brine (200 mL). The organic solution was dried and concentrated under reduced pressure. The crude mixture was purified by silica gel flash column chromatography using EtOAc/hexane as eluent to afford the desired intermediate (7.2 g, 63%) as a colorless oil. $R_f$ 0.50 (EtOAc/hexane 3/7); $^1$H NMR (CDCl$_3$) δ 1.25 (t, 3H), 1.38 (s, 9H), 2.00-2.30 (m, 2H), 2.44 (s, 3H), 3.40-3.70 (m, 2H), 4.05-4.25 (m, 2H), 4.41 (d, 1H), 5.10-5.20 (m, 1H), 7.34 (d, 2H), 7.76 (d, 2H).

Intermediate 6.3: 1-tert-butyl 2-ethyl 3-chloropyrrolidine-1,2-dicarboxylate.

To a solution of intermediate 6.2 (7.2 g, 0.017 mol) in toluene (500 mL) was added tetrabutylammonium chloride (48 g, 0.174 mol). The solution was stirred at 60 C for 24 h then diluted with EtOAc (1500 mL) and washed with water (3×), saturated solution of NaHCO$_3$ (2×), and brine (1×). The organic solution was dried and concentrated in vacuo to afford the desired intermediate (5.8 g) as a pale yellow oil used in the next step without further purification. $R_f$ 0.70 (EtOAc/hexane 3/7); $^1$H NMR (CDCl$_3$) δ 1.25-1.32 (m, 3H), 1.44 (s, 9H), 2.10-2.20 (m, 1H), 2.30-2.42 (m, 1H), 3.60-3.75 (m, 2H), 4.15-4.25 (m, 2H), 4.37-4.65 (m, 2H).

Intermediate 6.4: tert-butyl 3-chloro-2-(hydroxymethyl) pyrrolidine-1-carboxylate.

To a solution of intermediate 6.3 (5.8 g, 0.021 mol) in THF (36 mL) and MeOH (4 mL) was added portionwise NaBH$_4$ (0.95 g, 0.025 mol). The resulting mixture was stirred at RT for 1 h then was diluted with EtOAc (150 mL) and washed with a saturated solution of NaHCO$_3$ and brine. The organic solution was dried over sodium sulfate and concentrated in vacuo. The crude residue was purified by silica gel flash column chromatography using EtOAc/hexane as eluent to afford the desired intermediate (3.0 g, 75% from intermediate #0.2) as a colorless oil. $R_f$ 0.30 (EtOAc/hexane 1/1); $^1$H NMR (CDCl$_3$) δ 1.51 (s, 9H), 2.05-2.15 (m, 1H), 2.30-2.42 (m, 1H), 3.40-3.80 (m, 5H), 4.00-4.30 (m, 2H).

Intermediate 6.5: tert-butyl-3-chloro-2-{[4-(methoxycarbonyl)phenoxy]methyl}pyrrolidine-1-carboxylate.

To a solution of intermediate 6.4 (250 mg, 1.06 mmol), 4-hydroxybenzoate (161 mg, 1.06 mmol), and triphenylphosphine (307 mg, 1.17 mmol) in THF (10 mL) was added DEAD (0.18 mL, 1.17 mmol). The resulting solution was stirred at RT for 18 h then concentrated under reduced pressure. The crude residue was subjected to flash chromatography and was eluted with EtOAc/hexane to afford the desired intermediate (80 mg, 20%) as a colorless oil. $R_f$ 0.75 (EtOAc/hexane 3/7); $^1$H NMR (CDCl$_3$) δ 1.51 (s, 9H), 2.10-2.20 (m, 1H), 2.40-2.55 (m, 1H), 3.45-3.80 (m, 2H), 3.87 (s, 3H), 3.90-4.10 (m, 1H), 4.14-4.40 (m, 2H), 4.50-4.60 (m, 1H), 6.93 (d, 2H), 7.96 (d, 2H).

Intermediate 6.6: Methyl 4-[(3-chloropyrrolidin-2-yl) methoxy]benzoate.

Intermediate 6.5 (60 mg, 0.162 mmol) was dissolved in a solution of HCl in dioxane (2 mL, 4M HCl solution). The resulting mixture was stirred at RT for 1 h then concentrated in vacuo to afford the desired intermediate (50 mg, 98%) used in the next step without purification. MS (m/z) 270 (M+1).

Intermediate 6.7: Methyl 4-{[3-chloro-1-(3-oxooctyl)pyrrolidin-2-yl]-methoxy}benzoate.

To a solution of intermediate 6.6 (50 mg, 0.162 mmol) in EtOH (5 mL) were added 1-octen-3-one (0.072 mL, 0.49 mmol) and Et$_3$N (0.090 mL, 0.65 mmol). The resulting solution was stirred at reflux for 2 h, then was concentrated in vacuo. The crude residue was subjected to flash chromatography and was eluted with EtOAc/hexane to afford the desired intermediate (60 mg, 90%) as a colorless oil. $R_f$ 0.70

(EtOAc/hexane 3/7); $^1$H NMR (CDCl$_3$) δ 0.85 (t, 3H), 1.15-1.35 (m, 4H), 1.50-1.60 (m, 2E[), 2.00-2.10 (m, 1H), 2.25-2.40 (m, 1H), 2.40 (t, 2H), 2.50-2.70 (m, 2H), 2.70-2.87 (m, 2H), 3.10-3.30 (m, 3H), 3.82 (dd, 1H), 3.87 (s, 3H), 3.97 (dd, 1H), 4.28-4.35 (m, 1H), 6.90 (d, 2H), 7.97 (d, 2H); MS (m/z) 396 (M+1).

Intermediate 6.8: Methyl 4-{[3-chloro-1-(3-hydroxyoctyl)pyrrolidin-2-yl]methoxy}benzoate.

To a mixture of intermediate 6.7 (0.1 g, 0.25 mmol) in EtOH (3 mL) and water (3 mL) were added CeCl$_3$ (62 mg, 0.25 mmol) followed by NaBH$_4$ (15 mg, 0.38 mmol). After 1 h the reaction was diluted with EtOAc (20 mL) and washed with a saturated solution of NaHCO$_3$ (20 mL), brine (20 mL), dried and concentrated in vacuo to afford a mixture of the 2 diastereoisomers intermediate (80 mg, 80%) used in the next step without further purification. R$_f$ 0.50 and 0.45 (EtOAc/hexane 1/1); MS (m/z) 398 (M+1).

The title compound, 4-{[3-chloro-1-(3-hydroxyoctyl)pyrrolidin-2-yl]methoxy}benzoic acid, then was prepared as follows. To a solution of intermediate 6.8 (80 mg, 0.20 mmol) in water (0.4 mL), MeOH (1.2 mL), and THF (1.2 mL) was added NaOH (32 mg, 0.8 mmol). The resulting solution was stirred at room temperature for 5 h then to concentrated under reduced pressure. The crude mixture was purified by RP-HPLC using ACN/H$_2$O/0.1% TFA to afford the desired compound (150 mg, 600%) as a colorless oil. $^1$H NMR (D20) δ 0.75-0.85 (m, 3H), 1.15-1.50 (m, 4H), 1.75-2.05 (m, 2H), 2.40-2.50 (m, 1), 2.64-2.75 (m, 1H), 3.40-3.75 (m, 5H), 3.90-4.00 (m, 1H), 4.25-4.35 (m, 1H), 4.40-4.50 (m, 1H), 4.55-4.65 (m, 1H), 7.09 (d, 2H), 8.01 (d, 2H); MS (m/z) 384 (M+1).

Example 7a and 7b

Synthesis of 5-({[3-chloro-1-(3-hydroxyoctyl)pyrrolidin-2-yl]methoxy}methyl)-2-furoic acid (Scheme 3, Steps A-C and M-N)

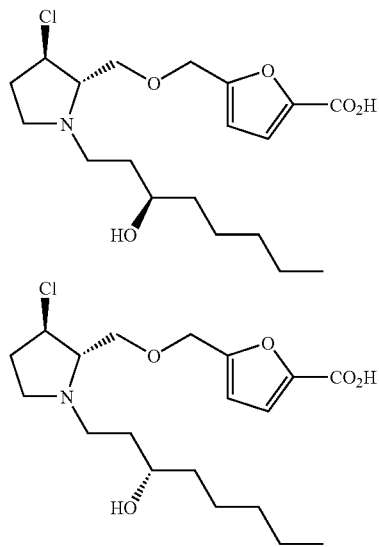

Intermediate 7.1: tert-butyl 3-chloro-2-({[5-(methoxycarbonyl)-2-furyl]methoxy}methyl)pyrrolidine-1-carboxylate.

NaH (36 mg, 0.89 mmol) was added portionwise and at 0 C to a solution of intermediate 4.4 (200 mg, 0.85 mmol) in DMF (5.0 mL). After 10 min., methyl 5-bromomethylfuran-2-carboxylate (300 mg, 1.27 mmol) was added. The resulting solution was stirred at RT for 20 h then was diluted with ether (50 mL) and washed with HCl 1N (30 mL), water (30 mL), and brine (30 mL). The organic solution was dried and concentrated in vacuo. The crude residue was subjected to flash chromatography and was eluted with EtOAc/hexane to afford the desired intermediate (200 mg, 63%) as a colorless oil. R$_f$ 0.50 (EtOAc/hexane 3/7); $^1$H NMR (CDCl$_3$) δ 1.45 (s, 9H), 2.00-2.12 (m, 1H), 2.30-2.45 (m, 1H), 3.30-3.70 (m, 4H), 3.88 (s, 3H), 3.95-4.15 (m, 1H), 4.42-4.51 (m, 1H), 4.51 (s, 2H), 6.41 (s, 1H), 7.13 (s, 1H).

Intermediate 7.2: Methyl 5-{[(3-chloropyrrolidin-2-yl)methoxy]methyl}-2-furoate.

Intermediate 7.1 (200 mg, 0.54 mmol) was dissolved in a solution of HCl in dioxane (3 mL, 4M HCl solution). The resulting solution was stirred at RT for 1 h then concentrated in vacuo to afford the desired intermediate (160 mg, 98%) used in the next step without purification. MS (m/z) 274 (M+1).

Intermediate 7.3: Methyl 5-({[3-chloro-1-(3-oxooctyl)pyrrolidin-2-yl]methoxy}methyl)-2-furoate.

To a solution of intermediate 7.2 (160 mg, 0.54 mmol) in EtOH (10 mL) were added 1-octen-3-one (0.24 mL, 1.61 mmol) and Et$_3$N (0.30 mL, 2.14 mmol). The resulting solution was stirred at reflux for 2 h, then was concentrated in vacuo. The crude residue was subjected to flash chromatography and was eluted with EtOAc/hexane to afford the desired intermediate (200 mg, 97%) as a colorless oil. R$_f$ 0.75 (EtOAc/hexane 1/1); $^1$H NMR (CDCl$_3$) δ 0.87 (t, 3H), 1.18-1.35 (m, 4H), 1.50-1.62 (m, 2H), 1.94-2.00 (m, 1H), 2.18-2.30 (m, 1H), 2.39 (t, 2H), 2.54-2.76 (m, 4H), 2.82-2.92 (m, 1H), 3.04-3.18 (m, 2H), 3.34-3.40 (dd, 1H), 3.45-3.52 (dd, 1H), 3.88 (s, 3H), 4.18-4.26 (m, 1H), 4.52 (s, 2H), 6.42 (s, 1H), 7.12 (s, 1H); MS (m/z) 400 (M+1).

Intermediate 7.4 and 7.5: Methyl 5-({[3-chloro-1-(3-hydroxyoctyl)pyrrolidin-2-yl]methoxy}methyl)-2-furoate.

To a mixture of intermediate 7.3 (0.19 g, 0.48 mmol) in EtOH (6 mL) and water (6 mL) were added CeCl$_3$ (117 mg, 0.48 mmol) followed by NaBH$_4$ (27 mg, 0.71 mmol). After 1 h the reaction was diluted with EtOAc (20 mL) and washed with a saturated solution of NaHCO$_3$ (20 mL), brine (20 mL), dried and concentrated in vacuo to afford a mixture of the 2 diastereoisomers intermediate that were separated by silica gel flash column chromatography (EtOAc/hexane). Intermediate 7.4 (70 mg): R$_f$ 0.30 (EtOAc/hexane 1/1); MS (m/z) 402 (M+1). Intermediate 7.5 (80 mg): R$_f$ 0.25 (EtOAc/hexane 1/1); MS (m/z) 402 (M+1).

The title compound, 5-({[3-chloro-1-(3-hydroxyoctyl)pyrrolidin-2-yl]methoxy}methyl)-2-furoic acid, then was prepared as follows. To a solution of intermediate 7.4 as (70 mg, 0.17 mmol) in water (0.4 mL), MeOH (1.2 mL), and THF (1.2 mL) was added NaOH (27 mg, 0.70 mmol). The resulting solution was stirred at RT for 4 h then was acidified with HCl 1N and concentrated under reduced pressure. The crude mixture was purified by RP-HPLC using ACN/H$_2$O/0.1% TFA to afford the desired compound (54 mg) as a colorless oil. $^1$H NMR (CD3OD) δ 0.85-0.95 (t, 3H), 1.2-1.55 (m, 8H), 1.70-1.95 (m, 2H), 2.30-2.42 (m, 1H), 2.50-2.65 (m, 1H), 3.35-4.00 (m, 8H), 4.50-4.60 (m, 1H), 4.67 (s, 2H), 6.62 (s, 1H), 7.18 (s, 1H); MS (m/z) 388 (M+1).

The title compound, 5-({[3-chloro-1-(3-hydroxyoctyl)pyrrolidin-2-yl]methoxy}methyl)-2-furoic acid, then was prepared as follows. To a solution of intermediate 7.5 (80 mg, 0.20 mmol) in water (0.4 mL), MeOH (1.2 mL), and THF (1.2 mL) was added NaOH (32 mg, 0.80 mmol). The resulting solution was stirred at RT for 4 h then was acidified with HCl 1N and concentrated under reduced pressure. The crude mixture was purified by RP-HPLC using ACN/H₂O/0.1% TFA to afford the desired compound (74 mg) as a colorless oil. ¹H NMR (CD₃OD) δ 0.85-0.95 (t, 3H), 1.20-1.55 (m, 8H), 1.70-1.95 (m, 2H), 2.30-2.42 (m, 1H), 2.50-2.65 (m, 1H), 3.35-4.00 (m, 8H), 4.50-4.60 (m, 1H), 4.60 (s, 2H), 6.62 (s, 1H), 7;18 (s, 1); MS (m/z) 388 (M+1).

Example 8a and 8b

Preparation of 4-{2-[3-chloro-1-(3-hydroxyoctyl) pyrrolidin-2-yl]ethyl}benzoic acid (Scheme 3, Steps A-C and G-L)

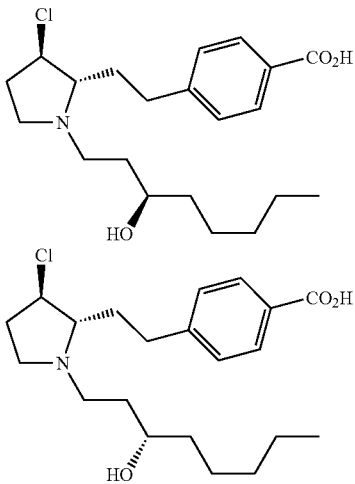

Intermediate 8.1: tert-butyl 3-chloro-2-{(E,Z)-2-[4(methoxycarbonyl)phenyl]vinyl}pyrrolidine-1-carboxylate.

Step A (Swern Oxidation):

A DCM solution of oxalyl chloride (1.4 mL, 2.0 M, 2.77 mmol) was diluted with anhydrous DCM (15 ml) and cooled to −70° C. then a solution of DMSO (0.24 mL, 3.40 mmol) in DCM (7 mL) was added dropwise. After 15 min. to this solution was added dropwise a solution of intermediate 6.4 (0.50 g, 2.13 mmol) in DCM (7 mL). The resulting solution was stirred at −70° C. for 45 min. then Et₃N (1.50 mL, 10.6 mmol) was added dropwise and the solution warmed to RT. After 15 min. the solution was diluted with dichloromethane (50 mL) and washed with a saturated solution of NH₄Cl (2×50 mL), brine (50 mL), dried over sodium sulfate and concentrated in vacuo to afford the aldehyde intermediate (0.49 g, 98%) used in the next step without further purification. R$_f$ 0.37 (EtOAc/hexane 3/7).

Step B (Wittig Reaction):

(4-Methoxycarbonylbenzyl)triphenylphosphonium bromide (1.36 g, 2.77 mmol) was added portionwise and at 0° C. to a solution of NaHMDS (3.0 mL, 1.0 M in THF, 3.0 mmol) in THF (10 mL). After 15 min. was added a solution of the aldehyde intermediate (0.49 g, 2.12 mmol) in THF (10 mL). The resulting mixture was stirred at RT for 18 h then was diluted with EtOAc (600 mL) and washed with HCl 1M solution (60 mL) and brine (60' mL). The organic phase was dried over sodium sulfate and concentrated in vacuo. The crude residue was subjected to flash chromatography and was eluted with EtOAc/hexane to afford the desired olefin intermediate (600 mg, 77%) as colorless oil. R$_f$ 0.45 (EtOAc/hexane 3/7); MS (m/z) 366 (M+1).

Intermediate 8.2: tert-butyl 3-chloro-2-{2-[4-(methoxycarbonyl)phenyl]ethyl}pyrrolidine-1-carboxylate.

A mixture of intermediate 8.1 (500 mg, 1.36 mmol) and Pd/C (cat. Amount) in MeOH (15 mL) was vigorously stirred under H₂ atmosphere (1 atm) for 25 min. Filtration through celite pad and concentration under reduced pressure gave the desired intermediate (500 mg, 98%) as a colorless oil used in the next step without further purification. R$_f$ 0.50 (EtOAc/hexane 3M); ¹H NMR (CDCl₃) δ 1.44 (s, 9H), 1.90-2.40 (m, 2H), 2.65-2.82 (m, 2H), 3.40-3.80 (m, 2H), 3.90 (s, 3H), 4.05-4.30 (m, 1H), 7.23 (d, 2H), 7.95 (d, 2H); MS (m/z) 368 (M+1).

Intermediate 8.3: Methyl 4-[2-(3-chloropyrrolidin-2-yl) ethyl]benzoate.

Intermediate 8.2 (0.5 g, 1.36 mmol) was dissolved in a solution of HCl in dioxane (5 mL, 4M HCl solution). The resulting solution was stirred at RT for 1 h then concentrated in vacuo to afford the desired intermediate (410 mg, 95%) used in the next step without purification. MS (m/z) 268 (M+1).

Intermediate 8.4: Methyl 4-{2-[3-chloro-1-(3-oxooctyl) pyrrolidin-2-yl]ethyl}benzoate.

To a solution of intermediate 8.3 (206 mg, 0.68 mmol) in EtOH (10 mL) were added 1-octen-3-one (0.30 mL, 2.04 mmol) and Et₃N (0.47 mL, 3.40 mmol). The resulting solution was stirred at reflux for 2 h, then was concentrated in vacuo. The crude residue was purified by silica gel flash column chromatography using EtOAc/hexane as eluent to afford the desired intermediate (200 mg, 75%) as a colorless oil. R$_f$ 0.40 (EtOAc/hexane 3/7); MS (m/z) 394 (M+1).

Intermediates 8.5 and 8.6: Methyl 4-{2-[3-chloro-1-(3-hydroxyoctyl)pyrrolidin-2-yl]ethyl}benzoate.

To a mixture of intermediate 8.4 (200 mg, 0.51 mmol) in EtOH (6 mL) and water (6 mL) were added CeCl₃ (125 mg, 0.51 mmol) followed by NaBH₄ (39 mg, 1.02 mmol). After 1 h the reaction was diluted with EtAOc (20 mL) and washed with a saturated solution of NaHCO₃ (20 mL), brine (20 mL), dried and concentrated in vacuo to afford a mixture of the 2 diastereoisomers intermediate that were separated by flash column chromatography (EtOAc/hexane). Intermediate 8.5 (40 mg): R$_f$ 0.50 (EtOAc/hexane 1/1); MS (m/z) 396 (M+1). Intermediate 8.6 (45 mg): R$_f$ 0.45 (EtOAc/hexane 1/1); MS (m/z) 396 (M+1).

The title compound, 4-{2-[3-chloro-1-(3-hydroxyoctyl) pyrrolidin-2-yl]ethyl}benzoic acid, then was prepared as follows. To a solution of intermediate 8.5 (45 mg, 0.11 mmol) in water (0.67 mL), MeOH (2 mL), and THF (2 mL) was added NaOH (50 mg, 1.25 mmol). The resulting solution was stirred at RT for 6 h then concentrated under reduced pressure. The crude mixture was purified by RP-HPLC using ACN/H₂O/0.1% TFA to afford the desired compound (40 mg, 60%) as a colorless oil. ¹H NMR (CD₃OD) δ 0.85-0.95 (m, 3H), 1.20-1.45 (m, 8H), 1.61-1.72 (m, 1H), 1.80-1.95 (m, 1H), 2.03-2.25 (m, 2H), 2.35-2.45 (m, 1H), 2.55-2.70 (m, 1H), 2.80-3.00 (m, 2H), 3.25-3.40 (m, 1H), 3.45-3.95 (m, 5H), 4.67 (br s, 1H), 7.40 (d, 2H), 7.97 (d, 2H); MS (m/z) 382 (M+1).

The title compound, 4-{2-[3-chloro-1-(3-hydroxyoctyl) pyrrolidin-2-yl]ethyl}benzoic acid, then was prepared from intermediate 8.6 using the procedure of Example 8.a. ¹H NMR (CD₃OD) δ 0.85-0.95 (m, 3H), 1.20-1.55 (m, 8H), 1.61-1.85 (m, 2H), 2.02-2.12 (m, 1H), 2.15-2.28 (m, 1H), 2.35-2.45 (m, 1H), 2.55-2.70 (m, 1H), 2.80-3.05 (m, 2H), 3.45-3.95 (m, 6E[), 4.71 (br s, 1H), 7.40 (d, 2H), 7.97 (d, 2H); MS (m/z) 382 (M+1).

Example 9a and 9b

Preparation of (5Z)-7-{(traits-2,33-Chloro-1-[4-hydroxy-4-(1-propylcyclobutyl)butyl]pyrrolidin-2-yl}hept-5-enoic acid (Scheme 2, Steps A-F)

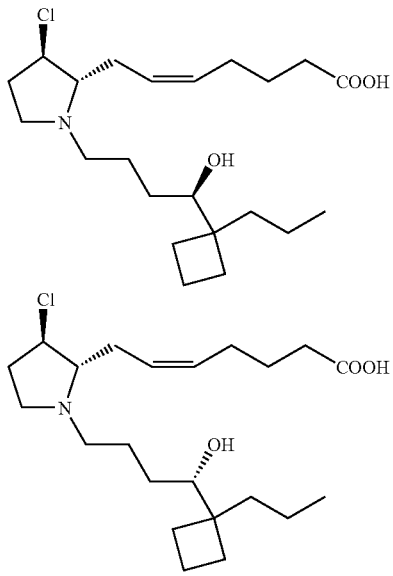

The title compounds were prepared from cyclobutanecarboxylic acid, propyl iodide, and intermediate 1.9 using the procedure of Example 2.

Example 9a: MS (m/z) 40021 (M+1)

Example 9b: MS (m/z) 400.2 (M+1).

Example 10

Preparation of 4-(2-{3-chloro-1-[(4R)-4-hydroxynonyl]pyrrolidin-2-yl}ethyl)benzoic acid (Scheme 3, Steps A-C and G-L)

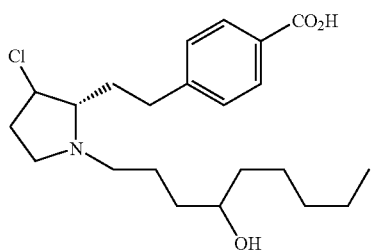

The title compound was prepared as the TFA salt from intermediate 8.3 and intermediate 1.13 using the procedure of Example 1. $^1$H NMR (CD$_3$OD) δ 0.85-0.97 (t, 3H), 1.20-1.65 (m, 10H), 1.68-1.95 (m, 2H), 2.02-2.13 (m, 1H), 2.13-2.26 (m, 1H), 2.35-2.45 (m, 1H), 2.55-2.70 (m, 1H), 2.82-3.04 (m, 2H), 3.20-3.62 (m, 4H), 3.70-3.92 (m, 2H), 4.65-4.75 (m, 1H), 7.40 (d, 2H), 7.97 (d, 2H); MS (m/z) 396 (M+1).

Example 11

Preparation of 4-(2-{1-[4-(1-butylcyclobutyl)-4-hydroxybutyl]-3-chloropyrrolidin-2-yl}ethyl)benzoic acid (Scheme 3, Steps A-C and G-L)

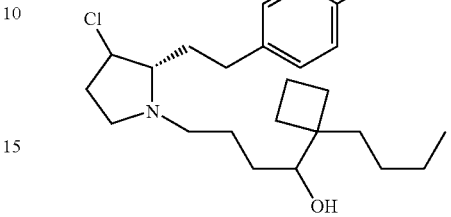

The title compound was prepared as the TFA salt from intermediate 8.3 and 4-(1-butylcyclobutyl)-4-{[tert-butyl(dimethyl)silyl]oxy}butanal (obtained from cyclobutane carboxylic acid and 1-bromobutane as described for intermediate 2.6) using the procedure of Example 1. $^1$H NMR (CD$_3$OD) δ 0.85-0.97 (t, 3H), 1.20-1.45 (m, 6H), 1.45-2.25 (m, 12H), 2.35-2.45 (m, 1H), 2.55-2.65 (m, 1H), 2.82-3.04 (m, 2H), 3.20-3.62 (m, 4H), 3.70-3.88 (m, 2H), 4.65-4.75 (m, 1H), 7.40 (d, 2H), 7.97 (d, 2H); MS (m/z) 436 (M+1).

Example 12

Preparation of 7-[1-(3-Hydroxy-4-phenyl-butyl)-3-oxopyrrolidin-2-yl]-hept-5-enoic acid (Scheme 4, Steps A-H)

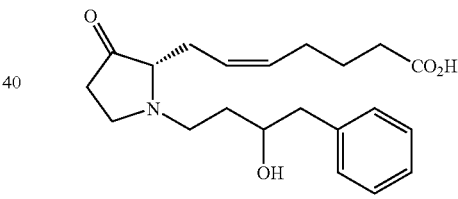

Intermediate 12.1

To a solution of 3-(tert-butyl-dimethyl-silanyloxy)-2-methoxycarbonylmethyl-pyrrolidine-1-carboxylic acid benzyl ester (obtained from 3-aminopropanal according to the procedure of Macdonald et al: *J. Med. Chem.* 1998, 41(21), 3919-3922)) (10.0 g. 0.025 mol) in MeOH (50 mL) was added Pd/C (1.0 g). The mixture was stirred under hydrogen atmosphere (1 atm) for 4 h, then filtered through celite and concentrated under reduced pressure to afford the desired intermediate (6.0 g, 90%) as a colorless oil used in the next step without further purification. $^1$H NMR (CDCl$_3$) δ (mixture of diastereoisomers) 0.05 (s, 6H), 0.87 (s, 9H), 1.65-1.82 (m, 1H), 1.95-2.05 (m, 1H), 2.3-2.7 (m, 2H), 2.95-3.4 (m, 2H), 3.67-3.68 (2s, 3H), 3.90-4.31 (m, 1H); MS (m/z) 274.2 (M+1).

To a solution of the free amine previously obtained (6.0 g, 0.022 mol) in DCM (100 mL) were added di-tert-butyl dicarbonate (3.7 mL, 0.026 mol), Et$_3$N (3.7 mL, 0.026 mol), and DMAP (0.6 g). The resulting solution was stirred at RT for 18 h then was washed with HCl 1.0M (2×100 mL) and brine (100 mL), dried over sodium sulfate and concentrated in vacuo to afford the desired intermediate (8.0 g, 97%) as a pale yellow oil used in the next step without further purification. $R_f$ 0.6 (EtOAc/hexane 1/4); $^1$H NMR (CDCl$_3$) o (mixture of diastereoisomers) 0.04-0.06 (2s, 6H), 0.88-0.90 (2s, 9H), 1.42-1.45 (2s, 9H), 1.70-2.20 (m, 2H), 2.55-2.90 (m, 2H), 3.30-3.55 (m, 2H), 3.60-3.70 (2s, 3H), 3.8-4.0 (m, 1H).

Intermediate 12.2

To a solution of intermediate 12.1 (7.5 g, 0.02 mol) in dry benzene (150 mL) was added dropwise a solution of Red-A1 (6.3 mL, 65+wt % solution in toluene, 0.022 mol). This solution was stirred at reflux for 1 h then cooled to RT and quenched with a saturated solution of Rochelle salt. The mixture was extracted with EtOAc (2×150 mL) and the collected organic phase was washed with brine (200 mL), dried and concentrated in vacuo. The crude mixture of diastereoisomers was purified by silica gel flash column chromatography using EtOAc/hexane as eluent to afford the desired intermediates.

Intermediate 1.2a (cis isomer): $R_f$ 0.30 (EtOAc/hexane 1/4); $^1$H NMR (CDCl$_3$) δ 0.06 (s, 6H), 0.88 (s, 9H), 1.2-1.4 (m, 2H), 1.45 (s, 9H), 1.90-2.10 (m, 2H), 3.20-3.40 (m, 2H), 3.50-3.72 (m, 2H), 4.00-4.10 (m, 1H), 4.25-4.40 (m, 2H); MS (m/z): 346 (M+1).

Intermediate 1.2b (trans isomer): $R_f$ 0.25 (EtOAc/hexane 1/4); $^1$H NMR (CDCl$_3$) δ 0.05 (s, 6H), 0.85 (s, 9H), 1.1-1.2 (m, 1H), 1.45 (s, 9H), 1.70-2.00 (m, 2H), 3.30-3.70 (m, 5H), 3.85-4.02 (m, 2H), 4.53 (dd, J=5.5 and 9.5 Hz, 1H); MS (m/z): 346 (M+1).

Intermediate 12.3

Step A (Swern Oxydation):

A DCM solution of oxalyl chloride (21.0 mL, 2.0 M, 0.043 mol) was diluted with dry DCM (200 mL) and cooled to −70° C. then a solution of DMSO (3.75 mL, 0.053 mol) in DCM (40 mL) was added dropwise. After 15 min. to this solution was added dropwise a solution of intermediate 1.2 (11.4 g, 0.033 mol) in DCM (40 mL). The resulting solution was stirred at −70° C. for 45 min. then Et$_3$N (23.0 mL, 0.165 mol) was added dropwise and the solution warmed to RT. After 15 min. the solution was diluted with DCM (200 mL) and washed with a saturated solution of NH4Cl (2×300 mL), brine (300 mL), dried over sodium sulfate and concentrated in vacuo to afford the aldehyde intermediate (11.2 g, 98%) used in the next step without further purification. $R_f$ 0.37 (EtOAc/hexane 1/4); $^1$H NMR (CDCl$_3$) δ 0.06-0.08 (2s, 6H), 0.86 (s, 9H), 1.44 (s, 9H), 1.70-1.95 (m, 2H), 2.35-2.45 (m, 1H), 2.58-2.81 (m, 1H), 3.35-3.60 (m, 3H), 3.95-4.10 (m, 2H), 9.76 (s, 1H); MS (m/z): 344 (M+1).

Step B (Wittig Reaction):

A suspension of (4-carboxybutyl)triphenylphosphonium bromide (20.0 g, 0.044 mol) in THF (250 mL) was cooled to 0° C., then a THF solution of KO$^t$Bu (90 mL, 1.0 M, 0.09 mol) was added dropwise. After 15 min. was added a solution of the aldehyde intermediate (10 g, 0.03 mol) in THF (100 mL). The resulting mixture was stirred at RT for 18 h then was diluted EtOAc (300 mL) and washed with HCl 1M solution (200 mL) and brine (200 mL). The organic phase was dried over sodium sulfate and concentrated in vacuo to afford the crude acid intermediate used directly in the next step without further purification.

Step C (Esterification Reaction):

To a solution of the crude acid in DCM (180 mL) and MeOH (42 mL) was added dropwise a solution of trimethylsylildiazomethane (50 mL, 2 M solution in hexane, 12 mmol). The resulting solution was stirred at RT for 5 h then was concentrated under reduced pressure. The crude residue was purified by silica gel flash column chromatography using EtOAc/hexane as eluent to afford the desired ester intermediate 1.5 (8.6 g, 66%) as colorless oil. $R_f$ 0.50 (EtOAc/hexane 1/4); $^1$H NMR (CDCl$_3$) δ 0.03 (s, 6H), 0.88 (s, 9H), 1.44 (s, 9H), 1.60-1.80 (m, 3H), 1.90-2.10 (m, 4H), 2.30 (t, J=7.72 Hz, 2H), 2.30-2.45 (m, 1H), 3.30-3.55 (m, 3H), 3.65 (s, 3H), 4.01-4.10 (m, 1H), 5.35-5.50 (m, 2H).

Intermediate 12.4

To a solution of intermediate 12.3 (8.0 g, 0.018 mol) in THF (50 mL) was added dropwise a solution of TBAF (20.0 mL, 1.0 M, 0.02 mol) in THF. The clear solution was stirred at RT for 2 h then was concentrated under reduced pressure. The residue was diluted with EtOAc (200 mL), washed with water (2×100 mL), brine (100 mL), dried over sodium sulfate and concentrated in vacuo. The crude residue was purified by silica gel flash column chromatography using EtOAc/hexane as eluent to afford the alcohol intermediate (5.8 g, 95%) as a colorless oil. $R_f$ 0.30 (EtOAc/hexane 1/1); $^1$H NMR (CDCl$_3$) δ 1.46 (s, 9H), 1.65-1.90 (m, 3H), 2.00-2.18 (m, 3H), 2.31 (t, J=7.3 Hz, 2H), 2.30-2.50 (m, 1H), 3.35-3.75 (m, 3H), 3.66 (s, 3H), 4.05-4.15 (m, 1H), 5.35-5.52 (m, 2H).

Intermediate 12.5

A DCM solution of oxalyl chloride (1.0 mL, 2.0 M, 2.0 mmol) was diluted with dry DCM (15 mL) and cooled to −70° C. then a solution of DMSO (0.17 mL, 2.44 mmol) in DCM (7 mL) was added dropwise. After 15 min. to this solution was added dropwise a solution of intermediate 12.4 (0.5 g, 1.53 mmol) in DCM (7 mL). The resulting solution was stirred at −70° C. for 45 min. then Et$_3$N (1.06 mL, 7.6 mmol) was added dropwise and the solution warmed to RT. After 15 min. the solution was diluted with DCM (50 mL) and washed with a saturated solution of NH4Cl (2×50 mL), brine (50 mL), dried over sodium sulfate and concentrated in vacuo to afford the aldehyde intermediate (0.49 g, 98%) used in the next step without further purification. $R_f$ 0.75 (EtOAc/hexane 1/1); $^1$H NMR (CDCl$_3$) δ 1.48 (s, 9H), 1.50-1.75 (m, 4H), 2.00-2.15 (m, 2H), 2.28 (t, 2H), 2.35-2.70 (m, 4H), 3.45-3.55 (m, 1H), 3.65 (s, 3H), 3.90-4.05 (m, 2H), 5.25-5.55 (m, 2H).

A solution of the ketone intermediate (200 mg, 0.62 mmol), trimethyl orthoformate (0.86 mL, 7.86 mmol), and H$_2$SO$_4$ (0.03 mL) in MeOH (3 mL) was stirred at RT for 24 h. The solution was then concentrated in vacuo, diluted with EtOAc (50 mL) and washed with saturated solution of NaHCO$_3$ (30 mL), and brine (30 mL). The organic solution was dried and concentrated under reduced pressure to afford the desired intermediate (160 mg, 98%) as a pale yellow oil used in the next step without purification. $^1$H NMR (CDCl$_3$) δ 1.60-1.74 (m, 2H), 1.80-2.20 (m, 6H), 2.22-2.38 (m, 3H), 2.85-2.95 (m, 1H), 2.96-3.07 (m, 1H), 3.20 (s, 3H), 3.26 (s, 3H), 3.67 (s, 3H), 5.35-5.55 (m, 2H); MS (m/z) 272 (M+1).

Intermediate 12.6

To a solution of intermediate 12.5 (1.50 g, 5.5 mmol) in i-PrOH (13 mL) was added a solution of D-tartaric acid (0.83 g, 5.5 mmol) in i-PrOH (12 mL). The mixture was stirred at RT for 2 h then at 0° C. for 30 min. The white precipitate was filtered out and washed with small amount of i-PrOH. The residue was diluted with EtOAc and washed with a saturated solution of NaHCO$_3$, brine, dried and concentrated in vacuo to afford the desired chiral amine (0.38 g).

Intermediate 12.7

To a solution of intermediate 12.6 (50 mg, 0.18 mmol) in EtOH (10 mL) was added 1-phenyl-propenone (79 mg, 0.54 mmol). The resulting solution was stirred at reflux for 2 h, and then was concentrated in vacuo. The crude residue was subjected to flash chromatography and was eluted with EtOAc/hexane to afford the desired intermediate (70 mg, 93%) as colorless oil. $R_f$ 0.35 (EtOAc/hexane 1/1); $^1$H NMR (CDCl$_3$) δ 1.60-1.73 (m, 2H), 1.80-2.70 (m, 16H), 3.10 (s, 3H), 3.19 (s, 31), 3.65 (s, 3H), 3.60-3.80 (m, 1H), 5.30-5.50 (m, 2H), 7.10-7.40 (m, 5H); MS (m/z) 418 (M+1).

Intermediate 12.8

To a mixture of intermediate 12.7 (70 mg, 0.17 mmol) in MeOH (4 mL) and water (5 mL) were added CeCl$_3$ (42 mg, 0.17 mmol) followed by NaBH$_4$ (13 mg, 0.34 mmol). After 1 h the reaction was diluted with EtAOc (20 mL) and washed with a saturated solution of NaHCO$_3$ (20 mL), brine (20 mL), dried and concentrated in vacuo to afford a mixture of the 2 diastereoisomers intermediate (60 mg, 85%) used in the next step without further purification. $R_f$ 0.20 and 0.15 (EtOAc/hexane 1/1); MS (m/z) 420 (M+1).

The title compound, 7-[1-(3-Hydroxy-4-phenyl-butyl)-3-oxopyrrolidin-2-yl]-hept-5-enoic acid, was then prepared as follows. A solution of intermediate 12.11 (50 mg) in ACN (3 mL) and HCl 6M (3 mL) was stirred at RT for 4 h. The solution was then concentrated under reduced pressure and purified by RP-HPLC (ACN/H$_2$O/0.1% TFA) to afford the desired compound (30 mg) as a colorless oil $^1$H NMR (CD$_3$OD) δ 1.55-1.75 (m, 2H), 1.80-2.00 (m, 2H), 2.02-2.20 (m, 2H), 2.25-2.40 (m, 2H), 2.60-2.95 (m, 6H), 3.30-3.50 (m, 2H), 3.60-3.85 (m, 2H), 3.90-4.15 (m, 2H), 5.35-5.45 (m, 1H), 5.60-5.70 (m, 1H), 7.15-7.40 (m, 5H); MS (m/z) 360 (M+1).

Example 13

Synthesis of (5Z)-7-{(2S)-1-[3-hydroxy-4-(3-methylphenyl)butyl]-3-oxopyrrolidin-2-yl}hept-5-enoic acid (Scheme 4, Steps A-H)

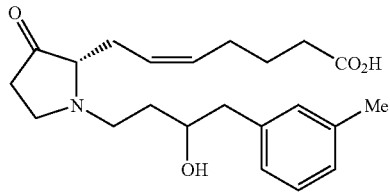

Intermediate 13.1

To a solution of intermediate 12.6 (100 mg, 0.37 mmol) in EtOH (10 mL) was added 1-(3-methylphenyl)prop-2-en-1-one (300 mg, 2.05 mmol). The resulting solution was stirred at reflux for 2 h, and then was concentrated in vacuo. The crude residue was subjected to flash chromatography and was eluted with EtOAc/hexane to afford the desired intermediate (100 mg, 631%) as colorless oil. $R_f$ 0.20 (EtOAc/hexane 1/1); MS (m/z) 432 (M+1).

Intermediate 13.2

To a mixture of intermediate 13.1 (100 mg, 0.23 mmol) in MeOH (5 mL) and water (5 mL) were added CeCl$_3$ (90 mg, 0.37 mmol) followed by NaBH$_4$ (50 mg, 1.34 mmol). After 1 h the reaction was diluted with EtAOc (20 mL) and washed with a saturated solution of NaHCO$_3$ (20 mL), brine (20 mL), dried and concentrated in vacuo to afford a mixture of the 2 diastereoisomers intermediate that was separated by flash clomun chromatography (EtOAc/hexane). First isomer (50 mg, 50%/o) $R_f$ 0.40 (EtOAc/hexane 4/1); MS (m/z) 434 (M+1). Second isomer (45 mg, 45%), $R_f$ 0.35 (EtOAc/hexane 4/1); MS (m/z) 434 (M+1).

The title compound, (5Z)-7-{(2S)-1-β-hydroxy-4-(3-methylphenyl)butyl]-3-oxopyrrolidin-2-yl}hept-5-enoic acid, was then prepared as follows. A solution of intermediate 13.2, second isomer, (45 mg, 0.10 mmol) in ACN (2 mL) and HCl 6M (3 mL) was stirred at RT for 14 h. The solution was then concentrated under reduced pressure and purified by RP-HPLC (ACN/H$_2$O/0.1% TFA) to afford the desired compound (38 mg) as colorless oil. $^1$H NMR (CD$_3$OD) δ 1.50-1.73 (m, 2H), 1.75-1.97 (m, 2H), 2.03-2.18 (m, 2H), 2.3 (s, 3H), 2.55-2.90 (m, 6H), 3.20-3.55 (m, 2H), 3.60-3.82 (m, 2H), 3.87-4.15 (m, 2H), 5.35-5.48 (m, 1H), 5.58-5.72 (m, 1H), 6.95-7.20 (m, 4H); MS (m/z) 374 (M+).

Example 14

Synthesis of 7-[3-Chloro-1-(3-hydroxy-4-m-tolyl-butyl)-pyrrolidin-2-yl]-hept-5-enoic acid (Scheme 4, Steps A-D and I-N)

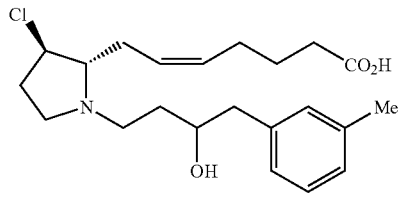

Intermediate 14.1

To a solution of intermediate 12.4 (0.5 g, 1.53 mmol) in pyridine (5 mL) was added tosyl chloride. The solution was stirred at RT for 10 h then at 50° C. for an additional 4 h. The reaction mixture was concentrated in vacuo, diluted with EtOAc (100 mL) and washed with HCl 1.0 M (100 mL), brine (100 mL), dried over sodium sulfate and concentrated in vacuo. The crude residue was purified by silica gel flash column chromatography using EtOAc/hexane as eluant to afford the desired intermediate (0.51 g, 70%/o) as colorless oil. $R_f$ 0.3 (EtOAc/hexane 1/4); $^1$H NMR (CDCl$_3$) δ 1.20-1.30 (m, 1H), 1.41 (s, 9H), 1.60-1.75 (m, 21), 1.90-2.15 (m, 4H), 2.20-2.50 (m, 3H), 2.45 (s, 3H), 3.20-3.45 (m, 2H), 3.64 (s, 3H), 3.85-3.95 (m, 1H), 4.91 (q, J=6.6 Hz, 1H), 5.30-5.45 (m, 21), 7.32 (d, J=8.1 Hz, 2H)), 7.78 (d, J=8.1 Hz, 2H).

Intermediate 14.2

To a solution of intermediate 14.1 (0.9 g, 1.80 mmol) in dry toluene (60 mL) was added tetrabutyl ammonium chloride (5.0 g, 18.0 mmol). The reaction mixture was stirred at 55° C. for 48 h then was diluted with water and extracted with EtOAc (2×100 mL). The collected organic phase was washed with water (2×100 mL), saturate solution of NaHCO$_3$ (100 mL), and brine (100 mL). The organic solution was dried over sodium sulfate and concentrated in vacuo to afford the chloride intermediate (0.6 g, 96%) as a colorless oil. $R_f$ 0.50 (EtOAc/hexane 1/4); $^1$H NMR (CDCl$_3$) δ 1.46 (s, 9H), 1.60-1.75 (m, 2H), 2.02-2.16 (m, 4H), 2.25-2.55 (m, 4H), 3.38-3.70 (m, 2H), 3.66 (s, 3H), 3.87-4.08 (m, 1H), 4.15-4.25 (m, 1H), 5.30-5.55 (m, 2H).

The previous intermediate (0.30 g, 0.87 mmol) was treated with a 4M solution of HCl in dioxane (6 mL). The resulting solution was stirred at 0° C. for 2 h then was concentrated under reduced pressure. The crude residue was diluted with a saturated solution of NaHCO$_3$ (50 mL) and extracted with EtOAc (3×40 mL). The collected organic phase was washed with brine (100 mL), dried over sodium sulfate and concentrated under reduced pressure to afford the amine intermediate (0.24 g, 95%) used in the next step without further purification. MS (m/z): 246 (M+1).

Intermediate 14.3

To a solution of intermediate 14.2 (100 mg, 0.41 mmol) in EtOH (10 mL) was added 1-m-tolyl-propenone (326 mg, 2.04 mmol). The resulting solution was stirred at reflux for 2 h, and then was concentrated in vacuo. The crude residue was subjected to flash chromatography and was eluted with EtOAc/hexane to afford the desired intermediate (150 mg, 95%) as colorless oil. R$_f$ 0.80 (EtOAc/hexane 1/1); $^1$H NMR (CDCl$_3$) δ 1.62-1.73 (m, 2H), 1.80-2.70 (m, 13H), 2.90-3.00 (m, 1H), 3.05-3.15 (m, 1H), 3.19 (s, 3H), 3.65 (s, 3H), 3.72 (s, 2H), 3.87-3.97 (m, 1H), 5.35-5.50 (m, 2H), 7.00-7.25 (411); MS (m/z) 406 (M+1).

Intermediate 14.4 and 14.5

To a mixture of intermediate 14.3 (150 mg, 0.37 mmol) in EtOH (5 mL) and water (5 mL) were added CeCl$_3$ (91 mg, 0.37 mmol) followed by NaBH$_4$ (42 mg, 1.11 mmol). After 1 h the reaction was diluted with EtAOc (20 mL) and washed with a saturated solution of NaHCO$_3$ (20 mL), brine (20 mL), dried and concentrated in vacuo to afford a mixture of the 2 diastereoisomers intermediate that were separated by flash column chromatography on silica gel (EtOAc/hexane). Intermediate 3.4 (50 mg): R$_f$ 0.40 (EtOAc/hexane 1/1); $^1$H NMR (CDCl$_3$) δ 1.60-1.75 (m, 2H), 1.90-2.50 (m, 17H), 2.75-2.85 (m, 2H), 2.95-3.05 (m, 1H), 3.30-3.40 (m, 1H), 33.65 (s, 3H), 3.90-4.04 (m, 2H), 5.35-5.55 (m, 2H), 6.95-7.25 (m, 4H); MS (m/z) 408 (M+1). Intermediate 3.5 (54 mg): R$_f$ 0.35 (EtOAc/hexane 1/1); $^1$H NMR (CDCl$_3$) δ 1.45-1.80 (m, 4H), 1.95-2.50 (m, 13H), 2.55-2.90 (m, 4H), 3.05-3.20 (m, 2H), 3.60 (s, 3H), 3.90-4.10 (m, 2H), 5.40-5.55 (m, 2H), 6.95-7.22 (m, 4H); MS (m/z) 408 (M+1).

The title compound, 7-[3-Chloro-1-(3-hydroxy-4-m-tolyl-butyl)-pyrrolidin-2-yl]-hept-5-enoic acid (first isomer in TLC), then was prepared as follows. To a solution of intermediate 14.4 (50 mg, 0.12 mmol) in water (0.4 mL), MeOH (1.2 mL), and THF (1.2 mL) was added NaOH (32 mg, 0.8 mmol). The resulting solution was stirred at RT for 5 h then concentrated under reduced pressure. The crude mixture was purified by RP-HPLC using ACN/H$_2$O/0.1% TFA to afford the desired compound (25 mg). $^1$H NMR (CD$_3$OD) δ 1.62-1.95 (m, 4H), 2.10-2.20 (m, 2H), 2.25-2.40 (m, 5H), 2.50-2.70 (m, 3H), 2.70-2.90 (m, 2H), 3.25-3.40 (m, 2H), 3.45-3.65 (m, 2H), 3.70-3.88 (m, 2H), 3.91-4.03 (m, 1H), 4.38-4.49 (m, 1H), 5.40-5.50 (m, 1H), 5.65-5.79 (m, 1H), 6.98-7.22 (m, 4H); MS (m/z) 394 (M+1).

Example 15a and 15b (5Z)-7-{(trans-2,3)-3-Chloro-1-[(4S and 4R)-4-hydroxy-4-(1-butylcyclobutyl)butyl]pyrrolidin-2-yl}hept-5-enoic acid (Scheme 2, Steps A-F)

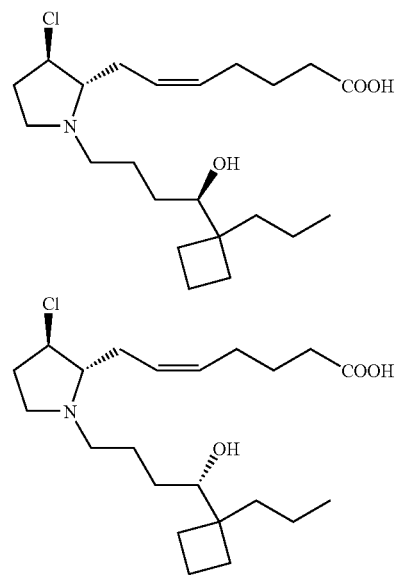

Intermediate 15.1: 1-Butylcyclobutanecarboxylic Acid.

A solution of lithium di-isopropylamide (100 mL, 2.0 M, 200 mmol) in heptane/tetrahydrofuran/benzene was diluted with 100 mL of anhydrous THF. To the LDA solution at 0° C. was added dropwise 10 g (100 mmol) of cyclobutanecarboxylic acid in 15 mL of anhydrous THF over 20 minutes under Argon. The mixture was stirred at room temperature for 3 hours. To the reaction mixture was added 11.4 mL (100 mmol) of butyl iodide at 0° C. The reaction mixture was warmed to RT and stirred overnight. HCl (2N) was used to adjust the pH to 2~3. The mixture was extracted with EtOAc (3×200 mL). The combined organic phase was washed with 100 mL of brine, dried (MgSO$_4$) and concentrated. Thus obtained crude product was used directly for next step.

Intermediate 15.2: (1-Butylcyclobutyl)methanol.

To a solution of lithium aluminum hydride (120 mL, 1.0 M, 150 mmol) in THF was added dropwise at RT a solution of intermediate 15.1 synthesized above in THF (25 mL). The mixture was heated at reflux for 30 minutes, and allowed to cool to rt overnight. Water was added dropwise at 0° C. until no bubbles coming off. The mixture was filtered through a Celite pad, washed with ether (3×150 mL). The filtrate was concentrated. Flash chromatography of the crude product over silica gel, eluting with EtOAc/hexanes (1:10) afforded 8.83 g (62% 2 steps) of the pure product as a colorless oil. R$_f$ 0.5 (EtOAc/hexanes 1:4). $^1$HNMR (CDCl$_3$) δ 3.53 (s, 2H), 1.65~1.90 (m, 4H), 1.40~1.55 (m, 2H), 1.15~1.35 (m, 4H), 0.95 (t, J=7.3 Hz, 3H).

Intermediate 15.3: 1-butylcyclobutanecarbaldehyde

To 31.6 mL of 2.0 M (63.3 mmol) of oxalyl chloride in dichloromethane was added 100 mL of DCM followed by 9.0 mL (126 mmol) of dimethylsulfoxide under Ar at −78° C. The mixture was stirred at −78° C. for 30 min. To this mixture was added 6.00 g (42.2 mmol) of (1-butylcyclobutyl)methanol in 10 mL of DCM. The temperature was allowed to warm to –40° C. over 40 minutes. To this mixture was added 35.3 mL (253 mmol) of Et$_3$N dropwise. After the addition was completed, the temperature was allowed to warm to 0° C. over 1 hr. Water (30 mL) was added to the reaction mixture. The pH of the mixture was adjusted to 6 using 2N HCl. After extraction with DCM (2×100 mL), the combined organic phase was combined, washed with brine, dried (Na$_2$SO$_4$). Concentration afforded 6.0 g of the crude product as colorless oil, which was used directly for next step.

Intermediate 15.4: 1-(1-Butylcyclobutyl)prop-2-yn-1-ol

To 253 mL of 0.5 M (126 mmol) of ethynylmagnesium bromide solution in THF was added 5.92 g (42.2 mmol) of crude 1-butylcyclobutanecarbaldehyde synthesized above in 10 mL of THE at –60° C. The reaction mixture was allowed to warm to 0° C. over 1.5 hr. The mixture was cooled again to –60° C., 50 mL of saturated aqueous NH$_4$Cl was added dropwise to quench the reaction. After warmed to rt, the mixture was extracted with EtOAc (3×100 mL). The combined organic phase was washed with 50 mL of brine, dried (MgSO$_4$), concentrated. The crude product (6.26 g) was obtained as colorless oil, which was used directly in the next step.

Intermediate 15.5: tert-Butyl(dimethyl) {[1-(1-butylcyclobutyl)prop-2-ynyl]oxy}silane To 6.26 g (37.6 mmol) of crude 1-(1-butylcyclobutyl)prop-2-yn-1-ol in DMF (20 mL) were added imidazole (3.1 g, 45.2 mmol) and tert-butyldimethylsilyl chloride (6.8 g, 45.2 mmol). The reaction mixture was stirred at RT overnight, then concentrated to remove DMF, diluted with 100 ml of EtOAc, and added 100 mL of sat. aq. NH$_4$Cl. After separation, the aq. phase was extracted with EtOAc (2×100 mL). The combined organic phase was washed with 50 mL of brine, dried (Na$_2$SO$_4$), concentrated. Flash chromatography over silica gel of the crude product (eluted with hexanes) afforded the title intermediate (6.82 g, 58% 3 steps) as colorless oil.

Intermediate 15.6: 4{[tert-Butyl(dimethyl)silyl]oxy}-4-(1-butylcyclobutyl)but-2-yn-1-ol To a solution of intermediate 15.5 (6.82 g, 24.3 mmol) in THF (150 mL) was added dropwise at –780C a solution of n-BuLi in hexanes (18.2 mL, 1.6 M, 29.2 mmol). The mixture was stirred at the same temperature for 40 min, after which of paraformaldehyde (1.82 g, 60.8 mmol) was added in one portion under. After stirring at –78° C. for 10 min., the bath was removed, and the mixture was allowed to warm to RT overnight. Sat. aq. NH$_4$Cl (100 mL) was added, followed by 200 mL of EtOAc. The organic phase was separated and the aq. phase was extracted with 2×100 m T of EtOAc. The combined organic phase was washed with 100 mL of brine, dried (Na$_2$SO$_4$), and concentrated under vacuum. Chromatography (silica gel, 1:15 EtOAc/hexanes) of the crude product afforded the title intermediate (4.15 g, 55%) as colorless oil. R$_f$ 0.3 (1:15 EtOAc/hexanes). $^1$HNMR (CDCl$_3$) δ 4.29 (s, 2H), 4.24 (s, 1H), 1.95~2.10 (m, 2H), 1.74~1.82 (m, 2H), 1.40~1.70 (m, 4H), 1.20~1.35 (m, 4H), 0.93 (s, 3H), 0.90 (s, 9H), 0.14 (s, 3H), 0.09 (s, 3H).

Intermediate 15.7: 4-{[tert-Butyl(dimethyl)silyl]oxy}-4-(1-butylcyclobutyl)butan-1-ol To a solution of Intermediate 15.6 (2.00 g, 6.44 mmol) in MeOH (100 mL) was added of 10% Pd/C (340 mg, 0.32 mmol). The mixture was subjected to Parr hydrogenation for 2 hr. The reaction mixture was filtered through a celite pad, washed with MeOH, and concentrated in vacuo. The crude product (1.91 g) was used in the next step without further purification.

Intermediate 15.8: 4-{[tert-Butyl(dimethyl)silyl]oxy}-4-(1-butylcyclobutyl)butanalde-hyde A solution of oxalyl chloride in dichloromethane (4.6 mL, 2.0 M, 9.2 mmol) cooled at –78° C. was diluted with DCM (12 mL) then a solution of DMSO (1.30 mL, 18.4 mmol) in DCM (5 mL) was added dropwise. The solution was stirred at –78° C. for 30 min then a solution of intermediate 15.7 (1.91 g, 6.07 mmol) in DCM (2 mL) was added dropwise. The temperature was allowed to warm to –40° C. over 30 minutes. To this mixture was added dropwise Et$_3$N (5.1 mL, 36.4 mmol). After the addition was completed, the temperature was allowed to warm to 0° C. over 1 hr. The pH of the mixture was adjusted to –6 using 2N HCl. After extraction with DCM (3×50 mL), the combined organic phase was combined, washed with brine, dried (Na$_2$SO$_4$). Concentration afforded of the crude product, which was subjected to chromatography (silica gel, 1:15 EtOAc/Hexanes). The desired product oil (0.96 g, 48%, 2 steps) was obtained as colorless oil. $^1$HNMR (CDCl$_3$) δ 9.77 (s, 1), 3.50~3.55 (m, 1H), 2.40~2.50 (m, 1H), 2.08~2.16 (m, 2H), 1.15-1.95 (m, 15H), 0.93 (s, 3H), 0.90 (s, 9H), 0.05 (s, 6H).

Intermediate 15.9: Methyl (5Z)-7-{(trans-2,3)-1-[4-{[tert-butyl(dimethyl)silyl]oxy}-4-(1-butylcyclobutyl)butyl]-3-chloropyrrolidin-2-yl}hept-5-enoate To a mixture of intermediate 1.9 (100 mg, 0.407 mmol) and intermediate 15.8 (128 mg, 0.407 mmol) in anhydrous MeOH (5 mL) was added dropwise a solution of NaCNBH$_3$ in THF (0.82 mL, 1.0 M) in THF. After 4 hrs at RT, the reaction mixture was concentrated, and diluted with 15 mL of EtOAc, washed with 10 mL of sat. aq. solution NaHCO$_3$. The aq. phase was extracted with 2×10 mL of EtOAc. Combined organic phase was washed with 10 mL of brine, dried (Na$_2$SO$_4$), concentrated. Flash chromatography over silica gel (eluted with 1:15 EtOAc/Hexanes) afforded 30 mg (14%) of the mixed disteseromeric products as a colorless oil. R$_f$ 0.37 (1:9 EtOAc/hexanes). MS (m/z) 542.5 (M+1).

Intermediate 15.10 and Intermediate 12.11: Methyl(5Z)-7-{(trans-2,3)-3-chloro-1-[(4S and 4R)-4 hydroxy-4-(1-butyl-cyclobutyl)butyl]pyrrolidin-2-yl}hept-5-enoate (1st Isomer)

To the distereomeric mixtures of intermediate 15.9 (30 mg, 0.06 mmol) was added 2.5 mL of 4.0 M of HCl in dioxane. The reaction mixture was stirred at RT for 2 hr. It was then concentrated, diluted with EtOAc (5 mL), washed with 5 mL of sat. aq. NaHCO$_3$. The aq. phase was extracted with 3×5 mL of EtOAc. The combined organic phase was washed with 5 mL of brine, dried (Na$_2$SO$_4$), concentrated. After chromatography, the 1st diastereoisomer (Intermediate 1.5.10: 4 mg, 16%)$_4$ mg, 16%)) and 4 mg of the second diastereoisomer (Intermediate 15.11: 4 mg, 16%) were isolated both as colorless oil.

Intermediate 15.10: $^1$HNMR (CDCl$_3$) δ 5.40~5.55 (m, 2H), 3.67 (s, 3H), 3.45 (braod, 1H), 3.25 (broad, 1H), 2.35~2.30 (m, 21), 2.25~1.50 (m, 21H), 1.20~1.45 (m, 8H), 0.90~0.95 (m, 3H). MS (m/z) 428.3.

Intermediate 12.11 $^1$HNMR (CDCl$_3$) δ 5.40~5.55 (m, 2H), 3.67 (s, 3H), 3.45 (braod, 1H), 3.25 (broad, 1H), 2.35~2.30 (m, 2H), 2.25~1.50 (m, 21H), 1.20~1.45 (m, 8H), 0.90~0.95 (m, 3H). MS (m/z) 428.3.

Example 15a (5Z)-7-{(trans-2,3)-3-Chloro-1-[4-hydroxy-4-(1-butylcyclobutyl)butyl]pyrrolidin-2-yl}hept-5-enoic acid (1st isomer)

To 4.0 mg (4.3 μmol) of Intermediate 15.10 was added 0.5 mL of 1.0 N NaOH in MeOH, 0.5 mL of THF and 4 drops of water. The mixture was stirred at rt for 60 hr. After concentration, the mixture was extracted with 3×7 mL of EtOAc. The combined organic phase was washed with brine and dried ($Na_2SO_4$). Concentration afforded the product as an organic film (quantitative). $^1$HNMR ($CD_3OD$) δ 5.65~5.75 (m, 1H), 5.45~5.55 (m, 1H), 3.40~3.80 (m, 9H), 2.10~2.70 (m, 10H), 1.45~2.10 (m, 13H), 1.20~1.45 (m, 4H), 0.88~0.98 (m, 3H). MS (m/z) 414.3.

Example 15b (5Z)-7-{(trans-2,3)-3-Chloro-1-[4-hydroxy-4-(1-butylcyclobutyl)-butyl]pyrrolidin-2-yl}hept-5-enoic acid (2 nd isomer)

To 4.0 mg (4.3 μmol) of Intermediate 15.11 was added 0.5 mL of 1.0 N NaOH in MeOH, 0.5 mL of THF and 4 drops of water. The mixture was stirred at rt for 60 hr. After concentration, the mixture was extracted with 3×7 mL of EtOAc. The combined organic phase was washed with brine and dried ($Na_2SO_4$). Concentration afforded the product as an organic film (quantitative). $^1$HNMR ($CD_3OD$) δ 5.65~5.75 (m, 1H), 5.45~5.55 (m, 1H), 3.40~3.80 (m, 9H), 2.10~2.70 (m, 10H), 1.45-2.10 (m, 13H), 1.20~1.45 (m, 4H), 0.89~0.99 (m, 3H). MS (m/z) 414.3.

Example 16a and 16b

Synthesis of (5Z)-7-{(2S,3R)-3-chloro-1-[(3R and 3S)-3-hydroxy-4-(3-methylphenyl)butyl]pyrrolidin-2-yl}hept-5-enoic acid (Scheme 4, Steps A-D and I-N)

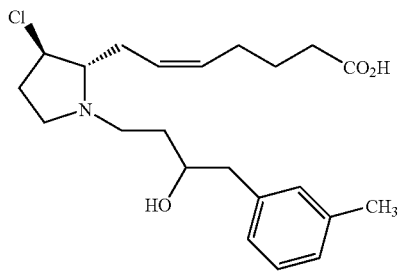

Intermediate 16.1: N-methoxy-N-methyl-2-(3-methylphenyl)acetamide.

To a solution of m-tolyl acetic acid (2.0 g, 0.013 mol) in DMF (20 mL) were added N,O-dimethyl hydroxylamine hydrochloride (1.6 g, 0.016 mol), EDC (3.06 g, 0.016 mol), HOAt (2.17 g, 0.016 mol), and DiPEA (11.6 mL, 0.067 mol). The resulting solution was stirred at RT for 18 h then was diluted with EtOAc (200 mL) and washed with HCl 1M (100 mL), water (100 mL), sat. sol. $NaHCO_3$ (100 mL), and brine (100 mL). The organic phase was dried over sodium sulfate and concentrated in vacuo to afford the title intermediate (2.2 g, 880%) as colorless oil used in the next step without further purification.

Intermediate 16.2: 1-(3-methylphenyl)but-3-en-2-one.

To a solution of intermediate 16.1 (2.2 g, 0.011 mol) in dry THF (100 mL) was added dropwise at 0° C. a solution of vinyl magnesium bromide (12 mL, 1.0 M, 0.012 mol). The resulting solution was stirred at 0° C. for 1 h then was quenched with a saturated solution of $NH_4Cl$ (100 mL). The mixture was extracted with EtOAc (2×100 mL). The collected organic phase was washed with brine, dried, and concentrated under vacuum to afford the title intermediate used in the next step without further purification.

Intermediate 16.3: methyl(5Z)-7-{(2S,3R)-3-chloro-1-(4-(3-methylphenyl)-3-oxobutyl]pyrrolidin-2-yl}hept-5-enoate.

A mixture of intermediate 1.9 (100 mg, 0.407 mmol) and intermediate 16.2 (326 mg, 2.0 mmol) in EtOH (5 mL) was refluxed 2 h then concentrated under reduced pressure. The crude residue was purified by silica gel column chromatography (EtOAc/hexanes) to afford the title compound (150 mg, 95%) as colorless oil. $R_f$ 0.8 (EtOAc/hexanes 1/1);

Intermediate 16.4 and 16.5: methyl(5Z)-7-{(2S,3R)-3-chloro-1-[(3S and 3R)-3-hydroxy-4-(3-methylphenyl)butyl]pyrrolidin-2-yl}hept-5-enoate To a mixture of intermediate 16.3 (150 mg, 0.37 mmol) in EtOH (5 mL) and water (5 mL) were added $CeCl_3.H_2O$ (91 mg, 0.37 mmol) followed by $NaBH_4$ (42 mg, 1.11 mmol). After 1 h the reaction was diluted with EtOAc (20 mL) and washed with a saturated solution of $NaHCO_3$ (20 mL), brine (20 mL), dried and concentrated in vacuo to afford a mixture of the 2 diastereoisomers intermediate that were separated by silica gel column chromatography (EtOAc/hexane). Intermediate 13.4 (50 mg): $R_f$ 0.40 (EtOAc/hexane 1/1); MS (m/z) 408 (M+1). Intermediate 13.5 (40 mg): $R_f$ 0.35 (EtOAc/hexane 1/1); MS (m/z) 408 (M+1).

Example 16a (5Z)-7-{(2S,3R)-3-chloro-1-[(3S)-3-hydroxy-4-(3-methylphenyl)butyl]pyrrolidin-2-yl}hept-5-enoic acid To a solution of intermediate 16.4 (50 mg, 0.13 mmol) in THF (2 mL) and MeOH (2 mL) was added a solution of NaOH (0.98 mg) in $H_2O$ (0.7 mL). The resulting solution was stirred at RT for 4 hours. The solution was then purified by RP-HPLC (ACN/H2O 0.1% TFA) to afford the desired compound (22 mg).

Example 16b (5Z)-7-{(2S,3R)-3-chloro-1-[(3R)-3-hydroxy-4-(3-methylphenyl)butyl]pyrrolidin-2-yl}hept-5-enoic acid To a solution of intermediate 16.5 (50 mg, 0.13 mmol) in THF (2 mL) and MeOH (2 mL) was added a solution of NaOH (0.98 mg) in $H_2O$ (0.7 mL). The resulting solution was stirred at RT for 4 hours. The solution was then purified by R-HPLC (ACN/H2O 0.1% TFA) to afford the desired compound (32 mg).

Example 17

4-{2-[(2S,3R)-3-chloro-1-(4-hydroxynonyl)pyrrolidin-2-yl]ethyl}-benzoic acid (Scheme 3 Steps A-C and G-L)

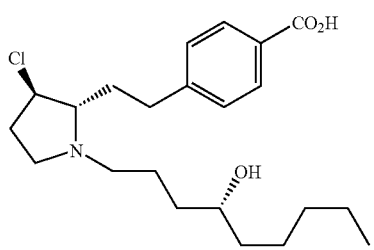

Intermediate 17.1: Methyl 4-{2-[(2S,3R)-1-((4R)-4-{[tert-butyl(dimethyl)silyl]oxy}nonyl)-3-chloropyrrolidin-2-yl]ethyl}benzoate.

To a solution of intermediate 8.3 (0.15 g, 0.56 mmol) and intermediate 1.13 (0.23 g, 0.84 mmol) in MeOH (10 mL) was added a solution of NaCNBH$_3$ in THF (1.0 mL, 1.0 M, 1.20 mmol). The resulting solution was stirred at RT for 18 h then was concentrated in vacuo, diluted with EtOAc (50 mL) and washed with a saturated solution of NaHCO$_3$ (50 mL), and brine (50 mL). The organic solution was dried over sodium sulfate and concentrated in vacuo. The crude residue was purified by silica gel flash column chromatography (EtOAc/hexanes) to afford the desired intermediate (0.08 g, 30%) as a colorless oil. R$_f$ 0.70 (EtOAc/hexane 3/7); MS (m/z): 524 (M+1).

Intermediates 17.2: Methyl 4-(2-{(2S,3R)-3-chloro-1-[(4R)-4-hydroxynonyl]pyrrolidin-2-yl}ethyl)benzoate To a solution of intermediate 17.1 (0.08 g) in dioxane (2 mL) was added a solution of HCl in dioxane (2 mL, 4.0 M). The solution was stirred at RT for 2 h then was concentrated under reduced pressure. The crude residue was diluted with a saturated solution of NaHCO$_3$ (20 mL) and extracted with EtOAc (3×30 mL). The collected organic phase was washed with brine, dried, and concentrated under reduced pressure to afford the title intermediate that was used in the next step without further purification. MS (m/z): 450.3 (M+1).

Example 17

4-{2-[(2S,3R)-3-chloro-1-(4-hydroxynonyl)pyrrolidin-2-yl]ethyl}benzoic acid

To a solution of intermediate 17.2 in MeOH (2 mL) and THF (2 mL) was added a solution of NaOH (0.09 g) in water (0.7 mL). The resulting solution was stirred at RT for 4 h, and then was purified by RP-HPLC (ACN/H$_2$O 0.1% TFA) to afford the title compound (38 mg). MS (m/z) 374 (M+1).

Example 18

Synthesis of (5Z)-7-{1-β-hydroxy-3-(1-phenylcyclopropyl)propyl]-3-oxopyrrolidin-2-yl}hept-5-enoic acid (Scheme 1, Steps A-H)

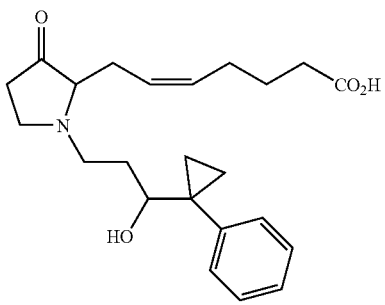

Intermediate 16.1: N-methoxy-N-methyl-1-phenylcyclopropanecarboxamide.

The title compound was prepared according to the procedure described for intermediate 16.1 from 1-phenyl-1cyclopropane carboxylic acid. R$_f$ 0.30 (EtOAc/hexanes 3/7).

Intermediate 18.2: 1-(1-phenylcyclopropyl)prop-2-en-1-one.

The title compound was prepared according to the procedure described for intermediate 16.2 using intermediate 16.1. R$_f$ 0.90 (EtOAc/hexanes 3/7).

Intermediate 18.3: methyl(5Z)-7-{(2S)-3,3-dimethoxy-1-[3-oxo-3-(1-phenylcyclo-propyl)propyl]pyrrolidin-2-yl}hept-5-enoate.

The title compound was prepared according to the procedure described for intermediate 13.1 from methyl(5Z)-7-[(2S)-3,3-dimethoxypyrrolidin-2-yl]hept-5-enoate (intermediate 5.3) and intermediate 18.2. R$_f$ 0.30 (EtOAc/hexanes 1/1); MS (m/z) 444 (M+1).

Intermediate 18.4: methyl(5Z)-7-{1-β-hydroxy-3-(1-phenylcyclopropyl)propyl]-3,3-dimethoxypyrrolidin-2-yl}hept-5 enoate.

The title compound was prepared according to the procedure described for intermediate 13.2 from intermediate 18.3. (mixture of diastereoisomers) R$_f$ 0.50 & 0.45 (EtOAc/hexanes 1/1); MS (m/z) 446 (M+1).

Example 18

(5Z)-7-{1-β-hydroxy-3-(1-phenylcyclopropyl)propyl]-3-oxopyrrolidin-2-yl}hept-5-enoic acid.

The title compound was prepared as TFA salt according to the procedure described in Example 13 from Intermediate 18.4. MS (m/z) 386 (M+1).

Example 19

Synthesis of 7-(1-{4-[1-(cyclopropylmethyl)cyclopropyl]-4-hydroxybutyl}-3-oxopyrrolidin-2-yl)heptanoic acid (Scheme 1, Steps A-F and I, L, N, O)

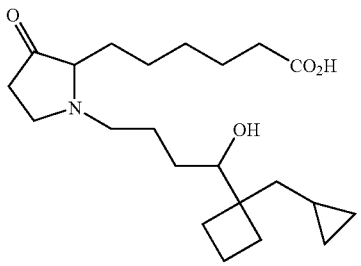

Intermediate 19.1: 1-(cyclopropylmethyl)cyclobutanecarboxylic acid.

The title compound was prepared according to the procedure described for Intermediate 15.1 from cyclobutanecarboxylic acid and (bromomethyl)cyclopropane.

Intermediate 19.2: [1-(cyclopropylmethyl)cyclobutyl]methanol.

The title compound was prepared according to the procedure described for Intermediate 15.2 from intermediate 19.1.

Intermediate 19.3: 1-(cyclopropylmethyl)cyclobutanecarbaldehyde.

The title compound was prepared according to the procedure described for Intermediate 15.3 from intermediate 19.2.

Intermediate 19.4: 1-[1-(cyclopropylmethyl)cyclobutyl]prop-2-yn-1-ol.

The title compound was prepared according to the procedure described for Intermediate 15.4 from intermediate 19.3.

Intermediate 19.5: tert-butyl({1-[1-(cyclopropylmethyl)cyclobutyl]prop-2-ynyl}oxy) dimethylsilane.

The title compound was prepared according to the procedure described for Intermediate 15.5 from intermediate 19.4. $R_f$ 0.8 (EtOAc/hexanes 1/9).

Intermediate 19.6: 4-{[tert-butyl(dimethyl)silyl]oxy}-4-[1-(cyclopropylmethyl) cyclobutyl]but-2-yn-1-ol.

The title compound was prepared according to the procedure described for Intermediate 15.6 from intermediate 19.5. $R_f$ 0.7 (EtOAc/hexanes 1/4).

Intermediate 19.7: 4-{[tert-butyl(dimethyl)silyl]oxy}-4-[1-(cyclopropylmethyl)cyclobutyl]butan-1-ol.

The title compound was prepared according to the procedure described for Intermediate 15.7 from intermediate 19.6.

Intermediate 19.8: {4-bromo-1-[1-(cyclopropylmethyl)cyclobutyl]butoxy}(tert-butyl)dimethylsilane.

The title compound was prepared according to the procedure described for Intermediate 15.8 from intermediate 19.7. $R_f$ 0.5 (EtOAc/hexanes 1/9).

Intermediate 19.9: methyl(5Z)-7-(1-{4-{[tert-butyl(dimethyl)silyl]oxy}-4-[1-(cyclopropylmethyl)clclopropyl]butyl}-3,3-dimethoxypyrrolidin-2-yl)hept-5-enoate.

The title compound was prepared according to the procedure described for Intermediate 15.9 from intermediate 19.7 and methyl(5Z)-7-[(2S)-3,3-dimethoxypyrrolidin-2-yl]hept-5-enoate (intermediate 5.3). $R_f$ 0.7 (EtOAc/hexanes 3/7).

Intermediate 19.10: methyl(5Z)-7-(1-{4-[1-(cyclopropylmethyl)cyclopropyl]4-hydroxybutyl}-3-oxopyrrolidin-2-yl)hept-5-enoate To a solution of intermediate 19.9 (0.62 g) in THF (5 mL) and H$_2$O (1 mL) was added a solution of HCl in dioxane (6 mL, 4.0 M). The resulting solution was stirred at RT for 1 h, then was dilute with EtOAc (50 mL) and washed with a saturated solution of NaHCO$_3$ (50 mL) and brine (50 mL). The organic phase was dried over sodium sulfate and concentrated in vacuo to afford the title intermediate (0.15 g, 34%) used in the next step without further purification. $R_f$ 0.4 (EtOAc/hexanes 3/2); MS (m/z) 406 (M+1).

Example 19

(5Z)-7-(1-{4-[1-(cyclopropylmethyl)cyclopropyl]-4-hydroxybutyl}-3-oxopyrrolidin-2-yl)hept-5-enoic acid To a solution of intermediate 19.10 (20 mg) in THF (0.4 mL) and MeOH (0.4 mL) was added a solution of NaOH (20 mg) in H$_2$O (0.13 mL). The resulting solution was stirred at RT for 18 h then concentrated in vacuo to afford the title compound as sodium salt. MS (m/z) 392 (M+1).

Example 20

Synthesis of (5Z)-7-[(2S,3R)-3-chloro-1-(4-hydroxynonyl)pyrrolidin-2-yl]hept-5-enoic acid (Scheme 2, Steps A-B and D-F)

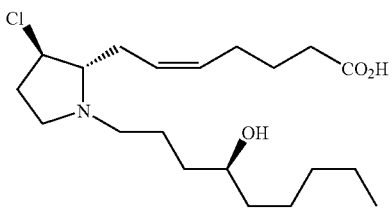

The title compound was prepared according to the procedure described for Example 1 from (S)-1-octyn-3-ol and rac. Methyl (5Z)-7-[(2R,3R)-3-chloropyrrolidin-2-yl]hept-5-enoate (intermediate 1.9). MS (m/z) 375 (M+1).

Example 21

Synthesis of (5Z)-7-{(2S,3R)-3-chloro-1-[4-(1-ethylcyclobutyl)-4-hydroxybutyl]pyrrolidin-2-yl}hept-5-enoic acid (Scheme 2, Steps A-B and D-F)

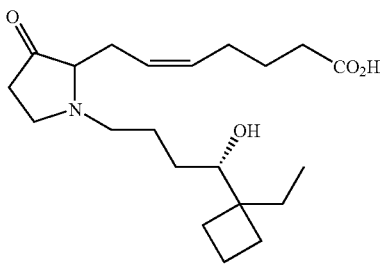

Intermediate 21.1: 1-ethylcyclobutanecarboxylic Acid

The title compound was prepared according to the procedure described for intermediate 2.1 from cyclobutanecarboxylic acid and ethylbromide.

Intermediate 21.2: (1-ethylcyclobutyl)methanol.

The title compound was prepared according to the procedure described for intermediate 2.2 from 1-ethylcyclobutanecarboxylic acid (intermediate 21.1). $R_f$ 0.40 (EtOAc/hexanes 1/4).

Intermediate 21.3: tert-butyl {[1-(1-ethylcyclobutyl)prop-2-ynyl]oxy}dimethylsilane.

The title compound was prepared according to the procedure described for intermediate 2.3 from (1-ethylcyclobutyl) methanol. (intermediate 21.2).

Intermediate 21.4: 4-{[tert-butyl(dimethyl)silyl]oxy}-4-(1-ethylcyclobutyl)but-2-yn-1-ol.

The title compound was prepared according to the procedure described for intermediate 2.4 from 1-ethylcyclobutanecarbaldehyde (intermediate 21.3). $R_f$ 0.50 (EtOAc/hexanes 1/5).

Intermediate 21.5: 4-{[tert-butyl(dimethyl)silyl]oxy}-4-(1-ethylcyclobutyl)butan-1-ol.

The title compound was prepared according to the procedure described for intermediate 2.5 from 1-(1-ethylcyclobutyl) prop-2-yn-1-ol (intermediate 21.4). $R_f$ 0.8 (EtOAc/hexanes 1/9).

Intermediate 21.6: 4-{[tert-butyl(dimethyl)silyl]oxy}-4-(1-ethylcyclobutyl)butanal The title compound was prepared according to the procedure described for intermediate 2.6 from tert-butyl {[1-(1-ethylcyclobutyl)prop-2-ynyl]oxy}dimethylsilane. (intermediate 21.5). $R_f$ 0.6 (EtOAc/hexanes 1/4).

Intermediate 21.7: methyl(5Z)-7-{(2S,3R)-1-[4-{[tert-butyl (dimethyl)silyl]oxy}-4(1-ethylcyclobutyl)butyl]-3-chloropyrrolidin-2-yl}hept-5-enoate.

The title compound was prepared according to the procedure described for intermediate 2.7 from intermediate 21.6. $R_f$ 0.4 (EtOAc/hexanes 1/5).

Intermediate 21.8: methyl(5Z)-7-{(2S,3R)-3-chloro-1-[4-(1-ethylcyclobutyl)-4-hydroxybutyl]pyrrolidin-2-yl}hept-5-enoate.

The title compound was prepared according to the procedure described for intermediate 2.8 from intermediate 21.7. $R_f$ 0.8 (EtOAc/hexanes 1/5).

Example 21

(5Z)-7-{(2S,3R)-3-chloro-1-[4-(1-ethylcyclobutyl)-4-hydroxybutyl]pyrrolidin-2-yl}hept-5-enoic acid The title compound was prepared according to the procedure described for example 2 from intermediate 21.8. MS (m/z) 387 (M+1).

EXAMPLES 22-25

Biological Assays

Example 22

Prostaglandin EP2 Binding Assay

Compounds of the invention were tested in an EP2 receptor binding assay of the following protocol. As referred to herein, the term a "standard EP2 receptor binding assay" designates the following protocol which allows the determination of the affinity of the test compounds for the EP2 receptor.

A mixture containing 20 ug of EP2 receptor membranes, 0.5 mg of wheat germ agglutinin coated PVT-SPA beads, plus or minus a pyrrolidine compound of the invention (25 ul per well) or 10 uM of cold PGE2 at 1% DMSO and 20 nM $^3$H-PGE2 in assay buffer containing 25 mM MES, 10 mM $MgCl_2$, 1 mM EDTA, pH 6.0 are incubated in Corning 3600 plates on a plate shaker for 2 hrs at room temperature. $^3$H-PGE2 binding is evaluated by counting the plates on the top count using the $^3$H SPA dpm2 program. % Binding and Ki value for inhibitors are calculated based on the one site competition parameter using the Graphpad prism program. Ki values are set forth in the Table I which follows Example 25 below.

Example 23

ER2 cAMP Assay

Compounds of the invention were tested in a total cAMP assay as follows. HEK293-EBNA cells transfected with pCEP4-hEP2 receptors were seeded in 96 well opaque plate (Costar #3917) at $4 \times 10^4$ cells per well in 100 µl of culture medium (D-MEM/F12 supplemented with 10% FBS, 2 nM L-glutamine, and 250 µg/ml of hygromycin; all from GibcoBRL) and incubated at 37° C. After overnight incubation, the medium was removed from each well and replaced with 45 µl of assay medium consisted of phenol red free D-MEM/ F-12, 0.1% BSA (GibcoBRL) and 0.1 mM3-isobutyl-1-methyl-xanthine (Sigma). After 15 minutes of incubation at 37° C., 16-16-dimethyl PGE-2 or compounds at desired concentrations in 20 µl of assay medium were added to cells and further incubated at 37° C. for 1 hour. Total cAMP (intra- and extra-cellular) was measured by using a cAMP-screen ELISA System (Tropix, #CS1000). Results (EC50 (µM) are shown in the Table I which follows Example 25 below.

Example 24

EP4 Binding Assay

Compounds of the invention were tested in an EP4 receptor binding assay of the following protocol which allows the determination of the affinity of the test compounds for the EP4 receptor.

A mixture containing 20 µg of EP4 receptor membranes, 0.5 mg of wheat germ agglutinin coated PVT-SPA beads, plus or minus a compound of the invention (25 µl per well) or 10 µM of cold PGE2 at 1% DMSO and 20 nM $^3$H-PGE2 in assay buffer containing 25 mM MES, 10 mM $MgCl_2$, 1 mM EDTA, pH 6.0 are incubated in Corning 3600 plates on a plate shaker for 2 hrs at room temperature. $^3$H-PGE2 binding is evaluated by counting the plates on the top count using the ³H SPA dpm2 program. % Binding and Ki value for inhibitors are calculated based on the one site competition parameter using the Graphpad prism program. EP4 Ki values are set forth in the Table 1 which follows Example 25 below.

Example 25

EP4 cAMP Assay

Compounds of the invention can be tested in a total cAMP assay as follows. HEK293-EBNA cells transfected with pCEP4-hEP4 receptors were seeded in 96 well opaque plate (Costar #3917) at 4×10⁴ cells per well in 100 µl of culture medium (D-MEM/F12 supplemented with 10% FBS, 2 nM L-glutamine, and 250 µg/ml of hygromycin; all from GibcoBRL) and incubated at 37° C. After overnight incubation, the medium was removed from each well and replaced with 45 µl of assay medium consisted of phenol red free D-MEM/F-12, 0.1% BSA (GibcoBRL) and 0.1 mM3isobutyl-1-methyl-xanthine (Sigma). After 15 minutes of incubation at 37° C., 16-16-dimethyl PGE-2 or compounds of the invention at desired concentrations in 20 µl of assay medium are added to cells and further incubated at 37° C. for 1 hour. Total cAMP (intra- and extra-cellular) can be measured by using a cAMP-screen ELISA System Tropix, #CS1000).

TABLE I

| Compound of Example No. | h-EP2 Ki (µM) | h-EP2 EC₅₀ (µM) | h-EP4 Ki (µM) |
|---|---|---|---|
| 1 | 5.6 | 0.048 | ND |
| 11 | 3.5 | 0.25 | ND |
| 13 | 10 | 0.37 | 0.005 |
| 15 | 11.0 | 8.5 (n = 2) | 0.156 |

The invention has been described in detail with reference to preferred embodiments thereof. However, it will be appreciated that those skilled in the art, upon consideration of this disclosure, may make modifications and improvements within the spirit and scope of the invention.

What is claimed is:

1. A compound of the following Formula III:

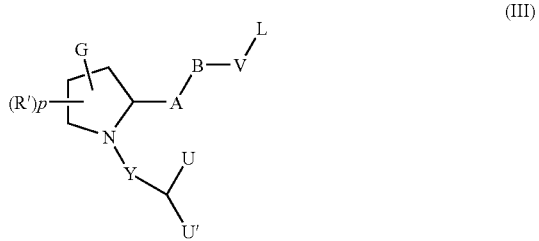

(III)

wherein each R' is independently hydrogen; optionally substituted alkyl; optionally substituted alkenyl; optionally substituted alkynyl; optionally substituted heteroalkyl; optionally substituted heteroalkenyl; optionally substituted heteroalkynyl; optionally substituted carbocyclic aryl; optionally substituted aralkyl; optionally substituted heteroalicyclic, optionally substituted heteroaryl; optionally substituted heteroarylalkyl; or optionally substituted heteroalicyclicalkyl;

G is halogen; optionally substituted alkyl, or optionally substituted alkylcarboxylate ester;

p is an integer of from zero to 4;

Y is $(CR^2R^3)_q$ which may include 0 or 1 C=C double bonds, q is from 1 to 6 and $R^2$ and $R^3$ are each independently selected at each occurrence from the group consisting of hydrogen, optionally substituted alkyl; optionally substituted alkenyl; optionally substituted alkynyl; hydroxy, halogen; and optionally substituted alkoxy; and U and U' are each independently selected from hydrogen, hydroxy or optionally substituted alkyl;

A is $(CR^2R^3)_{q'}$ where q' is an integer from 1 to 6;

B is $(CR^2R^3)_n$, or absent; or

A and B taken in combination form an optionally substituted 1,2-vinylene group or an ethynyl group;

V is $(CR^2R^3)_m$, optionally substituted divalent aryl, or optionally substituted divalent heteroaryl;

L is C(O)Z;

Z is hydroxy, optionally substituted alkyl, optionally substituted alkenyl, optionally substituted alkynyl, optionally substituted heteroalkyl, optionally substituted heteroalkenyl, optionally substituted heteroalkynyl, amino, $NR^4R^5$, optionally substituted cycloalkyl, optionally substituted heterocycloalkyl, optionally substituted carbocyclic aryl, optionally substituted heteroaryl, optionally substituted arylalkyl, or optionally substituted heteroarylalkyl;

n is an integer selected from 0-3;

m is an integer selected from 1-6;

$R^4$ and $R^5$ are independently selected at each occurrence from the group consisting of hydrogen optionally substituted alkyl, optionally substituted cycloalkyl, optionally substituted heterocycloalkyl, optionally substituted alkenyl, optionally substituted alkynyl, optionally substituted heteroalkyl, optionally substituted heteroalkenyl, optionally substituted heteroalkynyl, optionally substituted carbocyclic aryl, optionally substituted heteroaryl, optionally substituted arylalkyl, and optionally substituted heteroarylalkyl, or $R^4$ and $R^5$ taken in combination is an optionally substituted heterocycloalkyl; and pharmaceutically acceptable salts thereof.

2. A compound of the following Formula IV:

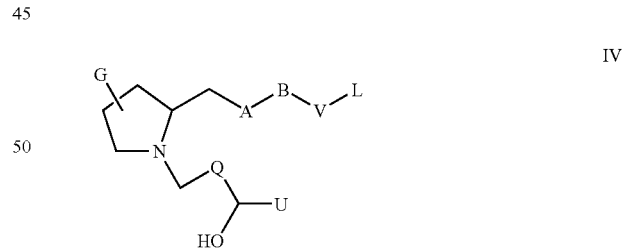

IV wherein A is $CR^2R^3$;

B is $(CR^2R^3)_n$, or absent; or

A and B taken in combination form an optionally substituted 1,2-vinylene group or an ethynyl group;

V is $(CR^2R^3)_m$, optionally substituted divalent aryl, or optionally substituted divalent heteroaryl;

L is C(O)Z;

G is halogen optionally substituted alkyl, or optionally substituted alkylcarboxylate ester;

Q is $(CR^2R^3)_q$ which may include 0 or 1 carbon-carbon double or triple bonds;

U is an optionally substituted alkyl group;

Z is hydroxy, optionally substituted alkyl, optionally substituted alkenyl, optionally substituted alkynyl, optionally substituted heteroalkyl, optionally substituted heteroalkenyl, optionally substituted heteroalkynyl, amino, $NR^4R^5$, optionally substituted cycloalkyl, optionally substituted heterocycloalkyl, optionally substituted carbocyclic aryl, optionally substituted heteroaryl, optionally substituted arylalkyl, or optionally substituted heteroarylalkyl;

n is an integer selected from 0-3;

m is an integer selected from 1-6;

q is an integer selected from 0-5;

$R^2$ and $R^3$ are independently selected at each occurrence from the group consisting of hydrogen, hydroxy, halogen, optionally substituted alkyl, optionally substituted alkenyl, optionally substituted alkynyl, optionally substituted heteroalkyl, optionally substituted heteroalkenyl, and optionally substituted heteroalkynyl; and $R^4$ and $R^5$ are independently are independently selected at each occurrence from the group consisting of hydrogen optionally substituted alkyl, optionally substituted cycloalkyl, optionally substituted heterocycloalkyl, optionally substituted alkenyl, optionally substituted alkynyl, optionally substituted heteroaryl, optionally substituted heteroalkenyl, optionally substituted heteroalkynyl, optionally substituted carbocyclic aryl, optionally substituted heteroaryl, optionally substituted arylalkyl, and optionally substituted heteroarylalkyl, or $R^4$ and $R^5$ taken in combination is an optionally substituted heterocycloalkyl; and pharmaceutically acceptable salts thereof.

3. A compound of the following Formula V:

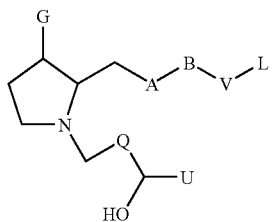

V wherein

A is $CH_2$;

B is $CR^2R^3$ or absent wherein $R^2$ and $R^3$ are independently selected from H and $C_1$-$C_6$ alky; or A and B taken in combination form a 1,2-vinylene group;

G is halogen;

L is C(O)Z;

Q is $(CR^2R^3)_q$ which may include 0 or 1 C=C double bond;

U is —$CR^6R^7$—W, wherein $R^6$ and $R^7$ are independently selected from H and $C_1$-$C_6$ alkyl; or $R^6$ and $R^7$ can form a $C_3$-$C_6$ cycloalkyl with the carbon they are attached to;

V is selected from $(CR^2R^3)_m$, aryl and heteroaryl;

W is selected from hydrogen, $C_1$-$C_6$ alkyl, $C_3$-$C_6$ cycloalkyl $C_1$-$C_6$ alkyl, aryl and heteroaryl;

Z is hydroxy;

m is an integer selected from 1, 2, 3, 4, 5 and 6;

q is an integer selected from 0, 1, 2, 3, 4 and 5.

4. A compound according to claim 3 wherein G is chloro.

5. A compound of claim 3 wherein q is 1 or 2.

6. A compound of claim 3 wherein m is 3.

7. A compound of claim 3 wherein Q includes 0 double bond.

8. A compound according to claim 3 wherein the compound is of the following Formula VI:

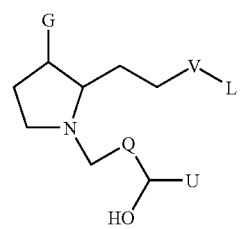

VI wherein

G is halogen;

L is C(O)Z;

Q is $(CR^2R^3)_q$ wherein $R^2$ and $R^3$ are independently selected from H and $C_1$-$C_6$ alkyl;

U is —$CR^6R^7$—W, wherein $R^6$ and $R^7$ are independently selected from H and $C_1$-$C_6$ alkyl; or $R^6$ and $R^7$ can form a $C_3$-$C_6$ cycloalkyl with the carbon they are attached to;

V is selected from aryl and heteroaryl;

W is selected from hydrogen, $C_1$-$C_6$ alkyl and $C_3$-$C_6$ cycloalkyl $C_1$-$C_6$ alkyl;

Z is hydroxy;

q is an integer selected from 1 and 2.

9. A compound according to claim 8 wherein G is chloro.

10. A compound of claim 8 wherein V is aryl.

11. A compound of claim 8 wherein V is phenyl.

12. A compound of claim 3 wherein the compound is of the following Formula VIII:

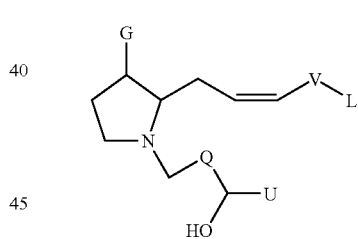

VIII wherein

G is halogen;

L is C(O)Z;

Q is $(CR^2R^3)_q$ which may include 0 or 1 C=C double bond wherein $R^2$ and $R^3$ are independently selected from H and $C_1$-$C_6$ alkyl;

U is —$CR^6R^7$—W, wherein $R^6$ and $R^7$ are independently selected from H and $C_1$-$C_6$ alkyl; or $R^6$ and $R^7$ can form a $C_3$-$C_6$ cycloalkyl with the carbon they are attached to;

V is $(CR^2R^3)_m$;

W is selected from hydrogen, $C_1$-$C_6$ alkyl and $C_3$-$C_6$ cycloalkyl $C_1$-$C_6$ alkyl;

Z is hydroxy;

m is an integer selected from 1, 2 and 3;

q is an integer selected from 1 and 2.

13. A compound according to claim 12 wherein G is chloro.

14. A compound of claim 12 wherein Q includes 0 double bond.

15. A compound of claim 12 wherein q is 2.
16. A compound of claim 12 wherein m is 3.
17. A compound of claim 12 wherein the compound is of the following Formula IX:

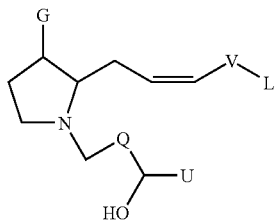

wherein
G is halogen;
L is C(O)Z;
Q is $(CR^2R^3)_q$ wherein $R^2$ and $R^3$ are independently selected from H and $C_1$-$C_6$ alkyl;
U is —$CR^6R^7$—W, wherein $R^6$ and $R^7$ are independently selected from H and $C_1$-$C_6$ alkyl; or $R^6$ and $R^7$ can form a $C_3$-$C_6$ cycloalkyl with the carbon they are attached to;
V is $(CR^2R^3)_m$;
W is selected from aryl and heteroaryl;
Z is hydroxy;
q is an integer selected from 1 and 2;
m is an integer selected from 1, 2 and 3.
18. A compound according to claim 17 wherein G is chloro.
19. A compound of claim 17 wherein q is 1.
20. A compound of claim 17 wherein m is 3.
21. A compound of claim 17 wherein W is aryl.
22. A compound of claim 17 wherein W is phenyl.
23. A compound of following Formula X:

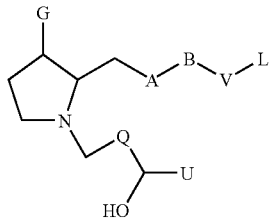

wherein
A is $CH_2$;
B is $CR^2R^3$ or absent wherein $R^2$ and $R^3$ are independently selected from H and $C_1$-$C_6$ alkyl; or A and B taken in combination form a 1,2-vinylene group;
G is halogen, optionally substituted alkyl or optionally substituted alkylcarboxoylate ester;
L is C(O)Z;
Q is $(CR^2R^3)_q$ which may include 0 or 1 C=C double bond;
U is —$CR^6R^7$—W, wherein $R^6$ and $R^7$ are independently selected from H and $C_1$-$C_6$ alkyl; or $R^6$ and $R^7$ can form a $C_3$-$C_6$ cycloalkyl with the carbon they are attached to;
V is selected from aryl and heteroaryl; or V is $(CR^2R^3)_m$ when A and B taken in combination form a 1,2-vinylene group or an ethynyl group;
W is selected from hydrogen, $C_1$-$C_6$ alkyl, $C_3$-$C_6$ cycloalkyl $C_1$-$C_6$ alkyl, aryl and heteroaryl;
Z is hydroxy;
q is an integer selected from 0, 1, 2 3, 4 and 5;
m is an integer selected from 1, 2, 3, 4, 5 and 6.
24. A compound according to claims 23 wherein q is selected from 1 and 2.
25. A compound of claim 23 wherein m is 3.
26. A compound according to claim 23 wherein the compound is of following Formula X':

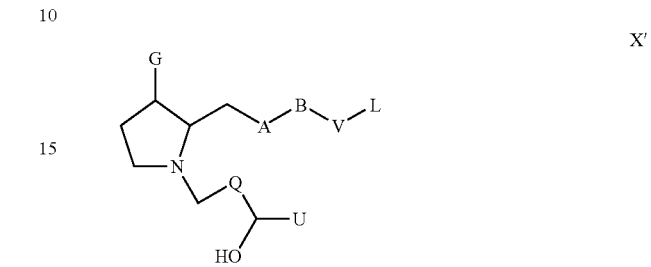

wherein
A is $CH_2$;
B is $CR^2R^3$ or absent wherein $R^2$ and $R^3$ are independently selected from H and $C_1$-$C_6$ alkyl;
G is halogen, optionally substituted alkyl or optionally substituted alkylcarboxoylate ester;
L is C(O)Z;
Q is $(CR^2R^3)_q$ which may include 0 or 1 C=C double bond;
U is —$CR^6R^7$—W, wherein $R^6$ and $R^7$ form a $C_3$-$C_6$ cycloalkyl with the carbon they are attached to;
V is selected from $(CR^2R^3)_m$ aryl and heteroaryl;
W is selected from hydrogen, $C_3$-$C_6$ cycloalkyl and $C_1$-$C_6$ alkyl $C_3$-$C_6$ cycloalkyl;
Z is hydroxy;
q is an integer selected from 0, 1, 2, 3 and 4;
m is an integer selected from 1, 2, 3, 4, 5 and 6.
27. A compound according to claim 26 wherein Q includes 0 double bond.
28. A compound of claim 26 wherein B is $CH_2$.
29. A compound of claim 26 wherein q is 1 or 2.
30. A compound of claim 26 wherein m is 3.
31. A compound of claim 26 wherein V is $(CR^2R^3)_m$.
32. A compound according to claim 23 wherein the compound is of following Formula XI:

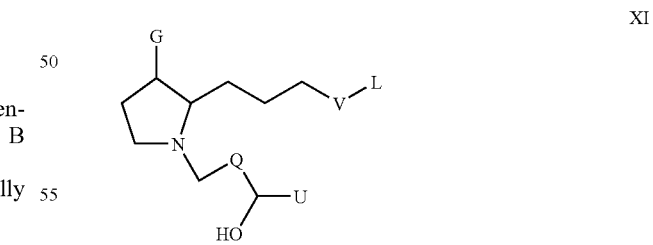

wherein
G is halogen, optionally substituted alkyl or optionally substituted alkylcarboxoylate ester;
L is C(O)Z;
Q is $(CR^2R^3)_q$ wherein $R^2$ and $R^3$ are independently selected from H and $C_1$-$C_6$ akyl;
U is —$CR^6R^7$—W, wherein $R^6$ and $R^7$ are independently selected from H and $C_1$-$C_6$ alkyl; or $R^6$ and $R^7$ can form a $C_3$-$C_6$ cycloalkyl with the carbon they are attached to;

V is selected from aryl and heteroaryl;
W is selected from hydrogen, $C_1$-$C_6$ alkyl and $C_3$-$C_6$ cycloalkyl $C_1$-$C_6$ alkyl;
Z is hydroxy;
m is an integer selected from 1, 2 and 3;
q is selected from 1 and 2.

33. A compound according to claim 32 wherein m is 3.
34. A compound of claim 32 wherein V is phenyl.
35. A compound of following Formula XII:

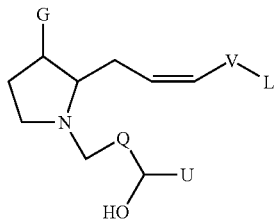

XII wherein
G is halogen, optionally substituted alkyl or optionally substituted alkylcarboxoylate ester;
L is C(O)Z;
Q is $(CR^2R^3)_q$ wherein $R^2$ and $R^3$ are independently selected from H and $C_1$-$C_6$ alkyl,
U is —$CR^6R^7$—W, wherein $R^6$ and $R^7$ are independently selected from H and $C_1$-$C_6$ alkyl; or
$R^6$ and $R^7$ can form a $C_3$-$C_6$ cycloalkyl with the carbon they are attached to;
V is $(CR^2R^3)_m$;
W is selected from aryl and heteroaryl;
Z is hydroxy,
q is an integer selected from 1 and 2;
m is an integer selected from 1, 2 and 3.

36. A compound according to claim 35 wherein q is 1.
37. A compound of claim 35 wherein m is 3.
38. A compound of claim 35 wherein W is phenyl.
39. A compound of claim 2 wherein the compound is of the following Formula XIII:

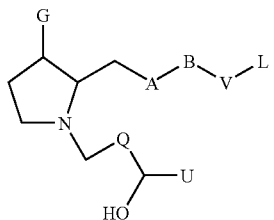

XIII wherein A is $CR^2R^3$;
B is $(CR^2R^3)_m$, or absent; or
A and B taken in combination form an optionally substituted 1,2-vinylene group or an ethynyl group;
V is $(CR^2R^3)_m$, optionally substituted divalent aryl, or optionally substituted divalent heteroaryl;
L is C(O)Z;
G is halogen optionally substituted alkyl, or optionally substituted alkylcarboxylate ester;
Q is $(CR^2R^3)_q$ which may include 0 or 1 C=C double bonds;

U is an optionally substituted alkyl group;
Z is hydroxy, optionally substituted alkyl, optionally substituted alkenyl, optionally substituted alkynyl, optionally substituted heteroalkyl, optionally substituted heteroalkenyl optionally substituted heteroalkynyl, amino, $NR^4R^5$, optionally substituted cycloalkyl, optionally substituted heterocycloalkyl, optionally substituted carbocyclic aryl, optionally substituted heteroaryl, optionally substituted arylalkyl, or optionally substituted heteroarylalkyl;
n is an integer selected from 0-3;
m is an integer selected from 1-6;
q is an integer selected from 0-5; and
$R^2$ and $R^3$ are independently hydroxy, optionally substituted alkyl, optionally substituted alkenyl, optionally substituted alkynyl, optionally substituted heteroalkyl, optionally substituted heteroalkenyl, optionally substituted heteroalkynyl;
$R^4$ and $R^5$ are independently are independently selected at each occurrence from the group consisting of hydrogen optionally substituted alkyl, optionally substituted cycloalkyl, optionally substituted heterocycloalkyl, optionally substituted alkenyl, optionally substituted alkynyl, optionally substituted heteroalkyl, optionally substituted heteroalkenyl, optionally substituted heteroalkynyl, optionally substituted carbocyclic aryl, optionally substituted heteroaryl, optionally substituted arylalkyl, and optionally substituted heteroarylalkyl,
or $R^4$ and $R^5$ taken in combination is an optionally substituted heterocycloalkyl; and pharmaceutically acceptable salts thereof.

40. A compound of the following Formula XIV:

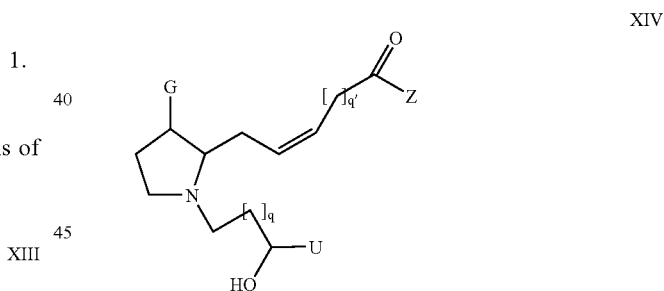

XIV wherein
q is an integer from 1-3;
q' is an integer from 2-4;
G is chloro, fluoro, methyl;
Z is hydroxy, $C_{1-6}$alkoxy, amino or mono $C_{1-6}$alkylamino or di-$C_{1-6}$alkylamino; and
U is a —$(CR^2R^3)_s$—W, wherein $R^2$ and $R^3$ are independently hydrogen, hydroxy, halogen, optionally substituted alkyl, optionally substituted cycloalkyl, optionally substituted alkenyl, optionally substituted alkynyl, optionally substituted heteroalkyl, optionally substituted heteroalkenyl, or optionally substituted heteroalkynyl;
s is an integer from 0-6; W is hydrogen or $C_{3-7}$cycloalkyl; and pharmaceutically acceptable salts thereof.

41. A compound of claim 1 wherein the compound is of the following Formula XV:

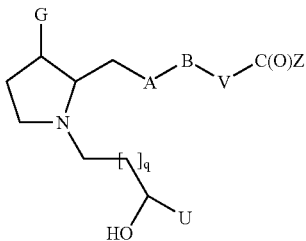

XV wherein A is ₂;
B is CH₂ or absent
V is divalent phenyl, divalent furan, or divalent thiophene;
q is an integer from 1-3;
G is chloro, fluoro, methyl;
Z is hydroxy, $C_{1-6}$alkoxy, amino or mono $C_{1-6}$alkylamino or di$C_{1-6}$alkylamino; and
U is a —$(CR^2R^3)_s$—W, wherein $R^2$ and $R^3$ are independently hydrogen, hydroxy, halogen, optionally substituted alkyl, optionally substituted cycloalkyl, optionally substituted alkenyl; optionally substituted alkynyl, optionally substituted heteroalkyl, optionally substituted heteroalkenyl, or optionally substituted heteroalkynyl;
s is an integer from 0-6; and W is hydrogen or $C_{3-7}$cycloalkyl; and pharmaceutically acceptable salts thereof.

42. A compound of claim 1 wherein the compound is:
7-[(2R,3R)-3-Chloro-1-(4-hydroxynonyl)-pyrrolidin-2-yl]-hept-5-enoic acid;
7-(-3-chloro-1-{4-[1-(cyclopropylmethyl)cyclobutyl]-4-hydroxybutyl}pyrrolidin-2-yl)hept-5-enoic acid;
7-{(3R)-3-chloro-1-[(2E)-4-hydroxynon-2-enyl]pyrrolidin-2-yl}hept-5-enoic acid;
7-{(3R)-3-chloro-1-[(2Z)-4-hydroxynon-2-enyl]pyrrolidin-2-yl}hept-5-enoic acid;
methyl 7-[(2R)-1-(3-hydroxyoctyl)-3-oxopyrrolidin-2-yl] hept-5-enoate;
4-{2-[3-chloro-1-(3-hydroxyoctyl)pyrrolidin-2-yl] ethyl}benzoic acid;
7-{3-chloro-1-[4-hydroxy-4-(1-propylcyclobutyl)butyl] pyrrolidin-2-yl}hept-5-enoic acid;
4-(2-{3-chloro-1-[(4R)-4-hydroxynonyl]pyrrolidin-2-yl}ethyl)benzoic acid;
(5Z)-7-{(2S,3R)-3-chloro-1-[(3R)-3-hydroxy-4-(3-methylphenyl)butyl]pyrrolidin-2-yl}hept 5-enoic acid;
(5Z)-7-{(2S,3R)-3-chloro-1-[(3S)-3-hydroxy-4-(3-methylphenyl)butyl]pyrrolidin-2-yl}hept-5-enoic acid;
(5Z)-7-{(2S,3R)-1-[4-(1-butylcyclobutyl)-4-hydroxybutyl]-3-chloropyrrolidin-2-yl}hept-5-enoic acid;
4-{2-[(2S,3R)-3-chloro-1-(4-hydroxynonyl)pyrrolidin-2-yl]ethyl}benzoic acid;
(5Z)-7-{(2S,3R)-3-chloro-1-[4-(1-ethylcyclobutyl)-4-hydroxybutyl]pyrrolidin-2-yl}hept-5-enoic acid;
(5Z)-7-[(2S,3R)-3-chloro-1-(4-hydroxynonyl)pyrrolidin-2-yl]hept-5-enoic acid or 4-(2-{1-[4-(1-butylcyclobutyl)-4-hydroxybutyl]-3-chloropyrrolidin-2-yl}ethyl) benzoic acid;
and pharmaceutically acceptable salts thereof.

43. A pharmaceutical composition comprising a pharmaceutically acceptable carrier and one or more compounds of claim 1.

44. A composition of claim 43 wherein the compound is packaged together with instructions for use of the compound to treat preterm labor, dysmenorrhea, asthma, hypertension, infertility or a fertility disorder, sexual dysfunction, undesired blood clotting, a destructive bone disease or disorder, preeclampsia or eclampsia, or an eosinophil disorder.

45. A composition of claim 43 wherein the composition further comprises one or more phosphodiesterase inhibitor compounds.

* * * * *